(12) United States Patent
Andreyev et al.

(10) Patent No.: US 10,987,674 B2
(45) Date of Patent: Apr. 27, 2021

(54) PRINTED CIRCUIT BOARD HEATER FOR AN AMPLIFICATION MODULE

(71) Applicant: Visby Medical, Inc., San Jose, CA (US)

(72) Inventors: Boris Andreyev, Foster City, CA (US); Brian Ciopyk, Pleasanton, CA (US); Victor Briones, Gilroy, CA (US); Jonathan Hong, San Jose, CA (US); David Swenson, Santa Clara, CA (US); Gregory Loney, Los Altos, CA (US); Adam De La Zerda, Palo Alto, CA (US); Steven Chu, Menlo Park, CA (US)

(73) Assignee: Visby Medical, Inc., San Jose, CA (US)

( * ) Notice: Subject to any disclaimer, the term of this patent is extended or adjusted under 35 U.S.C. 154(b) by 730 days.

(21) Appl. No.: 15/494,145

(22) Filed: Apr. 21, 2017

(65) Prior Publication Data

US 2017/0304829 A1    Oct. 26, 2017

Related U.S. Application Data

(60) Provisional application No. 62/326,289, filed on Apr. 22, 2016.

(51) Int. Cl.
*B01L 7/00* (2006.01)
*H05B 3/26* (2006.01)
(Continued)

(52) U.S. Cl.
CPC .............. *B01L 7/525* (2013.01); *C12Q 1/686* (2013.01); *H05B 1/025* (2013.01); *H05B 3/26* (2013.01);
(Continued)

(58) Field of Classification Search
CPC .............. B01L 7/525; B01L 2300/0816; B01L 2300/0887; B01L 2300/1805; B01L 2300/1827; B01L 2300/1883; B01L 7/52
See application file for complete search history.

(56) References Cited

U.S. PATENT DOCUMENTS

| 3,697,227 A | 10/1972 | Goldstein et al. |
| 5,164,159 A | 11/1992 | Hayashi et al. |

(Continued)

FOREIGN PATENT DOCUMENTS

| WO | WO2001/049416 A1 | 7/2001 |
| WO | WO2008/149111 A1 | 12/2008 |

(Continued)

OTHER PUBLICATIONS

Hwang et al., "Black Printed Circuit Board-based Micro-Polymerase Chain Reaction Chip Structure for Fluorescence Detection Test", International Journal of Control and Automation (2015); vol. 8, No. 10: pp. 15-24 (10 pages).

(Continued)

*Primary Examiner* — Jill A Warden
*Assistant Examiner* — Dwayne K Handy
(74) *Attorney, Agent, or Firm* — ReavesColey PLLC

(57) ABSTRACT

An apparatus includes a substrate, a first heating element, and a second heating element. The substrate includes a first portion, a second portion, and a third portion that is between the first portion and the second portion. The first portion is characterized by a first thermal conductivity, the second portion is characterized by a second thermal conductivity, and the third portion is characterized by a third thermal conductivity. The third thermal conductivity is less than the first thermal conductivity and the second thermal conductivity. The first heating element is coupled to the first portion of the substrate, and is configured to produce a first thermal (Continued)

output. The second heating element is coupled to the second portion of the substrate, and configured to produce a second thermal output. The second thermal output is different from the first thermal output.

19 Claims, 26 Drawing Sheets

(51) Int. Cl.
*C12Q 1/686* (2018.01)
*H05B 1/02* (2006.01)

(52) U.S. Cl.
CPC .................. *B01L 2300/0816* (2013.01); *B01L 2300/0883* (2013.01); *B01L 2300/0887* (2013.01); *B01L 2300/1805* (2013.01); *B01L 2300/1827* (2013.01); *B01L 2300/1883* (2013.01); *H05B 2203/003* (2013.01); *H05B 2203/021* (2013.01)

(56) References Cited

U.S. PATENT DOCUMENTS

| | | | |
|---|---|---|---|
| 5,229,297 A | 7/1993 | Schnipelsky et al. |
| 5,270,183 A | 12/1993 | Corbett et al. |
| 5,498,392 A | 3/1996 | Wilding et al. |
| 5,631,165 A | 5/1997 | Chupp et al. |
| 5,660,993 A | 8/1997 | Cathey et al. |
| 5,726,026 A | 3/1998 | Wilding et al. |
| 5,882,903 A | 3/1999 | Andrevski et al. |
| 5,922,591 A | 7/1999 | Anderson et al. |
| 6,126,804 A | 10/2000 | Andresen |
| 6,153,425 A | 11/2000 | Kozwich et al. |
| 6,235,479 B1 | 5/2001 | Rogers |
| 6,261,431 B1 | 7/2001 | Mathies et al. |
| 6,303,081 B1 | 10/2001 | Mink et al. |
| 6,365,378 B1 | 4/2002 | Hirota et al. |
| 6,369,893 B1 | 4/2002 | Christel et al. |
| 6,374,684 B1 | 4/2002 | Dority |
| 6,426,215 B1 | 7/2002 | Sandell |
| 6,514,750 B2 | 2/2003 | Bordenkircher et al. |
| 6,610,499 B1 | 8/2003 | Fulwyler et al. |
| 6,649,378 B1 | 11/2003 | Kozwich et al. |
| 6,656,744 B2 | 12/2003 | Pronovost et al. |
| 6,677,151 B2 | 1/2004 | Sandell |
| 6,767,512 B1 | 7/2004 | Lurz et al. |
| 6,780,617 B2 | 8/2004 | Chen |
| 6,781,056 B1 | 8/2004 | O'Rourke et al. |
| 6,813,568 B2 | 11/2004 | Powell et al. |
| 6,821,771 B2 | 11/2004 | Festoc |
| 6,893,879 B2 | 5/2005 | Petersen et al. |
| 6,901,217 B2 | 5/2005 | Gamboa et al. |
| 6,990,290 B2 | 1/2006 | Kylberg et al. |
| 7,041,481 B2 | 5/2006 | Anderson et al. |
| 7,144,742 B2 | 12/2006 | Boehringer et al. |
| 7,179,639 B2 | 2/2007 | Pottathil et al. |
| 7,189,522 B2 | 3/2007 | Esfandiari |
| 7,192,721 B1 | 3/2007 | Esfandiari |
| 7,297,313 B1 | 11/2007 | Northrup et al. |
| 7,341,697 B2 | 3/2008 | Takeuchi et al. |
| 7,378,285 B2 | 5/2008 | Lambotte et al. |
| 7,384,782 B2 | 6/2008 | Nakatani et al. |
| 7,416,892 B2 | 8/2008 | Battrell et al. |
| 7,438,852 B2 | 10/2008 | Tung et al. |
| 7,459,302 B2 | 12/2008 | Reid et al. |
| 7,491,551 B2 | 2/2009 | Boehringer et al. |
| 7,517,495 B2 | 4/2009 | Wu et al. |
| 7,544,324 B2 | 6/2009 | Tung et al. |
| 7,550,112 B2 | 6/2009 | Gou et al. |
| 7,553,675 B2 | 6/2009 | Jerome et al. |
| 7,569,382 B2 | 8/2009 | Li |
| 7,579,172 B2 | 8/2009 | Cho et al. |
| 7,592,139 B2 | 9/2009 | West et al. |
| 7,632,687 B2 | 12/2009 | Gokhan |
| 7,648,835 B2 | 1/2010 | Breidford et al. |
| 7,682,801 B2 | 3/2010 | Esfandiari |
| 7,691,644 B2 | 4/2010 | Lambotte et al. |
| 7,705,339 B2 | 4/2010 | Smith et al. |
| 7,709,250 B2 | 5/2010 | Corbett et al. |
| 7,754,452 B2 | 7/2010 | Kim et al. |
| 7,767,439 B2 | 8/2010 | Oh et al. |
| 7,794,656 B2 | 9/2010 | Liang et al. |
| 7,799,521 B2 | 9/2010 | Chen et al. |
| 7,837,939 B2 | 11/2010 | Tung et al. |
| 7,858,396 B2 | 12/2010 | Corstjens et al. |
| 7,871,568 B2 | 1/2011 | Liang et al. |
| 7,879,293 B2 | 2/2011 | Niedbala et al. |
| 7,914,986 B2 | 3/2011 | Nunn |
| 7,915,013 B2 | 3/2011 | Cho et al. |
| 7,959,877 B2 | 6/2011 | Esfandiari |
| 7,985,716 B2 | 7/2011 | Yershov et al. |
| 7,988,915 B2 | 8/2011 | Lee et al. |
| 7,998,757 B2 | 8/2011 | Darrigrand et al. |
| 8,008,046 B2 | 8/2011 | Maltezos et al. |
| 8,018,593 B2 | 9/2011 | Tan et al. |
| 8,048,386 B2 | 11/2011 | Dority et al. |
| 8,062,883 B2 | 11/2011 | Woudenberg et al. |
| 8,075,854 B2 | 12/2011 | Yang et al. |
| 8,088,616 B2 | 1/2012 | Handique |
| 8,110,392 B2 | 2/2012 | Battrell et al. |
| 8,133,671 B2 | 3/2012 | Williams et al. |
| 8,133,703 B2 | 3/2012 | Ching et al. |
| 8,163,489 B2 | 4/2012 | Murray et al. |
| 8,163,535 B2 | 4/2012 | Reed et al. |
| 8,169,610 B2 | 5/2012 | Oldham et al. |
| 8,173,077 B2 | 5/2012 | Korampally et al. |
| 8,198,074 B2 | 6/2012 | Moriwaki et al. |
| 8,216,832 B2 | 7/2012 | Battrell et al. |
| 8,231,844 B2 | 7/2012 | Gorfinkel |
| 8,232,091 B2 | 7/2012 | Maltezos et al. |
| 8,232,094 B2 | 7/2012 | Hasson et al. |
| 8,247,221 B2 | 8/2012 | Fawcett |
| 8,263,392 B2 | 9/2012 | Gale et al. |
| 8,277,763 B2 | 10/2012 | Steinmann et al. |
| 8,278,091 B2 | 10/2012 | Rutter et al. |
| 8,298,763 B2 | 10/2012 | Regan |
| 8,323,583 B2 | 12/2012 | Gou et al. |
| 8,329,453 B2 | 12/2012 | Battrell et al. |
| 8,343,442 B2 | 1/2013 | McBride et al. |
| 8,343,754 B2 | 1/2013 | Wittwer et al. |
| 8,357,490 B2 | 1/2013 | Froehlich et al. |
| 8,372,340 B2 | 2/2013 | Bird et al. |
| 8,389,960 B2 | 3/2013 | Pieprzyk et al. |
| 8,394,608 B2 | 3/2013 | Ririe et al. |
| 8,394,626 B2 | 3/2013 | Ramsey et al. |
| 8,426,134 B2 | 4/2013 | Piepenburg et al. |
| 8,435,461 B2 | 5/2013 | Kirby et al. |
| 8,492,136 B2 | 7/2013 | Carlisle et al. |
| 8,507,259 B2 | 8/2013 | Esfandiari |
| 8,580,507 B2 | 11/2013 | Piepenburg et al. |
| 8,580,575 B2 | 11/2013 | Hanafusa |
| 8,597,937 B2 | 12/2013 | Ward et al. |
| 8,603,835 B2 | 12/2013 | Esfandiari |
| 8,617,486 B2 | 12/2013 | Kirby et al. |
| 8,629,264 B2 | 1/2014 | Reed et al. |
| 8,637,250 B2 | 1/2014 | Jenison |
| 8,663,976 B2 | 3/2014 | Chung et al. |
| 8,673,239 B2 | 3/2014 | Niedbala et al. |
| 8,691,561 B2 | 4/2014 | Igata |
| 8,722,426 B2 | 5/2014 | Lambotte et al. |
| 8,728,765 B2 | 5/2014 | Ching et al. |
| 8,765,367 B2 | 7/2014 | Breidenthal et al. |
| 8,772,017 B2 | 7/2014 | Battrell et al. |
| 8,795,592 B2 | 8/2014 | Eiriksson |
| 8,859,199 B2 | 10/2014 | Hellyer et al. |
| 8,865,458 B2 | 10/2014 | Ramsey et al. |
| 8,871,155 B2 | 10/2014 | Wu et al. |
| 8,877,450 B2 | 11/2014 | Esfandiari |
| 8,894,946 B2 | 11/2014 | Nielsen et al. |
| 8,900,828 B2 | 12/2014 | Smith et al. |
| 8,900,853 B2 | 12/2014 | Verhaar et al. |
| 8,911,941 B2 | 12/2014 | Michlitsch |
| 8,911,949 B2 | 12/2014 | Bertrand et al. |

(56) References Cited

U.S. PATENT DOCUMENTS

| | | | |
|---|---|---|---|
| 8,916,375 B2 | 12/2014 | Landers et al. |
| 8,945,843 B2 | 2/2015 | Alvin et al. |
| 8,975,027 B2 | 3/2015 | Gale et al. |
| 8,980,177 B2 | 3/2015 | Carlisle et al. |
| 8,986,927 B2 | 3/2015 | Lee et al. |
| 8,992,854 B2 | 3/2015 | Brewster et al. |
| 9,011,770 B2 | 4/2015 | Wu et al. |
| 9,012,236 B2 | 4/2015 | Jovanovich et al. |
| 9,023,639 B2 | 5/2015 | Kim et al. |
| 9,044,729 B2 | 6/2015 | Rengifo et al. |
| 9,150,907 B2 | 10/2015 | Shaikh et al. |
| 9,207,236 B2 | 12/2015 | Cary |
| 9,238,833 B2 | 1/2016 | Chen et al. |
| 9,260,750 B2 | 2/2016 | Hillebrand et al. |
| 9,268,911 B2 | 2/2016 | Sia et al. |
| 9,387,478 B2 | 7/2016 | Bergstedt et al. |
| 9,428,781 B2 | 8/2016 | Cai et al. |
| 9,453,255 B2 | 9/2016 | Ozawa et al. |
| 9,469,871 B2 | 10/2016 | Bearinger et al. |
| 9,475,049 B2 | 10/2016 | Siciliano |
| D776,290 S | 1/2017 | Wan et al. |
| 9,623,415 B2 | 4/2017 | Andreyev et al. |
| 9,752,182 B2 | 9/2017 | Collier et al. |
| 10,040,069 B2 | 8/2018 | Moore et al. |
| 10,052,629 B2 | 8/2018 | Andreyev et al. |
| 10,112,196 B2 | 10/2018 | Andreyev et al. |
| 10,112,197 B2 | 10/2018 | Andreyev et al. |
| 10,124,334 B2 | 11/2018 | Andreyev et al. |
| 10,173,182 B2 | 1/2019 | Tachibana et al. |
| 10,195,610 B2 | 2/2019 | Tang et al. |
| 10,603,664 B2 | 3/2020 | Khattak et al. |
| 2004/0209331 A1 | 10/2004 | Ririe |
| 2004/0224317 A1 | 11/2004 | Kordunsky et al. |
| 2005/0064598 A1 | 3/2005 | Yuan et al. |
| 2005/0100946 A1 | 5/2005 | Lipshutz et al. |
| 2005/0142036 A1* | 6/2005 | Kim ............... B01L 7/00 422/504 |
| 2005/0194316 A1 | 9/2005 | Pourahmadi et al. |
| 2005/0227275 A1 | 10/2005 | Jung et al. |
| 2006/0001689 A1 | 1/2006 | Ahne et al. |
| 2006/0088931 A1 | 4/2006 | Ririe |
| 2006/0127924 A1 | 6/2006 | Hellyer et al. |
| 2006/0154341 A1 | 7/2006 | Chen |
| 2006/0160205 A1 | 7/2006 | Blackburn et al. |
| 2006/0246493 A1 | 11/2006 | Jensen et al. |
| 2006/0258012 A1 | 11/2006 | Yang et al. |
| 2007/0042427 A1 | 2/2007 | Gerdes et al. |
| 2007/0154922 A1 | 7/2007 | Collier et al. |
| 2007/0284360 A1 | 12/2007 | Santoruvo et al. |
| 2008/0038737 A1 | 2/2008 | Smith et al. |
| 2008/0050735 A1 | 2/2008 | Pushnova |
| 2008/0113391 A1 | 5/2008 | Gibbons et al. |
| 2008/0274513 A1 | 11/2008 | Shenderov et al. |
| 2008/0280285 A1 | 11/2008 | Chen et al. |
| 2009/0029422 A1 | 1/2009 | Hanafusa et al. |
| 2009/0042256 A1 | 2/2009 | Hanafusa et al. |
| 2009/0130745 A1 | 5/2009 | Williams et al. |
| 2009/0186344 A1 | 7/2009 | Farinas |
| 2009/0215072 A1 | 8/2009 | McDevitt et al. |
| 2009/0325276 A1 | 12/2009 | Battrell et al. |
| 2010/0003683 A1 | 1/2010 | Sarofim et al. |
| 2010/0025242 A1* | 2/2010 | Pamula .......... B01F 13/0071 204/450 |
| 2010/0173393 A1 | 7/2010 | Handique et al. |
| 2010/0210038 A1 | 8/2010 | Blatt et al. |
| 2010/0291588 A1 | 11/2010 | McDevitt et al. |
| 2010/0297640 A1 | 11/2010 | Kumar et al. |
| 2011/0020876 A1 | 1/2011 | Wilding et al. |
| 2011/0039303 A1 | 2/2011 | Janovich et al. |
| 2011/0160090 A1 | 6/2011 | Cary |
| 2011/0211331 A1 | 9/2011 | Alkjaer et al. |
| 2011/0227551 A1 | 9/2011 | Black |
| 2011/0269191 A1 | 11/2011 | Belgrader et al. |
| 2011/0275055 A1 | 11/2011 | Conner |
| 2011/0312793 A1 | 12/2011 | Azimi et al. |
| 2011/0312841 A1 | 12/2011 | Silverbrook et al. |
| 2011/0313148 A1 | 12/2011 | Christ et al. |
| 2012/0021454 A1 | 1/2012 | Bikker et al. |
| 2012/0064534 A1 | 3/2012 | Pipper et al. |
| 2012/0070878 A1 | 3/2012 | Fink et al. |
| 2012/0088294 A1 | 4/2012 | Sun et al. |
| 2012/0135511 A1 | 5/2012 | Battrell et al. |
| 2012/0141337 A1 | 6/2012 | Maltezos et al. |
| 2012/0264202 A1 | 10/2012 | Walker et al. |
| 2012/0288897 A1 | 11/2012 | Ching et al. |
| 2013/0040296 A1 | 2/2013 | Tulp et al. |
| 2013/0053255 A1 | 2/2013 | Vangbo et al. |
| 2013/0059290 A1 | 3/2013 | Armes |
| 2013/0078736 A1 | 3/2013 | Grover et al. |
| 2013/0115712 A1 | 5/2013 | Yu et al. |
| 2013/0118900 A1 | 5/2013 | Reimitz et al. |
| 2013/0149710 A1 | 6/2013 | Yoon et al. |
| 2013/0210080 A1 | 8/2013 | Rajagopal et al. |
| 2013/0217026 A1 | 8/2013 | Egan et al. |
| 2013/0220781 A1 | 8/2013 | Czarnecki |
| 2014/0045191 A1 | 2/2014 | DeJohn et al. |
| 2014/0051159 A1 | 2/2014 | Bergstedt et al. |
| 2014/0073013 A1 | 3/2014 | Gorman et al. |
| 2014/0087359 A1 | 3/2014 | Njoroge et al. |
| 2014/0274770 A1 | 9/2014 | Pack |
| 2015/0031087 A1 | 1/2015 | Nagai et al. |
| 2015/0182966 A1 | 7/2015 | Coursey et al. |
| 2015/0240298 A1 | 8/2015 | Piepenburg et al. |
| 2015/0258273 A1 | 9/2015 | Payne et al. |
| 2015/0346097 A1 | 12/2015 | Battrell et al. |
| 2016/0054316 A1 | 2/2016 | Egan et al. |
| 2016/0222442 A1 | 8/2016 | Cary |
| 2016/0256870 A1 | 9/2016 | Ismagilov et al. |
| 2016/0289669 A1 | 10/2016 | Fan et al. |
| 2016/0310948 A1 | 10/2016 | Nowakowski et al. |
| 2017/0021356 A1 | 1/2017 | Dority et al. |
| 2017/0058324 A1 | 3/2017 | Balog et al. |
| 2017/0173585 A1 | 6/2017 | Mahony et al. |
| 2017/0304829 A1 | 10/2017 | Andreyev et al. |
| 2018/0304260 A1 | 10/2018 | Thomas et al. |
| 2019/0022643 A1 | 1/2019 | Andreyev et al. |
| 2019/0030532 A1 | 1/2019 | Andreyev et al. |
| 2019/0040451 A1 | 2/2019 | Mahony et al. |
| 2019/0060895 A1 | 2/2019 | Myers, III et al. |
| 2019/0083975 A1 | 3/2019 | Mitra et al. |
| 2019/0094114 A1 | 3/2019 | Myers, III et al. |
| 2019/0136226 A1 | 5/2019 | Swenson et al. |
| 2019/0151844 A1 | 5/2019 | Andreyev et al. |
| 2019/0169677 A1 | 6/2019 | Andreyev et al. |
| 2019/0193077 A1 | 6/2019 | Andreyev et al. |
| 2019/0232283 A1 | 8/2019 | Andreyev et al. |
| 2019/0232293 A1 | 8/2019 | Tang et al. |
| 2020/0086324 A1 | 3/2020 | Swenson et al. |

FOREIGN PATENT DOCUMENTS

| | | |
|---|---|---|
| WO | WO2014/035986 A1 | 3/2014 |
| WO | WO2014/144548 A2 | 9/2014 |
| WO | WO2015/138343 A1 | 9/2015 |
| WO | WO2015/138648 A1 | 9/2015 |
| WO | WO2015/164770 A1 | 10/2015 |
| WO | WO2016/040523 A1 | 3/2016 |
| WO | WO2016/203019 A1 | 12/2016 |
| WO | WO2017/197040 A1 | 11/2017 |
| WO | WO2018/005710 A1 | 1/2018 |
| WO | WO2018/005870 A1 | 1/2018 |

OTHER PUBLICATIONS

Kopp et al., "Chemical Amplification: Continuous-Flow PCR on a Chip", Science (1998); 280 (5366): 1046-1048.

Schwerdt. Application of ferrofiuid as a valve/pump for polycarbonate microfluidic devices. Johns Hopkins University. NSF Summer Undergraduate Fellowship in Sensor Technologies 2006, 17 pages.

Tanriverdi et al. A rapid and automated sample-to-result HIV load test for near-patient application. J Infect Dis., 201 Suppl 1:S52-S58, 2010.

(56) References Cited

OTHER PUBLICATIONS

Mohammed et al., Modeling of Serpentine Continuous Flow Polymerase Chain Reaction Microfluidics.
U.S. Appl. No. 14/984,573 First Action Interview Pilot Program Pre-Interview Communication dated Aug. 16, 2016.
International Search Report and Written Opinion for International Application No. PCT/US2018/060117, dated Apr. 12, 2019.
Lee et al. "A polymer lab-on-a-chip for reverse transcription (RT)-PCR based point-of-care clinical diagnostics," The Royal Society of Chemistry, vol. 8, pp. 2121-2127, Oct. 31, 2008.
Gehring et al. "A High-Throughput, Precipitating Colorimetric Sandwich ELISA Microarray for Shiga Toxins," J. Toxins, vol. 6, p. 1855-72, Jun. 11, 2014.
Interbiotech, "Enzymatic substrates for ImmunoAssays," [retrieved from the Internet Nov. 18, 2017: <http://www.interchim.fr/ft/B/BA357a.pdf>], 10 pages.
Kim, Yong Tae et al. "Integrated Microdevice of reverse transcription-polymerase chain reaction with colorimetric immunochromatographic detection for rapid gene expression analysis of influenza A H1N1 virus," Biosensors and Bioelectronics, Elsevier Science Ltd UK, Amsterdam, NL V. 33 No. 1, pp. 88-94.
Kim, Jungkyu et al. "Automated microfluidic DNA/RNA extraction with both disposable and reusable components," Journal of Micromechanics and Microengineering, Vo. 22, No. 1, Dec. 20, 2011.
Roskos, Kristina et al. "Simple System for Isothermal DNA Amplification Coupled to Lateral Flow Detection," PLoS One, vol. 8, No. 7, Jul. 26, 2013, p. e69355, XP055495626, DOI: 10.1371/journal.pone.0069355.
Shafagati, et al., The Use of NanoTrap Particles as a Sample Enrichment Method to Enhance the Detection of Rift Valley Fever Virus. PLOS Neglected Tropical Diseases, Jul. 4, 2013; 7(7): e2296.
International Search Report and Written Opinion for International Application No. PCT/US2017/029004, dated Aug. 23, 2017.
Brunklaus, S. et al., Fast nucleic acid amplification for integration in point-of-care applications, Electrophoresis, 2012, vol. 33, pp. 3222-3228.
Choi, Gihoon et al., "A field-deployable mobile molecular diagnostic system for malaria at the point of need," Lab on a Chip, Royal Society of Chemistry, 2016, 16, 4341-4349.
Lee et al. "Single-channel multiplexing without melting curve analysis in real-time PCR," Scientific Reports, Dec. 11, 2014, vol. 4, Art. No. 7439, pp. 1-6, entire document.
Huang et al., "Efficient SNP Discovery by Combining Microarray and Lab-on-a-Chip Data for Animal Breeding and Selection," Microarrays, Nov. 16, 2015, vol. 4, No. 4, pp. 570-595, entire document.
Wheeler, E.K., 'Under-three minute PCR: Probing the limits of fast amplification', published Jul. 27, 2011 by the Royal Society of Chemistry: Analyst 2011 vol. 136 pp. 3707-3712.
Moschou D., et al., 'All-plastic, low-power, disposable, continuous-flow PCR chip with integrated microheaters for rapid DNA amplification', Sensors and Actuators B: Chemical, vol. 199, Aug. 1, 2014, pp. 470-478.

\* cited by examiner

```
10
```

Convey a sample into a diagnostic device, the diagnostic device including a flow member coupled to a first heater assembly and a second heater assembly, the flow member defining a flow path having a set of flow channels, the first heater assembly including a first heating element and a second heating element, the second heater assembly including a third heating element and a fourth heating element
12

Actuate the diagnostic device to:
13

Supply, at a first time, current to the first heating element and the third heating element such that the first heating element maintains at least a first portion of a first channel from the plurality of channels at a first temperature and the third heating element maintains at least a second portion of the first channel from the plurality of channels at a second temperature
13A Produce, at a second time, a flow of the sample within the flow path, the second time after the first time
13B Supply, at a third time, current to the second heating element and the fourth heating element such that the second heating element maintains at least a first portion of a second channel from the plurality of channels at the first temperature and the fourth heating element maintains at least a second portion of the second channel from the plurality of channels at the second temperature, the third time different from the first time
13C

Convey a sample into a diagnostic device, the diagnostic device including a flow member coupled to a heater assembly. The flow member defining a flow path. The heater assembly including a substrate, a first heating element, and a second heating element. The first heating element is between a first portion of the substrate and a first portion of the flow path, and the second heating element is between a second portion of the substrate and a second portion of the flow path. A third portion of the substrate separates the first portion of the substrate and the second portion of the substrate, the third portion of the substrate characterized by a thermal conductivity that is less than a thermal conductivity of the first portion of the substrate.
22

Actuate the diagnostic device to:
23

Supply a first current to the first heating element such that the first heating element maintains the first portion of the flow path at a first temperature
23A Supply a second current to the second heating element such that the second heating element maintains the second portion of the flow path at a second temperature, the second temperature different from the first temperature
23B Produce a flow of the sample within the flow path
23C

FIG. 27

PRINTED CIRCUIT BOARD HEATER FOR AN AMPLIFICATION MODULE

CROSS-REFERENCE TO RELATED APPLICATIONS

This application claims benefit of priority to U.S. Provisional Application Ser. No. 62/326,289, entitled "Segmented Heater for a PCR Module," filed Apr. 22, 2016, which is incorporated herein by reference in its entirety.

BACKGROUND

The embodiments described herein relate to devices and methods for molecular diagnostic testing. More particularly, the embodiments described herein relate to heaters and methods of heating a sample volume to amplify a nucleic acid in a molecular diagnostic testing device.

There are over one billion infections in the U.S. each year, many of which are treated incorrectly due to inaccurate or delayed diagnostic results. Many known point of care (POC) tests have poor sensitivity (30-70%), while the more highly sensitive tests, such as those involving the specific detection of nucleic acids or molecular testing associated with a pathogenic target, are only available in laboratories. Thus, molecular diagnostics testing is often practiced in centralized laboratories. Known devices and methods for conducting laboratory-based molecular diagnostics testing, however, require trained personnel, regulated infrastructure, and expensive, high throughput instrumentation. Known high throughput laboratory equipment generally processes many (96 to 384 and more) samples at a time, therefore central lab testing is often done in batches. Known methods for processing test samples typically include processing all samples collected during a time period (e.g., a day) in one large run, resulting in a turn-around time of many hours to days after the sample is collected. Moreover, such known instrumentation and methods are designed to perform certain operations under the guidance of a skilled technician who adds reagents, oversees processing, and moves sample from step to step. Thus, although known laboratory tests and methods are very accurate, they often take considerable time, and are very expensive.

There are limited testing options available for testing done at the point of care ("POC"), or in other locations outside of a laboratory. Known POC testing options are often single analyte tests with low analytical quality. These tests are used alongside clinical algorithms to assist in diagnosis, but are frequently verified by higher quality, laboratory tests for the definitive diagnosis. Thus, in many instances, neither consumers nor physicians are enabled to achieve a rapid, accurate test result in time to "test and treat" in one visit. As a result, doctors and patients often determine a course of treatment before they know the diagnosis. This has tremendous ramifications: antibiotics are either not prescribed when needed, leading to infections; or antibiotics are prescribed when not needed, leading to new antibiotic-resistant strains in the community. Moreover, known systems and methods often result in diagnosis of severe viral infections, such as H1N1 swine flu, too late, limiting containment efforts. In addition, patients lose time in unnecessary, repeated doctor visits.

Moreover, many known POC diagnostic devices employ test strips or other simple detection mechanisms, and often do not amplify the target organism. Although recent advances in technology have enabled the development of "lab on a chip" devices, such devices are often not optimized for point-of-care testing. For example, some known devices and methods require continuous power usage to thermally cycle the sample, which can limit the ability to produce a portable or "in home" test. Other known devices include cumbersome resistance heaters and heat sinking arrangements that are not conducive to portable or "in home" tests. Specifically, such devices can have high power usage and can be too large to be reasonably packaged for use as a POC test.

Moreover, many known "lab on a chip" devices amplify a very small volume of sample (e.g., less than one microliter), and are therefore not suited for analyzing for multiple different indications (e.g., a 3-plex or 4-plex test).

Reducing the package size of a diagnostic device can also negatively impact the accuracy to which amplification temperatures are controlled. For example, the size, shape and packaging of certain structures (e.g., a heater, a flow member, or the like) can cause spatial variations in temperature within a reaction chamber. Moreover, tight packaging of electrical components (e.g., resistance heaters) and processors (e.g., control modules) can result in an undesirable level of electromagnetic field (EMF) noise.

Thus, a need exists for improved devices and methods for molecular diagnostic testing. In particular, a need exists for improved amplification modules, heaters and methods for amplifying a target nucleic acid in a molecular diagnostic testing device.

SUMMARY

Amplification modules and heaters for amplifying a nucleic acid within a sample are described herein. In some embodiments, an apparatus includes a substrate, a first heating element, and a second heating element. The substrate includes a first portion, a second portion, and a third portion that is between the first portion and the second portion. The first portion is characterized by a first thermal conductivity, the second portion is characterized by a second thermal conductivity, and the third portion is characterized by a third thermal conductivity. The third thermal conductivity is less than the first thermal conductivity and the second thermal conductivity. The first heating element is coupled to the first portion of the substrate, and is configured to produce a first thermal output. The second heating element is coupled to the second portion of the substrate, and configured to produce a second thermal output. The second thermal output is different from the first thermal output.

BRIEF DESCRIPTION OF THE DRAWINGS

FIG. 26 shows a flow chart of a method of performing sample amplification, according to an embodiment.

FIG. 27 shows a flow chart of a method of performing a thermal process on a sample, according to an embodiment.

DETAILED DESCRIPTION

Figure 1:
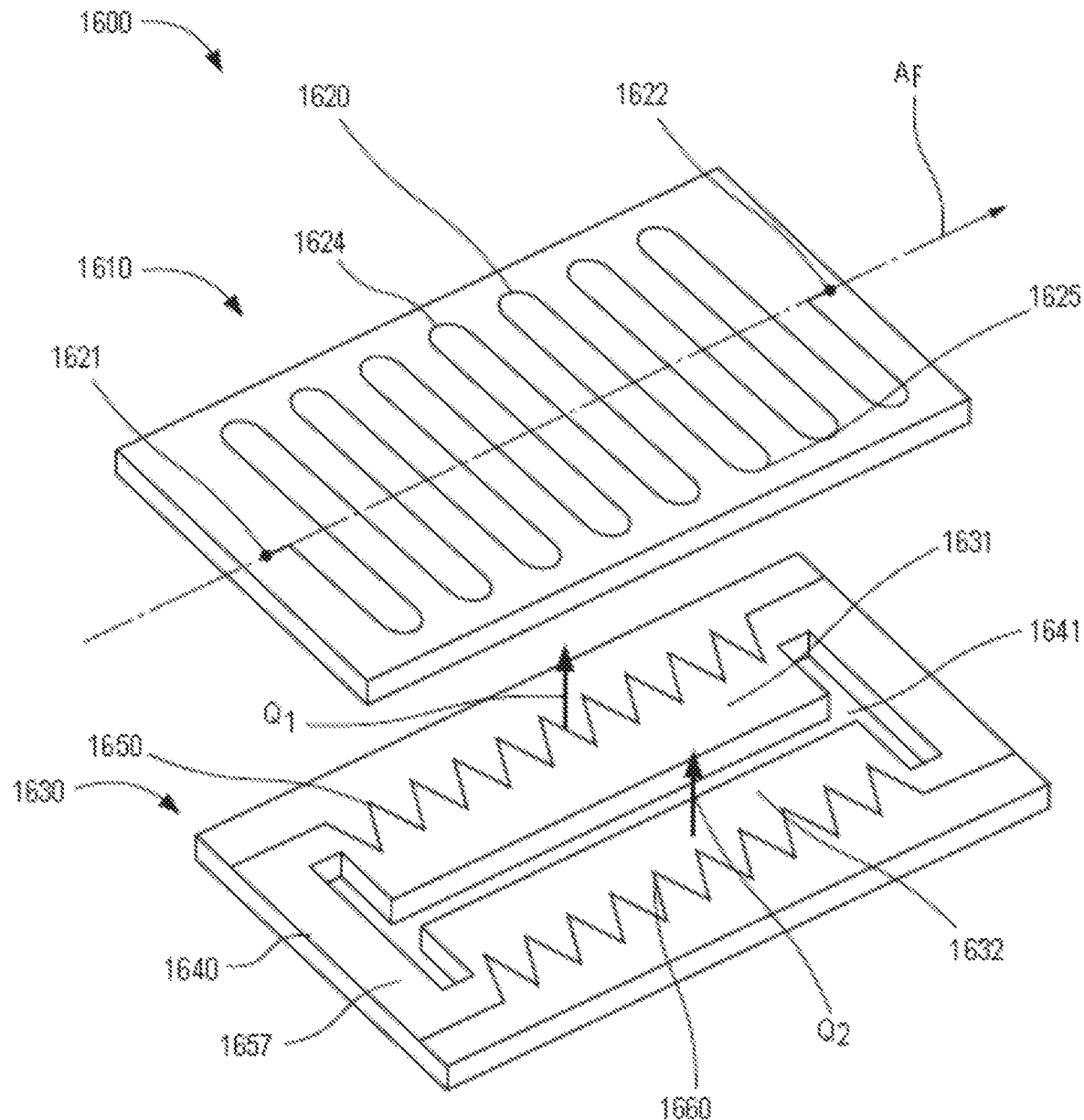
FIG. 1 is a perspective view schematic illustration of a thermal reaction module, according to an embodiment.

In some embodiments, an apparatus is configured for a disposable, portable, single-use, inexpensive, molecular diagnostic approach. The apparatus can include one or more modules configured to perform high quality molecular diagnostic tests, including, but not limited to, sample preparation, nucleic acid amplification (e.g., via polymerase chain reaction, isothermal amplification, or the like), and detection. In some embodiments, sample preparation can be performed by isolating the target pathogen/entity and removing unwanted amplification (e.g., PCR) inhibitors. The target entity can be subsequently lysed to release target nucleic acid for amplification. A target nucleic acid in the target entity can be amplified with a polymerase undergoing temperature cycling or via an isothermal incubation to yield a greater number of copies of the target nucleic acid sequence for detection.

In some embodiments, an amplification module includes a printed circuit board upon which a series of heaters is lithographically produced. The amplification module further includes a flow member coupled to the printed circuit board through which a sample is conveyed to amplify a target nucleic acid within the sample. The amplification can be performed, for example, by cycling the sample between various temperature set points, by maintaining the sample at a desired temperature (e.g., isothermal methods), or any other suitable method. In some embodiments, the printed circuit board also includes a processor or control module.

In some embodiments, an amplification module includes a substrate, a first heating element, and a second heating element. The substrate defines an aperture that separates the substrate into a first portion and a second portion. The first heating element is coupled to the first portion of the substrate, and is configured to produce a first thermal output. The second heating element is coupled to the second portion of the substrate, and configured to produce a second thermal output. The second thermal output is different from the first thermal output.

In some embodiments, an amplification module includes a substrate, a first heating element, and a second heating element. The substrate includes a first portion, a second portion, and a third portion that is between the first portion and the second portion. The first portion is characterized by a first thermal conductivity, the second portion is characterized by a second thermal conductivity, and the third portion is characterized by a third thermal conductivity. The third thermal conductivity is less than the first thermal conductivity and the second thermal conductivity.

In some embodiments, an amplification module includes a flow member, a substrate, a first heater assembly, and a second heater assembly. The flow member defines a flow path through which a sample can flow from an inlet opening to an outlet opening. The first heater assembly is coupled between the substrate and the flow member. The first heater assembly is configured to maintain a first portion of the flow member at a first temperature. The first heater assembly includes a first set of heating elements along a flow axis defined by the flow member. Each heating element from the first set of heating elements is electrically isolated from the other heating elements from the first set of heating elements. The second heater assembly is coupled between the substrate and the flow member. The second heater assembly is configured to maintain a second portion of the flow member at a second temperature. The second heater assembly includes a second set of heating elements along the flow axis. Each heating element from the second set of heating elements is electrically isolated from the other heating elements from the second set of heating elements.

In some embodiments, an amplification module can be included within a diagnostic device, which can be battery powered, allowing the diagnostic test(s) to be run without A/C power, and at any suitable location (e.g., outside of a laboratory and/or at any suitable "point of care"). In other embodiments, an amplification module, including any of the heater assemblies described herein, can be included within a diagnostic device that is compact and consumes a limited amount of power, thus being suitable for use in lower current A/C circuits.

In some embodiments, an amplification module can be included within a diagnostic device that is optimized for disposable and portable operation. For example, in some embodiments, an apparatus includes a power module operated by a small battery (e.g., a 9V battery). In such embodiments, the device can include a controller to control the timing and/or magnitude of power draw to accommodate the capacity of the battery.

In some embodiments, an amplification module can be included within a diagnostic device that is optimized for one-time use. In some embodiments, the diagnostic device is disposable via standard waste procedures after use.

In some embodiments, a method includes conveying a sample into a diagnostic device. The diagnostic device includes a flow member and a heater assembly. The flow member defines a flow path. The heater assembly includes a substrate, a first heating element, and a second heating element. The heater assembly coupled to the flow member such that the first heating element is between a first portion of the substrate and a first portion of the flow path, and the second heating element is between a second portion of the substrate and a second portion of the flow path. A third portion of the substrate separates the first portion of the substrate and the second portion of the substrate. The third portion of the substrate is characterized by a thermal conductivity that is less than a thermal conductivity of the first portion of the substrate. The device is then actuated to (1) supply a first current to the first heating element such that the first heating element maintains the first portion of the flow path at a first temperature; (2) supply a second current to the second heating element such that the second heating element maintains the second portion of the flow path at a second temperature that is different from the first temperature; and (3) produce a flow of the sample within the flow path.

In some embodiments, a method includes conveying a sample into a diagnostic device. The diagnostic device includes a flow member coupled to a first heater assembly and a second heater assembly. The flow member defines a flow path having a set of flow channels. The first heater assembly includes a first heating element and a second heating element. The second heater assembly includes a third heating element and a fourth heating element. The device is then actuated to (1) supply, at a first time, current to the first heating element and the third heating element such that the first heating element maintains at least a first portion of a first channel from the set of channels at a first temperature and the third heating element maintains at least a second portion of the first channel from the set of channels at a second temperature; (2) produce, at a second time, a flow of the sample within the flow path; and (3) supply, at a third time, current to the second heating element and the fourth heating element such that the second heating element maintains at least a first portion of a second channel from the set of channels at the first temperature and the fourth heating element maintains at least a second portion of the second channel from the set of channels at the second temperature. In some embodiments, the second time occurs after the first time, and the third time is different from the first time.

In some embodiments, a method includes conveying a sample into a diagnostic device. The diagnostic device includes a flow member coupled to a first heater assembly and a second heater assembly. The flow member defines a flow path having a plurality of flow channels. The first heater assembly includes a first heating element, and the second heater assembly includes a second heating element and a third heating element. The first heater assembly is coupled to the flow member such that the first heating element is aligned with a first portion of the flow path. The second heater assembly is coupled to the flow member such that and the second heating element and the third heating element are each aligned with a second portion of the flow path. The device is then actuated to (1) supply a first current to the first heating element such that the first heating element maintains the first portion of the flow path at a first temperature; (2) produce a flow of the sample within the flow path; (3) supply a second current to the second heating element; and (4) supply a third current to the third heating element. The third current is supplied independently from the second current, and the second current and the third current supplied such that the second heating element and the third heating element collectively maintain the second portion of the flow path at a second temperature.

As used herein, the term "about" when used in connection with a referenced numeric indication means the referenced numeric indication plus or minus up to 10% of that referenced numeric indication. For example, the language "about 50" covers the range of 45 to 55.

As used in this specification and the appended claims, the words "proximal" and "distal" refer to direction closer to and away from, respectively, an operator of the diagnostic device. Thus, for example, the end of an actuator depressed by a user that is furthest away from the user would be the distal end of the actuator, while the end opposite the distal end (i.e., the end manipulated by the user) would be the proximal end of the actuator.

The term "fluid-tight" is understood to encompass hermetic sealing (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at pressures of less than about 5 psig, less than about 10 psig, less than about 20 psig, less than about 30 psig, less than about 50 psig, less than about 75 psig, less than about 100 psig, and all values in between. Any residual fluid layer that may be present on a portion of a wall of a container after component defining a "substantially-fluid tight" seal are moved past the portion of the wall are not considered as leakage.

The term "parallel" is used herein to describe a relationship between two geometric constructions (e.g., two lines, two planes, a line and a plane, or the like) in which the two geometric constructions are non-intersecting as they extend substantially to infinity. For example, as used herein, a planar surface (i.e., a two-dimensional surface) is said to be parallel to a line when every point along the line is spaced apart from the nearest portion of the surface by a substantially equal distance. Similarly, a first line (or axis) is said to be parallel to a second line (or axis) when the first line and the second line do not intersect as they extend to infinity. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The terms "perpendicular," "orthogonal," and "normal" are used herein to describe a relationship between two geometric constructions (e.g., two lines, two planes, a line and a plane, or the like) in which the two geometric constructions intersect at an angle of approximately 90 degrees within at least one plane. For example, as used herein, a line (or axis) is said to be normal to a planar surface when the line and a portion of the planar surface intersect at an angle of approximately 90 degrees within the planar surface. Two geometric constructions are described herein as being, for example, "perpendicular" or "substantially perpendicular" to each other when they are nominally perpendicular to each other, such as for example, when they are perpendicular to each other within a tolerance. Such tolerances can include, for example, manufacturing tolerances, measurement tolerances or the like.

Similarly, geometric terms, such as "parallel," "perpendicular," "cylindrical," "square," "conical," or "frusto-conical" are not intended to require absolute mathematical precision, unless the context indicates otherwise. Instead, such geometric terms allow for variations due to manufacturing or equivalent functions. For example, if an element is described as "conical" or "generally conical," a component that is not precisely conical (e.g., one that is slightly oblong) is still encompassed by this description.

As used in this specification and the appended claims, the term "reagent" includes any substance that is used in connection with any of the reactions described herein. For example, a reagent can include an elution buffer, a PCR reagent, an enzyme, a substrate, a wash solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

The term "nucleic acid molecule," "nucleic acid," or "polynucleotide" may be used interchangeably herein, and may refer to deoxyribonucleic acid (DNA) or ribonucleic acid (RNA), including known analogs or a combination thereof unless otherwise indicated. Nucleic acid molecules to be profiled herein can be obtained from any source of nucleic acid. The nucleic acid molecule can be single-stranded or double-stranded. In some cases, the nucleic acid molecules are DNA The DNA can be mitochondrial DNA, complementary DNA (cDNA), or genomic DNA. In some cases, the nucleic acid molecules are genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can be derived from one or more of chromosomes 1, 2, 3, 4, 5, 6, 7, 8, 9, 10, 11, 12, 13, 14, 15, 16, 17, 18, 19, 20, 21, 22, X, or Y. In some cases, the nucleic acid molecules are RNA can include, but is not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs. The source of nucleic acid for use in the devices, methods, and compositions described herein can be a sample comprising the nucleic acid.

Unless indicated otherwise, the terms apparatus, diagnostic apparatus, diagnostic system, diagnostic test, diagnostic test system, test unit, and variants thereof, can be interchangeably used.

FIG. 1 is a schematic illustration of an amplification (or thermal reaction) module 1600, according to an embodiment. The amplification module 1600 is configured to perform a thermal reaction (e.g., an amplification reaction) on an input of target DNA mixed with required reagents, and can be included in any suitable diagnostic device. For example, the amplification module can be included in any of the diagnostic devices shown and described herein (including the device 6000 and the device 7000) or in International Patent Publication No. WO2016/109691, entitled "Devices and Methods for Molecular Diagnostic Testing," which is incorporated herein by reference in its entirety. In some embodiments, the amplification module 1600 is configured to conduct rapid PCR amplification of an input target. In some embodiments, the amplification module 1600 is configured to generate an output copy number that reaches or exceeds the threshold of the sensitivity of an associated detection module.

The amplification module 1600 includes a flow member 1610 and a heater assembly 1630. The flow member 1610 defines a flow path 1620 through which a sample can flow from an inlet port 1621 to an outlet port 1622. The flow member 1610 defines a flow axis $A_F$ that indicates the overall direction of the flow through the flow member 1610. As described in more detail below, the flow path 1620 is shaped and/or has a geometry such that various portions of the flow path 1620 (e.g., a first portion 1624 and a second portion 1625) can be maintained at different temperatures by the heater assembly 1630. In this manner, the amplification module 1600 can perform a "flow through" polymerase chain reaction (PCR) on the sample to amplify the target organism and/or portions of a nucleic acid with within the sample. Although the flow path 1620 is shown as being a serpentine path (or a path that includes multiple switchbacks to reverse the flow of the sample), in other embodiments, the flow path can have any suitable shape and/or geometry.

The flow member 1610 (and any of the flow members described herein) can be constructed from any suitable material and can have any suitable dimensions to facilitate the desired amplification performance for the desired volume of sample. For example, in some embodiments, the amplification module 1600 (and any of the amplification modules described herein) can perform 1000× or greater amplification in a time of less than 15 minutes. For example, in some embodiments, the flow member 1610 (and any of the flow members described herein) is constructed from at least one of a cyclic olefin copolymer or a graphite-based material. Such materials facilitate the desired heat transfer properties into the flow path 1620. Moreover, in some embodiments, the flow member 1610 (and any of the flow members described herein) can have a thickness of less than about 0.5 mm. In some embodiments, the flow member 1610 (and any of the flow members described herein) can have a volume about 150 microliters or greater, and the flow can be such that at least 10 microliters of sample is amplified. In other embodiments, at least 20 microliters of sample are amplified by the methods and devices described herein. In other embodiments, at least 30 microliters of sample are amplified by the methods and devices described herein. In yet other embodiments, at least 50 microliters of sample are amplified by the methods and devices described herein.

The heater assembly 1630 includes a substrate 1640, a first heating element 1650, and a second heating element 1660, each coupled to the substrate 1640. As described herein, the heater assembly 1630 is coupled to the flow member 1610, and is configured to maintain various portions of the flow path 1620 at different temperature set points to facilitate the desired reaction. Thus, the substrate 1640 can be any suitable substrate, such as for example, an electrically isolative substrate to which the first heating element 1650 and second heating element 1660 are mounted. Moreover, the substrate 1640 (and any of the substrates described herein) can be constructed from any suitable material, such as, for example, a composite material including woven glass and epoxy. In some embodiments, the substrate 1640 (and any of the substrates described herein) can be constructed from a material having a glass transition temperature (Tg) of greater than about 170 C. In other embodiments, the substrate 1640 (and any of the substrates described herein) can be constructed from a material having a glass transition temperature (Tg) of greater than about 180 C (e.g., material 370HR produced by the Isola Group). In this manner, the substrate 1640 can maintain the desired rigidity and dimensional integrity to provide repeatable thermal performance for each channel of the flow path 1620.

As shown, the substrate 1640 defines an aperture 1641 (also referred to as an opening, cut-out, or via) that separates the substrate 1640 into a first portion 1631 and a second portion 1632. The first heating element 1650 is coupled to the first portion 1631, and the second heating element 1660 is coupled to the second portion 1632. In this manner, the aperture 1641 thermally isolates the first portion 1631 from the second portion 1632. Thus, by minimizing the heat transfer between the first portion 1631 and the second portion 1632, accuracy of the heat flow from the first heating element 1650 and the second heating element 1660 to the flow member 1610 can be improved. More particularly, the substrate 1640 is coupled to the flow member 1610 such that the first portion 1631 of the substrate 1640 is aligned with the first portion 1624 of the flow path 1620 and such that the second portion 1632 of the substrate 1640 is aligned with the second portion 1625 of the flow path 1620. This arrangement allows the first heating element 1650 to heat the first portion 1624 of the flow path 1620, and the second heating element 1660 to heat the second portion 1625 of the flow path 1620.

In use, the first heating element 1650 produces a first thermal output $Q_1$ to maintain the first portion 1624 of the flow path 1620 at a first temperature. The first temperature can be, for example, between about 100 C and about 115 C (to heat the sample to about 90 C; e.g., the "hot" temperature for a PCR thermal cycle). The second heating element 1660 produces a second thermal output $Q_2$ that is different from the first thermal output $Q_1$, and that can maintain the second portion 1625 of the flow path 1620 at a second temperature. The second temperature can be, for example, between about 60 C and about 75 C (to heat the sample to about 60 C; e.g., the "cold" temperature for a PCR thermal cycle). In this manner, the heater assembly 1630 and the flow member 1610 can establish multiple temperature zones through which a sample can flow, and can define a desired number of amplification cycles to ensure the desired test sensitivity (e.g., at least 30 cycles, at least 34 cycles, at least 36 cycles, at least 38 cycles, or at least 40 cycles).

In some embodiments, the sample flowing within the flow path 1620 is rapidly heated to about 90 C. To promote a rapid cooling down to about 60 C, in some embodiments, heat must flow out of the sample (and thus the flow member 1610). Thus, although the second thermal output $Q_2$ is shown as flowing into the flow path 1620 and/or the flow member 1610, in other embodiments, the second thermal output produced by the second heating element (or any of the heating elements described herein) can be such that the second thermal output $Q_2$ flows out of the flow path 1620 and/or the flow member 1610 towards the second heating element 1660. In such embodiments, a current can still be supplied to the second heating element 1660 to control the magnitude of the heat flow. In some embodiments, the second temperature can be, for example, between about 40 C and about 45 C (to allow heat transfer away from the sample at a controlled rate to facilitate maintaining the sample at about 60 C; e.g., the "cold" temperature for a PCR thermal cycle).

The aperture 1641 defined by the substrate 1640 can be of any suitable size and/or shape to facilitate thermal isolation of the first portion 1631 of the substrate 1640 and the second portion 1632 of the substrate 1640. For example, as shown in FIG. 1, the aperture 1641 can be an elongated opening that extends (or is elongated) along the overall direction of flow, as indicated by the flow axis $A_F$. In other embodiments, however, the aperture 1641 or portions thereof can be aligned with the channels of the flow path 1620. Similarly stated, in some embodiments, the aperture 1641 need not be a linear aperture, but can instead have multiple sections that are lateral to the flow axis $A_F$. In yet other embodiments, the aperture 1641 can be one of a series of openings, cut-outs, or slots that collectively thermally isolate the first portion 1631 of the substrate 1640 from the second portion 1632 of the substrate 1640. In still other embodiments, the aperture 1641 need not be a through-opening, but rather can be a blind opening that does not extend entirely through the substrate 1640.

The first heating element 1650 and the second heating element 1660 can be any suitable heating element or collection of heaters that can perform the functions described herein. For example, in some embodiments, the first heating element 1650 and the second heating element 1660 can each be single heating element that is thermally coupled to the flow member 1610, and that can cycle through multiple temperatures set points (e.g., between about 60 C and about 90 C). Moreover, the first heating element 1650 and the second heating element 1660 can be of any suitable design. For example, in some embodiments, the first heating element 1650 and the second heating element 1660 can be a resistance heater, a thermoelectric device (e.g. a Peltier device), or the like. In some embodiments, the first heating element 1650 and the second heating element 1660 can be resistance heaters that are lithographically produced on or within the substrate 1640.

The flow member 1610 can be coupled to the heater assembly 1630 in any suitable manner. For example, in some embodiments, the flow member 1610 can be coupled to the heater assembly 1630 by a series of mechanical fasteners, such as clamps, screws, or the like. In some such embodiments, the fasteners can also function as heat sinks to allow accurate control of the temperatures of the flow member 1610 and to avoid overheating. In other embodiments, the flow member 1610 can be coupled to the heater assembly 1630 by an adhesive (e.g., a pressure-sensitive adhesive). Similarly stated, in some embodiments, the flow member 1610 can be chemically bonded to the heater assembly 1630. In yet other embodiments, the flow member 1610 can be coupled to the heater assembly 1630 by an adhesive (e.g., a pressure-sensitive adhesive) and mechanical fasteners can be used to couple other structure and function as a heat sink. In this manner, the flow member 1610 is fixedly coupled to the heater assembly 1630. Said another way, in some embodiments, the flow member 1610 is not designed to be removed and/or decoupled from the heater assembly 1630 during normal use (i.e., the flow member 1610 is irreversibly coupled to the heater assembly 1630 and/or the substrate 1640). This arrangement facilitates a single-use, disposable device that includes the amplification module 1600.

Figure 2:
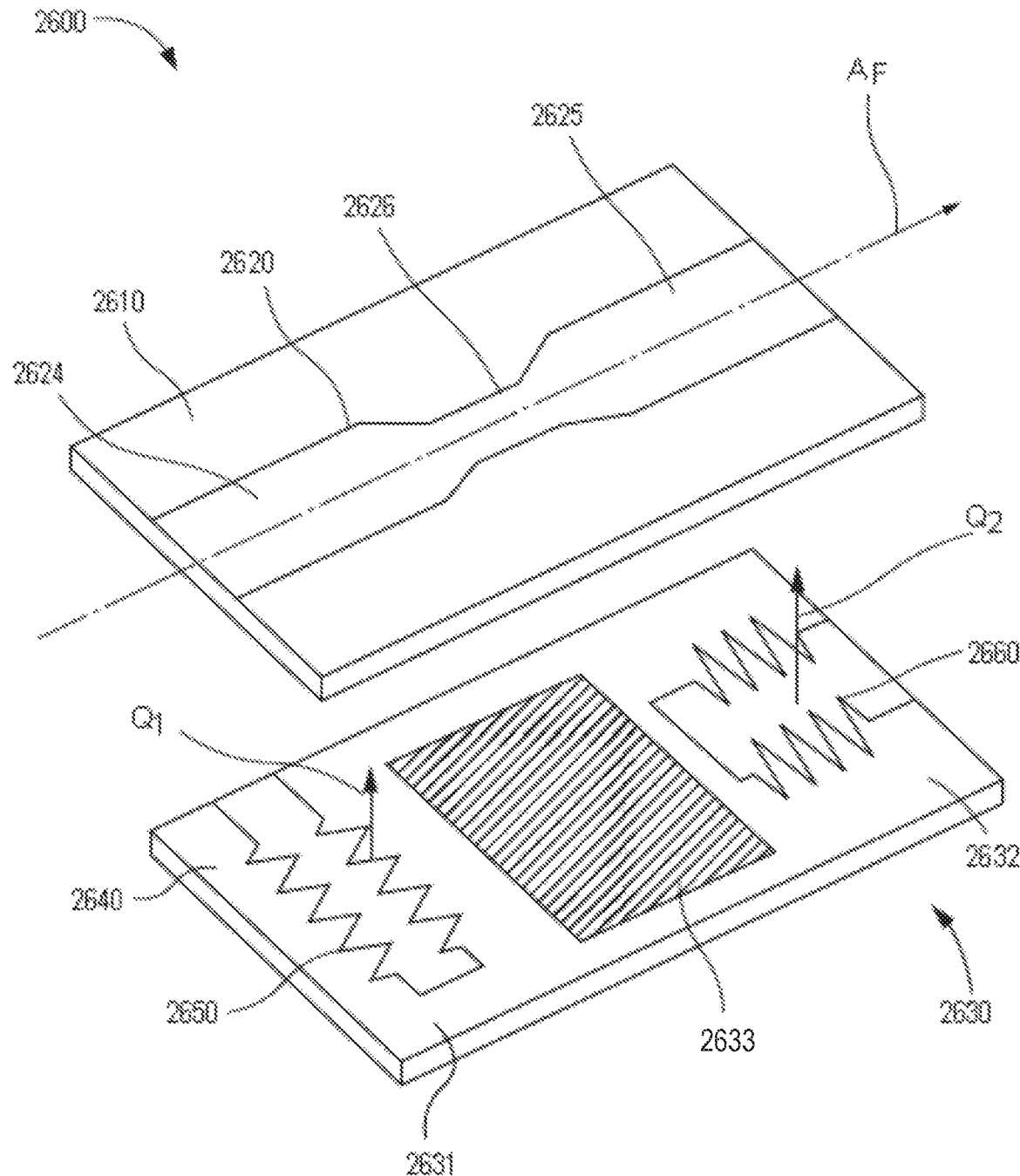
FIG. 2 is a perspective view schematic illustration of a thermal reaction module, according to an embodiment.

Although the substrate 1640 is shown as defining an aperture 1641, in some embodiments, an amplification module can include a substrate that does not define an aperture that separates heaters mounted thereto. Moreover, although the flow member 1610 is shown as defining a serpentine flow path 1620, in other embodiments, an amplification module can include any suitably-shaped flow path. For example, FIG. 2 is a schematic illustration of an amplification (or thermal reaction) module 2600, according to an embodiment. The amplification module 2600 is configured to perform a thermal reaction (e.g., an amplification reaction) on an input of target nucleic acid mixed with required reagents, and can be included in any suitable diagnostic device. For example, the amplification module can be included in any of the diagnostic devices shown and described herein (including the device 6000 and the device 7000) or in International Patent Publication No. WO2016/109691, entitled "Devices and Methods for Molecular Diagnostic Testing," which is incorporated herein by reference in its entirety. In some embodiments, the amplification module 2600 is configured to conduct rapid amplification of an input target. In some embodiments, the amplification module 2600 is configured to generate an output copy number that reaches or exceeds the threshold of the sensitivity of an associated detection module.

The amplification module 2600 includes a flow member 2610 and a heater assembly 2630. The flow member 2610 defines a flow path 2620 through which a sample can flow from an inlet port to an outlet port. The flow member 2610 defines a flow axis $A_F$ that indicates the overall direction of the flow through the flow member 2610. The flow path 2620 includes a first portion 2624, a second portion 2625, and a third portion 2626. Similarly stated, the walls of the flow member define the first portion 2624, the second portion 2625, and the third portion 2626, which collectively form the flow path 2620. As described herein, the various portions of the flow path 2620 can be maintained at different temperatures by the heater assembly 2630. In this manner, the amplification module 2600 can perform a variety of thermally-based operations on a sample within the flow member 2610. For example, in some embodiments, a sample within the flow member 2610 can be repeatedly moved between the first portion 2624 and the second portion 2625 to thermally cycle the sample. In this manner, the amplification module 2600 can be used to perform a polymerase chain reaction (PCR) on the sample to amplify a target organism and/or portions of a nucleic acid with within the sample. In other embodiments, a sample within the flow member 2610 can be maintained at a substantially constant temperature within the first portion 2624 and/or the second portion 2625 to perform an isothermal amplification process to amplify a target organism and/or portions of a nucleic acid with within the sample. In yet other embodiments, a sample within the flow member 2610 can be maintained at a first temperature within the first portion 2624 and a second temperature with the second portion 2625. In this manner, the amplification module 2600 can be used to perform multiple operations on the sample (e.g., a lysing and/or inactivation operation within the first portion 2624 followed by an isothermal amplification operation within the second portion 2625). Although the flow path 2620 is shown as being substantially linear, in other embodiments, the flow path can have any suitable shape and/or geometry.

The flow member 2610 (and any of the flow members described herein) can be constructed from any suitable material and can have any suitable dimensions to facilitate the desired amplification performance for the desired volume of sample. For example, in some embodiments, the amplification module 2600 (and any of the amplification modules described herein) can perform 1000× or greater amplification in a time of less than 15 minutes. For example, in some embodiments, the flow member 2610 (and any of the flow members described herein) is constructed from at least one of a cyclic olefin copolymer or a graphite-based material. Such materials facilitate the desired heat transfer properties into the flow path 2620. Moreover, in some embodiments, the flow member 2610 (and any of the flow members described herein) can have a thickness of less than about 0.5 mm. In some embodiments, the flow member 2610 (and any of the flow members described herein) can have a volume about 150 microliters or greater, and the flow can be such that at least 10 microliters of sample is amplified. In other embodiments, at least 20 microliters of sample are amplified by the methods and devices described herein. In other embodiments, at least 30 microliters of sample are amplified by the methods and devices described herein. In yet other embodiments, at least 50 microliters of sample are amplified by the methods and devices described herein.

The heater assembly 2630 includes a substrate 2640, a first heating element 2650, and a second heating element 2660 each coupled to the substrate 2640. As described herein, the heater assembly 2630 can be coupled to the flow member 2610, and is configured to maintain various portions of the flow path 2620 at different temperature set points to facilitate the desired reaction (e.g., a thermal cycling amplification, an isotherm amplification, a lysis reaction, or the like). Thus, the substrate 2640 can be any suitable substrate, such as for example, an electrically isolative substrate to which the first heating element 2650 and second heating element 2660 are mounted. Moreover, the substrate 2640 (and any of the substrates described herein) can be constructed from any suitable material, such as, for example, a composite material including woven glass and epoxy. In some embodiments, the substrate 2640 (and any of the substrates described herein) can be constructed from a material having a glass transition temperature (Tg) of greater than about 170 C. In other embodiments, the substrate 2640 (and any of the substrates described herein) can be constructed from a material having a glass transition temperature (Tg) of greater than about 180 C (e.g., material 370HR produced by the Isola Group). In this manner, the substrate 2640 can maintain the desired rigidity and dimensional integrity to provide repeatable thermal performance for each portion of the flow path 2620.

In some embodiments, the heater assembly 2630 and the substrate 2640 (and any of the heater assemblies and substrates described herein) can be a portion of a printed circuit board of a molecular diagnostics device (e.g., any of the devices described herein, including the device 6000 and the device 7000). Thus, the substrate 2640 can also support and/or be coupled to electronic components that form the circuitry to control the heater assembly 2630 as well as the overall diagnostic device (e.g., flow pumps, introduction of reagents, sample preparation operations, or the like). For example, in some embodiments, the substrate 2640 (and any of the substrates or printed circuit board layers described herein) can be coupled to and/or support a processor, a controller, or the like. In this manner, the heater assembly 2630 and the substrate 2640 (and any of the heater assemblies and substrates described herein) can be a portion of a printed circuit board that performs many different electronic functions, including controlling the amplification of the sample, controlling sample movement, and other thermally-based functions described herein.

As shown, the substrate 2640 includes a first portion 2631, a second portion 2632, and a third portion 2633. The third portion 2633 is between the first portion 2631 and the second portion 2632. Similarly stated, the third portion 2633 separates the first portion 2631 and the second portion 2632. The first heating element 2650 is coupled to the first portion 2631 of the substrate 2640 and can produce a first thermal output $Q_1$. The second heating element 2660 is coupled to the second portion 2632 of the substrate 2640 and can produce a second thermal output $Q_2$. In some embodiments, the substrate 2640 can be coupled to the flow member 2610 such that the first portion 2631 of the substrate 2640 (and the first heating element 2650) is aligned with the first portion 2624 of the flow path 2620 and the second portion 2632 of the substrate 2640 (and the second heating element 2660) is aligned with the second portion 2625 of the flow path 2620. This arrangement allows the first heating element 2650 to heat the first portion 2624 of the flow path 2620, and the second heating element 2660 to heat the second portion 2625 of the flow path 2620, as described herein.

The first portion 2631 of the substrate 2640 is characterized by a first thermal conductivity, the second portion 2632 of the substrate 2640 is characterized by a second thermal conductivity, and the third portion 2633 of the substrate 2640 is characterized by a third thermal conductivity. The third thermal conductivity is less than the first thermal conductivity and the second thermal conductivity. In this manner, heat transfer within the substrate 2640 between the first portion 2631 and the second portion 2632 is limited. Similarly stated, the difference in the thermal conductivity between the third portion 2633 and the other two portions (i.e., the first portion 2631 and the second portion 2632) is such that the third portion 2633 thermally isolates the first portion 2631 from the second portion 2632. By minimizing the heat transfer between the first portion 2631 and the second portion 2632, accuracy of the heat flow from the first heating element 2650 and the second heating element 2660 to the flow member 2610 can be improved.

In some embodiments, the third portion 2633 of the substrate 2640 can be constructed from a different material from which either of the first portion 2631 of the substrate 2640 or the second portion 2632 of the substrate 2640 are constructed. For example, in some embodiments, the first portion 2631 of the substrate 2640 and the second portion 2632 of the substrate 2640 are constructed from a composite material including woven glass and epoxy, including, for example, an FR-4 grade material. Such materials can have a thermal conductivity of between about 0.5 W/m-K and about 1.0 W/m-K. In contrast the third portion 2633 of the substrate 2640 can be constructed from or include a material having a lower thermal conductivity. For example, in some embodiments, the third portion 2633 of the substrate 2640 can be constructed from or include a material having a thermal conductivity of about 0.1 W/m-K or less. In other embodiments, the third portion 2633 of the substrate 2640 can be constructed from or include a material having a thermal conductivity of about 0.05 W/m-K or less. For example, in some embodiments, the third portion 2633 of the substrate 2640 (or any other insulative substrate portions described herein) can be constructed from or include a rigid foam (e.g., polyurethane foam, a silicon foam, a neoprene foam, a vinyl foam, or the like). In other embodiments, the third portion 2633 of the substrate 2640 (or any other insulative substrate portions described herein) can be constructed from or include a low thermal conductivity polymer or composite material.

The third portion 2633 of the substrate 2640 can provide a lower thermal conductivity (or higher thermal resistance) than that of either of the first portion 2631 of the substrate 2640 or the second portion 2632 of the substrate 2640 along any axis. For example, in some embodiment, the third portion 2633 of the substrate 2640 can have a lower "in plane" thermal conductivity (or higher "in plane" thermal resistance) than that of either of the first portion 2631 of the substrate 2640 or the second portion 2632 of the substrate 2640. In this manner, the heat flow between the first portion 2631 of the substrate 2640 and the second portion 2632 of the substrate 2640 within the planar surface to which the heating elements are coupled is limited.

Moreover, although the first portion 2631 of the substrate 2640, the second portion 2632 of the substrate 2640, and the third portion 2633 of the substrate 2640 are shown as defining a planar surface to which the flow member 2610 is coupled, in other embodiments, the top surface of the substrate 2640 and/or heater assembly 2630 need not be planar. In other embodiments, for example, the top surface of the substrate 2640 can include multiple different levels and/or discontinuous portions.

In some embodiments, the third portion 2633 of the substrate 2640 can define one or more apertures or openings (not shown in FIG. 2) to decrease the thermal conductivity (or increase the thermal resistance) of the third portion 2633. For example, in some embodiments, the third portion 2633 of the substrate 2640 (or any other substrate portions described herein) can include a series of perforations. Such perforations can either extend through the substrate (i.e., "through holes") or can extend only partially through the substrate. Moreover, in those embodiments in which the third portion 2633 of the substrate 2640 defines one or more apertures, the substrate 2640 (or any of the substrates described herein) can include one or more connection portions to maintain the desired structural rigidity of the third portion 2633.

The first heating element 2650 and the second heating element 2660 can be any suitable heating element or collection of heaters that can perform the functions described herein. For example, in some embodiments, the first heating element 2650 and the second heating element 2660 can each be single heating element that is thermally coupled to the flow member 2610, and that can cycle through multiple temperatures set points (e.g., between about 60 C and about 90 C). Moreover, the first heating element 2650 and the second heating element 2660 can be of any suitable design. For example, in some embodiments, the first heating element 2650 and the second heating element 2660 can be a resistance heater, a thermoelectric device (e.g. a Peltier device), or the like. In some embodiments, the first heating element 2650 and the second heating element 2660 can be resistance heaters that are lithographically produced on or within the substrate 2640.

The flow member 2610 can be coupled to the heater assembly 2630 in any suitable manner. For example, in some embodiments, the flow member 2610 can be coupled to the heater assembly 2630 by a series of mechanical fasteners, such as clamps, screws, or the like. In some such embodiments, the fasteners can also function as heat sinks to allow accurate control of the temperatures of the flow member 2610 and to avoid overheating. In other embodiments, the flow member 2610 can be coupled to the heater assembly 2630 by an adhesive (e.g., a pressure-sensitive adhesive). Similarly stated, in some embodiments, the flow member 2610 can be chemically bonded to the heater assembly 2630. In yet other embodiments, the flow member 2610 can be coupled to the heater assembly 2630 by an adhesive (e.g., a pressure-sensitive adhesive) and mechanical fasteners can be used to couple other structure and function as a heat sink. In this manner, the flow member 2610 is fixedly coupled to the heater assembly 2630. Said another way, in some embodiments, the flow member 2610 is not designed to be removed and/or decoupled from the heater assembly 2630 during normal use (i.e., the flow member 2610 is irreversibly coupled to the heater assembly 2630 and/or the substrate 2640). This arrangement facilitates a single-use, disposable device that includes the amplification module 2600.

In use, the first heating element 2650 produces a first thermal output $Q_1$ to maintain the first portion 2624 of the flow path 2620 (or the sample therein) at a first temperature. The first temperature can be, for example, between about 100 C and about 115 C (to heat the sample to about 90 C; e.g., the "hot" temperature for a PCR thermal cycle). The second heating element 2660 produces a second thermal output $Q_2$ that is different from the first thermal output $Q_1$, and that can maintain the second portion 2625 of the flow path 2620 at a second temperature. The second temperature can be, for example, between about 60 C and about 75 C (to heat the sample to about 60 C; e.g., the "cold" temperature for a PCR thermal cycle). In this manner, the heater assembly 2630 and the flow member 2610 can establish multiple temperature zones within which a sample can flow or be maintained.

In some embodiments, the sample flowing within the first portion 2624 flow path 2620 is rapidly heated to about 90 C. To promote a rapid cooling down to about 60 C, in some embodiments, heat must flow out of the sample (and thus the flow member 2610). Thus, although the second thermal output $Q_2$ is shown as flowing into the flow path 2620 and/or the flow member 2610, in other embodiments, the second thermal output produced by the second heating element (or any of the heating elements described herein) can be such that the second thermal output $Q_2$ flows out of the flow path 2620 and/or the flow member 2610 towards the second heating element 2660. In such embodiments, a current can still be supplied to the second heating element 2660 to control the magnitude of the heat flow. In some embodiments, the second temperature can be, for example, between about 40 C and about 45 C (to allow heat transfer away from the sample at a controlled rate to facilitate maintaining the sample at about 60 C; e.g., the "cold" temperature for a PCR thermal cycle).

In other embodiments, the first temperature can be maintained at a temperature suitable for cell lysis, and the second temperature can be maintained at a temperature suitable for an isothermal amplification operation. In this manner, the sample (and the nucleic acid(s) therein) can be prepared for amplification in the first portion 2624 of the flow path 2620, and then amplified in the second portion 2625 of the flow path 2620. In some embodiments, the amplification module 2600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

In other embodiments, any suitable thermal reaction can be conducted either of the first portion 2624 of the flow path 2620 or the second portion 2625 of the flow path 2620. For example, in some embodiments, the temperature of the first portion 2624 (or any of the flow path portions described herein) can be maintained to perform a hot-start on the sample therein, while the temperature of the second portion 2625 can be maintained or cycled to amplify the organisms therein. In other embodiments, either of the first portion 2624 of the flow path 2620 or the second portion 2625 of the flow path 2620 can be used to conduct a lysing reaction, an inactivation reaction, and/or a detection reaction.

Figure 3:
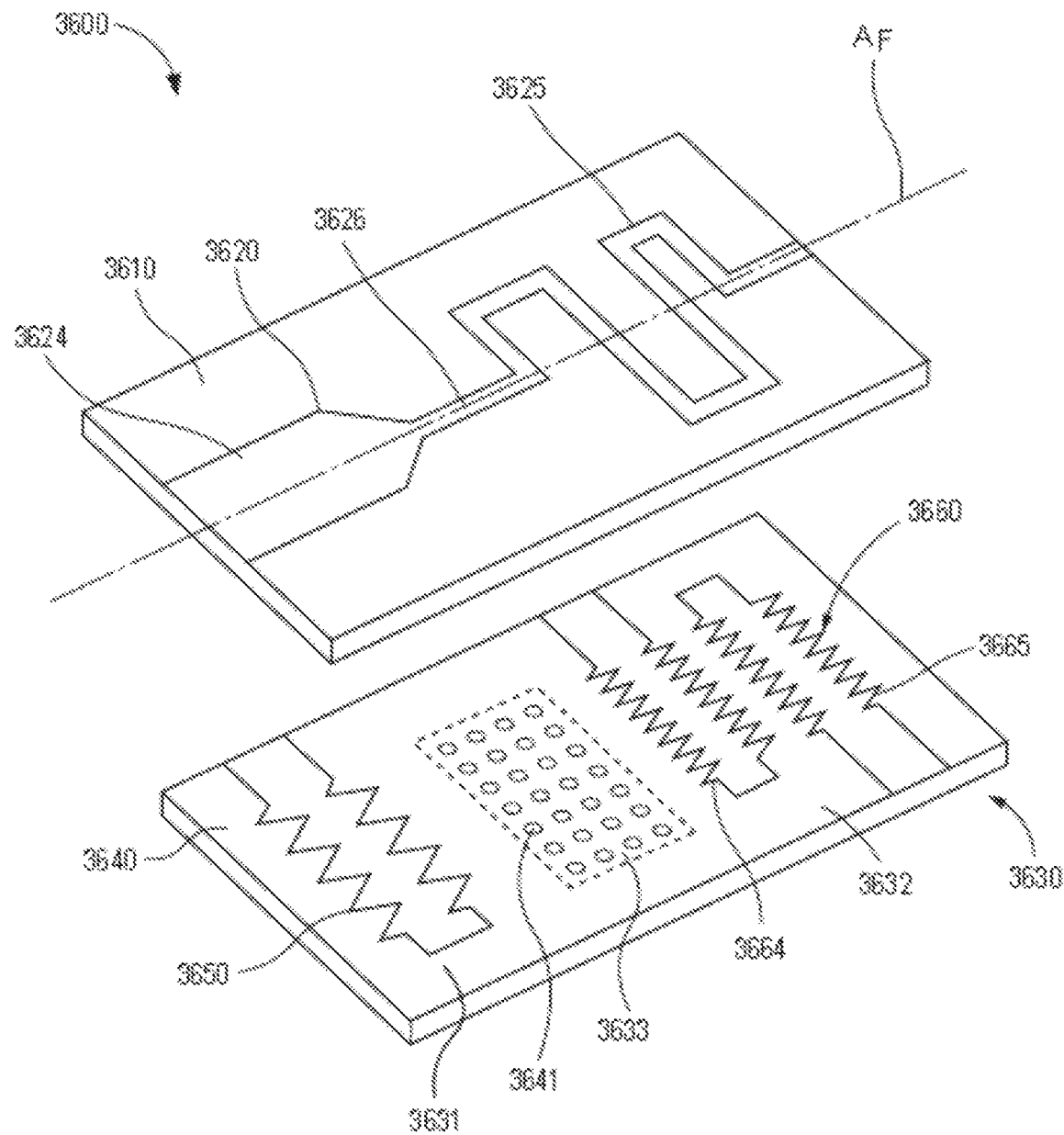
FIG. 3 is a perspective view schematic illustration of a thermal reaction module, according to an embodiment.

Although the substrate 2640 is shown as including one heating element coupled to (or within) the first portion 2631 of the substrate 2640 and a second heating element coupled to (or within) the second portion 2632 of the substrate 2640, in other embodiments, any number of heating elements can be coupled to any portion of a substrate. Moreover, in some embodiments, the heating elements can be electrically isolated from each other to allow for independent control of each heating element. For example, FIG. 3 is a schematic illustration of an amplification (or thermal reaction) module 3600, according to an embodiment. The amplification module 3600 is configured to perform a thermal reaction (e.g., an amplification reaction) on an input of target nucleic acid mixed with required reagents, and can be included in any suitable diagnostic device. For example, the amplification module can be included in any of the diagnostic devices shown and described herein (including the device 6000 and the device 7000) or in International Patent Publication No. WO2016/109691, entitled "Devices and Methods for Molecular Diagnostic Testing," which is incorporated herein by reference in its entirety. In some embodiments, the amplification module 3600 is configured to conduct rapid amplification of an input target. In some embodiments, the amplification module 3600 is configured to generate an output copy number that reaches or exceeds the threshold of the sensitivity of an associated detection module.

The amplification module 3600 includes a flow member 3610 and a heater assembly 3630. The flow member 3610 defines a flow path 3620 through which a sample can flow from an inlet port to an outlet port. The flow member 3610 defines a flow axis $A_F$ that indicates the overall direction of the flow through the flow member 3610. The flow path 3620 includes a first portion 3624, a second portion 3625, and a third portion 3626. Similarly stated, the walls of the flow member define the first portion 3624, the second portion 3625, and the third portion 3626, which collectively form the flow path 3620. As described herein, the various portions of the flow path 3620 can be maintained at different temperatures by the heater assembly 3630. In this manner, the amplification module 3600 can perform a variety of thermally-based operations on a sample within the flow member 3610. For example, in some embodiments, a sample the flow member 3610 can be maintained at a substantially constant temperature within the first portion 3624 and/or the second portion 3625 to perform an isothermal amplification process to amplify a target organism and/or portions of a nucleic acid with within the sample. In other embodiments, a sample within the flow member 3610 can be maintained at a first temperature within the first portion 3624 and a second temperature with the second portion 3625. In this manner, the amplification module 3600 can be used to perform multiple operations on the sample (e.g., a hot-start, a lysing and/or an inactivation operation within the first portion 3624 followed by an isothermal amplification operation within the second portion 3625). Although the first portion 3624 of the flow path 3620 is shown as being substantially linear and the second portion 3625 of the flow path 3620 is shown as including a series of switchbacks, in other embodiments, the flow path can have any suitable shape and/or geometry.

The flow member 3610 (and any of the flow members described herein) can be constructed from any suitable material and can have any suitable dimensions to facilitate the desired amplification performance for the desired volume of sample. For example, in some embodiments, the amplification module 3600 (and any of the amplification modules described herein) can perform 1000× or greater amplification in a time of less than 15 minutes. For example, in some embodiments, the flow member 3610 (and any of the flow members described herein) is constructed from at least one of a cyclic olefin copolymer or a graphite-based material. Such materials facilitate the desired heat transfer properties into the flow path 3620. Moreover, in some embodiments, the flow member 3610 (and any of the flow members described herein) can have a thickness of less than about 0.5 mm. In some embodiments, the flow member 3610 (and any of the flow members described herein) can have a volume about 150 microliters or greater, and the flow can be such that at least 10 microliters of sample is amplified. In other embodiments, at least 20 microliters of sample are amplified by the methods and devices described herein. In other embodiments, at least 30 microliters of sample are amplified by the methods and devices described herein. In yet other embodiments, at least 50 microliters of sample are amplified by the methods and devices described herein.

The heater assembly 3630 includes a substrate 3640, a first heating element assembly 3650, and a second heating element assembly 3660 each coupled to (or within) the substrate 3640. As described herein, the heater assembly 3630 can be coupled to the flow member 3610, and is configured to maintain various portions of the flow path 3620 at different temperature set points to facilitate the desired reaction (e.g., a thermal cycling amplification, an isotherm amplification, a lysis reaction, or the like). Thus, the substrate 3640 can be any suitable substrate, such as for example, an electrically isolative substrate to which the first heating element 3650 and second heating element 3660 are mounted. Moreover, the substrate 3640 (and any of the substrates described herein) can be constructed from any suitable material, such as, for example, a composite material including woven glass and epoxy. In some embodiments, the substrate 3640 (and any of the substrates described herein) can be constructed from a material having a glass transition temperature (Tg) of greater than about 170 C. In other embodiments, the substrate 3640 (and any of the substrates described herein) can be constructed from a material having a glass transition temperature (Tg) of greater than about 180 C (e.g., material 370HR produced by the Isola Group). In this manner, the substrate 3640 can maintain the desired rigidity and dimensional integrity to provide repeatable thermal performance for each portion of the flow path 3620.

In some embodiments, the heater assembly 3630 and substrate 3640 (and any of the heater assemblies and substrates described herein) can be a portion of a printed circuit board of a molecular diagnostics device (e.g., any of the devices described herein, including the device 6000 or the device 7000). Thus, the substrate 3640 can also support and/or be coupled to electronic components that form the circuitry to control the heater assembly 3630 as well as the overall diagnostic device (e.g., flow pumps, introduction of reagents, sample preparation operations, or the like). For example, in some embodiments, the substrate 3640 (and any of the substrates or printed circuit board layers described herein) can be coupled to and/or support a processor, a controller, or the like. In this manner, the heater assembly 3630 and the substrate 3640 (and any of the heater assemblies and substrates described herein) can be a portion of a printed circuit board that performs many different electronic functions, including controlling the amplification of the sample, controlling sample movement, and other thermally-based functions described herein.

As shown, the substrate 3640 includes a first portion 3631, a second portion 3632, and a third portion 3633. The third portion 3633 is between the first portion 3631 and the second portion 3632. Similarly stated, the third portion 3633 separates the first portion 3631 and the second portion 3632. The first heating element assembly 3650 is coupled to the first portion 3631 of the substrate 3640 and can produce a first thermal output. The second heating element assembly 3660 is coupled to the second portion 3632 of the substrate 3640 and can produce a second thermal output. In some embodiments, the substrate 3640 can be coupled to the flow member 3610 such that the first portion 3631 of the substrate 3640 (and the first heating element assembly 3650) is aligned with the first portion 3624 of the flow path 3620 and the second portion 3632 of the substrate 3640 (and the second heating element assembly 3660) is aligned with the second portion 3625 of the flow path 3620. This arrangement allows the first heating element assembly 3650 to heat the first portion 3624 of the flow path 3620, and the second heating element assembly 3660 to heat the second portion 3625 of the flow path 3620, as described herein.

The third portion 3633 of the substrate 3640 defines a series of apertures 3641. Thus, the thermal conductivity (e.g., the thermal conductivity within the plane of the surface to which the heaters are coupled) of the third portion 3633 of the substrate 3640 is impacted by the shape, size and pattern of the apertures 3641. Because air has a thermal conductivity of between about 0.01 W/m-K and 0.03 W/m-K and a material from which the substrate 3640 is fabricated (e.g., an FR-4 grade printed circuit board material) can have a thermal conductivity of between about 0.5 W/m-K and about 1.0 W/m-K, the inclusion of the apertures 3641 can result in the third portion 3633 of the substrate 3640 having a thermal conductivity less than that of the first portion 3631 of the substrate 3640 and the second portion 3632 of the substrate 3640. In this manner, heat transfer within the substrate 3640 between the first portion 3631 and the second portion 3632 is limited. By minimizing the heat transfer between the first portion 3631 and the second portion 3632, accuracy of the heat flow from the first heating element 3650 and the second heating element 3660 to the flow member 3610 can be improved.

The first heating element assembly 3650 is aligned with the first portion 3624 of the flow path 3620, and thus can maintain the first portion 3624 of the flow path 3620 at a first temperature. The first heating element assembly 3650 can include one or more individual heating elements (only one heating element is shown in FIG. 3). The second heating element assembly 3660 is aligned with the second portion 3625 of the flow path 3620, and thus can maintain the second portion 3625 of the flow path 3620 at a second temperature. The second heating element assembly 3660 can include one or more individual heating elements. Specifically, the second heating element assembly 3660 includes a first element 3664 and a second element 3665 that is electrically isolated from the first element 3664. In this manner, an electrical current can be conveyed to the first element 3664 independently from an electrical current conveyed to the second element 3665. Similarly stated, this arrangement allows for independent control of the first element 3664 and the second element 3665.

As shown in FIG. 3, the elements of the second heating element assembly 3660 are each aligned along the flow axis $A_F$. Similarly stated, the second heating element assembly 3660 is segmented along the flow axis $A_F$. This arrangement, along with the independent control of the elements of the second heating element assembly 3660 allow for accurate control of heat flow to the portions of the flow path 3620. For example, in some embodiments, the first element 3664 of the second heating element assembly 3660 can be aligned with (and/or beneath) a first channel of the second portion 3625 of the flow path 3620. The second element 3665 of the second heating element assembly 3660 can be aligned with (and/or beneath) a second (or last) channel of the second portion 3625 of the flow path 3620. The segmented, independently controllable design allows the first element 3664 to produce a first thermal output and the second element 3665 to produce a second thermal output that is different from the first thermal output. By producing different thermal outputs, the first channel and the second (or last) channel can be more accurately maintained at the desired temperature. For example, in some embodiments, the thermal design of the diagnostic device may result in greater heat transfer away from the second (or last) channel of the flow path 3620 (e.g., due to adjacent structures, internal air movement that increases convection transfer, or the like). In such situations, the second element 3665 can be controlled to provide a greater thermal output, thereby maintaining a consistent temperature between the first channel and the last channel. This, in turn, increases the overall accuracy of the device.

Thus, the heater assembly 3630 and the flow member 3610 can establish multiple temperature zones through which a sample can flow and/or be contained. Although the second heating element assembly 3660 is shown as including two independent heating elements, in other embodiments, each of the first heating element assembly 3650 and the second heating element assembly 3660 can include any number of independent heating elements (e.g. three elements, four elements, or more). Although the second heating element assembly 3660 is shown as being aligned with the flow axis $A_F$, in other embodiments, each of the first heating element assembly 3650 and the second heating element assembly 3660 can have any suitable alignment. For example, in some embodiments, a heating element assembly can be aligned with the flow channels. In some embodiments, a heating element assembly can include an element that extends beyond the flow path defined by a flow member (e.g., to minimize the effects of heat "roll off" on an end channel of the flow path).

The heating elements can be any suitable heating element or collection of heaters that can perform the functions described herein. For example, in some embodiments, any of the heating elements can be a single heating element that is thermally coupled to the flow member 3610, and that can cycle through multiple temperatures set points (e.g., between about 60 C and about 90 C). Moreover, any of the heating elements can be of any suitable design. For example, in some embodiments, any of the heating elements can be a resistance heater, a thermoelectric device (e.g. a Peltier device), or the like. In some embodiments, any of the heating elements can be resistance heaters that are lithographically produced on the substrate 3640.

The flow member 3610 can be coupled to the heater assembly 3630 in any suitable manner. For example, in some embodiments, the flow member 3610 can be coupled to the heater assembly 3630 by a series of mechanical fasteners, such as clamps, screws, or the like. In some such embodiments, the fasteners can also function as heat sinks to allow accurate control of the temperatures of the flow member 3610 and to avoid overheating. In other embodiments, the flow member 3610 can be coupled to the heater assembly 3630 by an adhesive (e.g., a pressure-sensitive adhesive). Similarly stated, in some embodiments, the flow member 3610 can be chemically bonded to the heater assembly 3630. In yet other embodiments, the flow member 3610 can be coupled to the heater assembly 3630 by an adhesive (e.g., a pressure-sensitive adhesive) and mechanical fasteners can be used to couple other structure and function as a heat sink.

In this manner, the flow member 3610 is fixedly coupled to the heater assembly 3630. Said another way, in some embodiments, the flow member 3610 is not designed to be removed and/or decoupled from the heater assembly 3630 during normal use (i.e., the flow member 3610 is irreversibly coupled to the heater assembly 3630 and/or the substrate 3640). This arrangement facilitates a single-use, disposable device that includes the amplification module 3600.

In use, the first heating element assembly 3650 produces a first thermal output to maintain the first portion 3624 of the flow path 3620 (or the sample therein) at a first temperature. The first temperature can be, for example, between about 100 C and about 115 C (to heat the sample to about 90 C; e.g., the "hot" temperature for a PCR thermal cycle). The second heating element assembly 3660 produces a second thermal output that is different from the first thermal output, and that can also be different between the first element 3664 and the second element 3665. The second thermal output can maintain the second portion 3625 of the flow path 3620 at a second temperature. The second temperature can be, for example, between about 60 C and about 75 C (to heat the sample to about 60 C; e.g., the "cold" temperature for a PCR thermal cycle). In this manner, the heater assembly 3630 and the flow member 3610 can establish multiple temperature zones within which a sample can flow or be maintained. In other embodiments, the first temperature can be maintained at a temperature suitable for cell lysis, and the second temperature can be maintained at a temperature suitable for an isothermal amplification operation. In this manner, the sample (and the nucleic acid(s) therein) can be prepared for amplification in the first portion 3624 of the flow path 3620, and then amplified in the second portion 3625 of the flow path 3620.

In some embodiments, the sample flowing within the flow path 3620 is rapidly heated to about 90 C. To promote a rapid cooling down to about 60 C, in some embodiments, heat must flow out of the sample (and thus the flow member 3610). Thus, although the second temperature is described as being hotter than the desired sample temperature, in other embodiments, the output produced by the second heating element assembly 3660 (or any of the heating elements described herein) can be such that heat flows out of the flow path 3620 and/or the flow member 3610. In such embodiments, a current can still be supplied to the second heating element assembly 3660 to control the magnitude of the heat flow. In some embodiments, the second temperature can be, for example, between about 40 C and about 45 C (to allow heat transfer away from the sample at a controlled rate to facilitate maintaining the sample at about 60 C; e.g., the "cold" temperature for a PCR thermal cycle).

In some embodiments, the amplification module 3600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

In other embodiments, any suitable thermal reaction can be conducted either of the first portion 3624 of the flow path 3620 or the second portion 3625 of the flow path 3620. For example, in some embodiments, the temperature of the first portion 3624 (or any of the flow path portions described herein) can be maintained to perform a hot-start on the sample therein, while the temperature of the second portion 3625 can be maintained or cycled to amplify the organisms therein. In other embodiments, either of the first portion 3624 of the flow path 3620 or the second portion 3625 of the flow path 3620 can be used to conduct a lysing reaction, an inactivation reaction, and/or a detection reaction.

Figure 4:
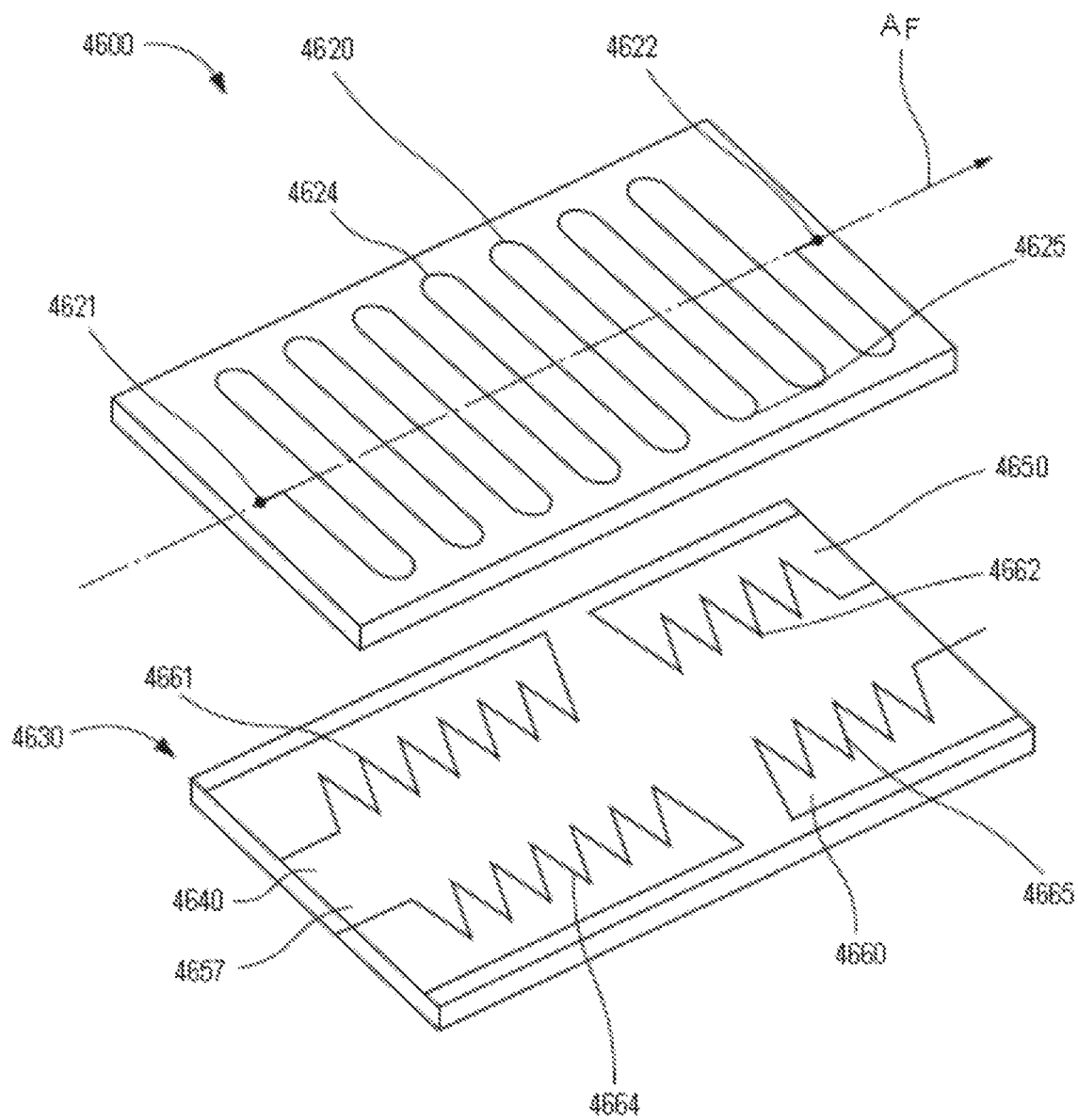
FIG. 4 is a perspective view schematic illustration of a thermal reaction module, according to an embodiment.

Although the substrate 1640 and the substrate 3640 are shown as defining one or more apertures (aperture 1641 and the apertures 3641, respectively), in some embodiments, an amplification module can include a substrate that does not define an aperture that separates heaters mounted thereto. For example, FIG. 4 is a schematic illustration of an amplification (or thermal reaction) module 4600, according to an embodiment. The amplification module 4600 is configured to perform a thermal reaction (e.g., an amplification reaction) on an input of target nucleic acid mixed with required reagents, and can be included in any suitable diagnostic device. For example, the amplification module can be included in any of the diagnostic devices shown and described herein (including the device 6000 and the device 7000) or in International Patent Publication No. WO2016/109691, entitled "Devices and Methods for Molecular Diagnostic Testing," which is incorporated herein by reference in its entirety. In some embodiments, the amplification module 4600 is configured to conduct rapid amplification of an input target. In some embodiments, the amplification module 4600 is configured to generate an output copy number that reaches or exceeds the threshold of the sensitivity of an associated detection module.

The amplification module 4600 includes a flow member 4610 and a heater assembly 4630. The flow member 4610 defines a flow path 4620 through which a sample can flow from an inlet port 4621 to an outlet port 4622. The flow member 4610 defines a flow axis $A_F$ that indicates the overall direction of the flow through the flow member 4610. The flow path 4620 is shaped and/or has a geometry such that various portions of the flow path 4620 (e.g., a first portion 4624 and a second portion 4625) can be maintained at different temperatures by the heater assembly 4630. In this manner, the amplification module 4600 can perform a "flow through" polymerase chain reaction (PCR) on the sample to amplify the target organism and/or portions of the DNA of the organism within the sample. Although the flow path 4620 is shown as being a serpentine path (or a path that includes multiple switchbacks to reverse the flow of the sample), in other embodiments, the flow path can have any suitable shape and/or geometry.

The flow member 4610 (and any of the flow members described herein) can be constructed from any suitable material and can have any suitable dimensions to facilitate the desired amplification performance for the desired volume of sample. For example, in some embodiments, the amplification module 4600 (and any of the amplification modules described herein) can perform 1000× or greater amplification in a time of less than 15 minutes. For example, in some embodiments, the flow member 4610 (and any of the flow members described herein) is constructed from at least one of a cyclic olefin copolymer or a graphite-based material. Such materials facilitate the desired heat transfer properties into the flow path 1620. Moreover, in some embodiments, the flow member 4610 (and any of the flow members described herein) can have a thickness of less than about 0.5 mm. In some embodiments, the flow member 1610 (and any of the flow members described herein) can have a volume about 150 microliters or greater, and the flow can be such that at least 10 microliters of sample is amplified. In other embodiments, at least 20 microliters of sample are amplified by the methods and devices described herein. In other embodiments, at least 30 microliters of sample are amplified by the methods and devices described herein. In yet other embodiments, at least 50 microliters of sample are amplified by the methods and devices described herein.

The heater assembly 4630 includes a substrate 4640, a first heating element assembly 4650, and a second heating element assembly 4660, each heating element assembly being coupled to the substrate 4640. As described herein, the first heating element assembly 4650 and the second heating element assembly 4660 are each coupled between a first side 4657 of the substrate 4640 and the flow member 4610. In this manner, the heater assembly 4630 is configured to maintain various portions of the flow path 4620 at different temperature set points to facilitate the desired reaction (e.g., a thermal cycling amplification, an isotherm amplification, a lysis reaction, or the like). The substrate 4640 can be any suitable substrate, such as for example, an electrically isolative substrate to which the first heating element assembly 4650 and second heating element assembly 4660 are mounted. The substrate 4640 (and any of the substrates described herein) can be constructed from any suitable material, such as, for example, a composite material including woven glass and epoxy. In some embodiments, the substrate 4640 (and any of the substrates described herein) can be constructed from a material having a glass transition temperature (Tg) of greater than about 170 C. In other embodiments, the substrate 4640 (and any of the substrates described herein) can be constructed from a material having a glass transition temperature (Tg) of greater than about 180 C (e.g., material 370HR produced by the Isola Group). In this manner, the substrate 4640 can maintain the desired rigidity and dimensional integrity to provide repeatable thermal performance for each channel of the flow path 4620.

In some embodiments, the heater assembly 4630 and the substrate 4640 (and any of the heater assemblies and substrates described herein) can be a portion of a printed circuit board of a molecular diagnostics device (e.g., any of the devices described herein, including the device 6000 or the device 7000). Thus, the substrate 4640 can also support and/or be coupled to electronic components that form the circuitry to control the heater assembly 4630 as well as the overall diagnostic device (e.g., flow pumps, introduction of reagents, sample preparation operations, or the like). For example, in some embodiments, the substrate 4640 (and any of the substrates or printed circuit board layers described herein) can be coupled to and/or support a processor, a controller, or the like. In this manner, the heater assembly 4630 and the substrate 4640 (and any of the heater assemblies and substrates described herein) can be a portion of a printed circuit board that performs many different electronic functions, including controlling the amplification of the sample, controlling sample movement, and other thermally-based functions described herein.

The first heating element assembly 4650 is aligned with the first portion 4624 of the flow path 4620, and thus can maintain the first portion 4624 of the flow path 4620 at a first temperature. The first temperature can be, for example, between about 100 C and about 115 C (to heat the sample to about 90 C; e.g., the "hot" temperature for a PCR thermal cycle). The first heating element assembly 4650 includes a first element 4661 and a second element 4662 that is electrically isolated from the first element 4661. In this manner, an electrical current can be conveyed to the first element 4661 independently from an electrical current conveyed to the second element 4662. Similarly stated, this arrangement allows for independent control of the first element 4661 and the second element 4662.

The second heating element assembly 4660 is aligned with the second portion 4625 of the flow path 4620, and thus can maintain the second portion 4625 of the flow path 4620 at a second temperature. The second temperature can be, for example, between about 60 C and about 75 C (to heat the sample to about 60 C; e.g., the "cold" temperature for a PCR thermal cycle). The second heating element assembly 4660 includes a first element 4664 and a second element 4665 that is electrically isolated from the first element 4664. In this manner, an electrical current can be conveyed to the first element 4664 independently from an electrical current conveyed to the second element 4665. Similarly stated, this arrangement allows for independent control of the first element 4664 and the second element 4665. In some embodiments, the sample flowing within the flow path 4620 is rapidly heated to about 90 C. To promote a rapid cooling down to about 60 C, in some embodiments, heat must flow out of the sample (and thus the flow member 4610). Thus, although the second temperature is described as being hotter than the desired sample temperature, in other embodiments, the output produced by the second heating element assembly 4660 (or any of the heating elements described herein) can be such that heat flows out of the flow path 4620 and/or the flow member 4610. In such embodiments, a current can still be supplied to the second heating element assembly 4660 to control the magnitude of the heat flow. In some embodiments, the second temperature can be, for example, between about 40 C and about 45 C (to allow heat transfer away from the sample at a controlled rate to facilitate maintaining the sample at about 60 C; e.g., the "cold" temperature for a PCR thermal cycle).

As shown in FIG. 4, the elements of the first heating element assembly 4650 and the elements of the second heating element assembly 4660 are each aligned along the flow axis $A_F$. Similarly stated, the first heating element assembly 4650 and the second heating element assembly 4660 are segmented along the flow axis $A_F$. This arrangement, along with the independent control of the elements of the first heating element assembly 4650 and the second heating element assembly 4660 allow for accurate control of heat flow to the portions of the flow path 4620. For example, in some embodiments, the first element 4661 of the first heating element assembly 4650 can be aligned with (and/or beneath) a first channel of the flow path 4620 (e.g., along the first, or "hot," portion of the flow member 4610). The second element 4662 of the first heating element assembly 4650 can be aligned with (and/or beneath) a second (or last) channel of the flow path 4620 (e.g., also along the first, or "hot," portion of the flow member 4610). The segmented, independently controllable design allows the first element 4661 to produce a first thermal output and the second element 4662 to produce a second thermal output that is different from the first thermal output. By producing different thermal outputs, the hot portion of the first channel and the hot portion of the second (or last) channel can be more accurately maintained at the desired temperature. For example, in some embodiments, the thermal design of the diagnostic device may result in greater heat transfer away from the second (or last) channel of the flow path 4620 (e.g., due to adjacent structures, internal air movement that increases convection transfer, or the like). In such situations, the second element 4662 can be controlled to provide a greater thermal output, thereby maintaining a consistent temperature between the first channel and the last channel. This, in turn, increases the overall accuracy of the device.

Similarly, in some embodiments, the first element 4664 of the second heating element assembly 4660 can be aligned with (and/or beneath) a first channel of the flow path 4620 (e.g., along the second, or "cold," portion of the flow member 4610). The second element 4665 of the second heating element assembly 4660 can be aligned with (and/or beneath) a second (or last) channel of the flow path 4620 (e.g., also along the second, or "cold," portion of the flow member 4610). The segmented, independently controllable design allows the first element 4664 to produce a first thermal output and the second element 4665 to produce a second thermal output that is different from the first thermal output. By producing different thermal outputs, the cold portion of the first channel and the cold portion of the second (or last) channel can be more accurately maintained at the desired temperature. For example, in some embodiments, the thermal design of the diagnostic device may result in greater heat transfer away from the second (or last) channel of the flow path 4620 (e.g., due to adjacent structures, internal air movement that increases convection transfer, or the like). In such situations, the second element 4665 can be controlled to provide a greater thermal output, thereby maintaining a consistent temperature between the first channel and the last channel. This, in turn, increases the overall accuracy of the device.

Thus, the heater assembly 4630 and the flow member 4610 can establish multiple temperature zones through which a sample can flow, and can define a desired number of amplification cycles to ensure the desired test sensitivity (e.g., at least 30 cycles, at least 34 cycles, at least 36 cycles, at least 38 cycles, or at least 40 cycles). Although each of the first heating element assembly 4650 and the second heating element assembly 4660 are shown as including two independent heating elements, in other embodiments, each of the first heating element assembly 4650 and the second heating element assembly 4660 can include any number of independent heating elements (e.g. three elements, four elements, or more). Although each of the first heating element assembly 4650 and the second heating element assembly 4660 are shown as being aligned with the flow axis $A_F$, in other embodiments, each of the first heating element assembly 4650 and the second heating element assembly 4660 can have any suitable alignment. For example, in some embodiments, a heating element assembly can be aligned with the flow channels. In some embodiments, a heating element assembly can include an element that extends beyond the flow path defined by a flow member (e.g., to minimize the effects of heat "roll off" on an end channel of the flow path).

The heating elements 4661, 4662, 4664, 4665 can be any suitable heating element or collection of heaters that can perform the functions described herein. For example, in some embodiments, any of the heating elements can be a single heating element that is thermally coupled to the flow member 4610, and that can cycle through multiple temperatures set points (e.g., between about 60 C and about 90 C). Moreover, any of the heating elements can be of any suitable design. For example, in some embodiments, any of the heating elements can be a resistance heater, a thermoelectric device (e.g. a Peltier device), or the like. In some embodiments, any of the heating elements can be resistance heaters that are lithographically produced on the substrate 4640.

The flow member 4610 can be coupled to the heater assembly 4630 in any suitable manner. For example, in some embodiments, the flow member 4610 can be coupled to the heater assembly 4630 by a series of mechanical fasteners, such as clamps, screws, or the like. In some such embodiments, the fasteners can also function as heat sinks to allow accurate control of the temperatures of the flow member 4610 and to avoid overheating. In other embodiments, the flow member 4610 can be coupled to the heater assembly 4630 by an adhesive (e.g., a pressure-sensitive adhesive). Similarly stated, in some embodiments, the flow member 4610 can be chemically bonded to the heater assembly 4630. In this manner, the flow member 4610 is fixedly coupled to the heater assembly 4630. Said another way, in some embodiments, the flow member 4610 is not designed to be removed and/or decoupled from the heater assembly 4630 during normal use. This arrangement facilitates a single-use, disposable device that includes the PCR module 4600.

Although the first heating element assembly 4650 and the second heating element assembly 4660 are shown and described as being coupled to the first side 4657 of the substrate 4640, in other embodiments, the first heating element assembly 4650 can be coupled to a first (e.g., front) side of the substrate 4640 and the second heating element assembly 4660 can be coupled to a second (e.g., back) side of the substrate 4640. In such embodiments, the flow member can be configured to wrap around the substrate. In yet other embodiments, a heating element can be disposed within a substrate (e.g., on an inner layer of a multi-layer construction).

Figure 5:
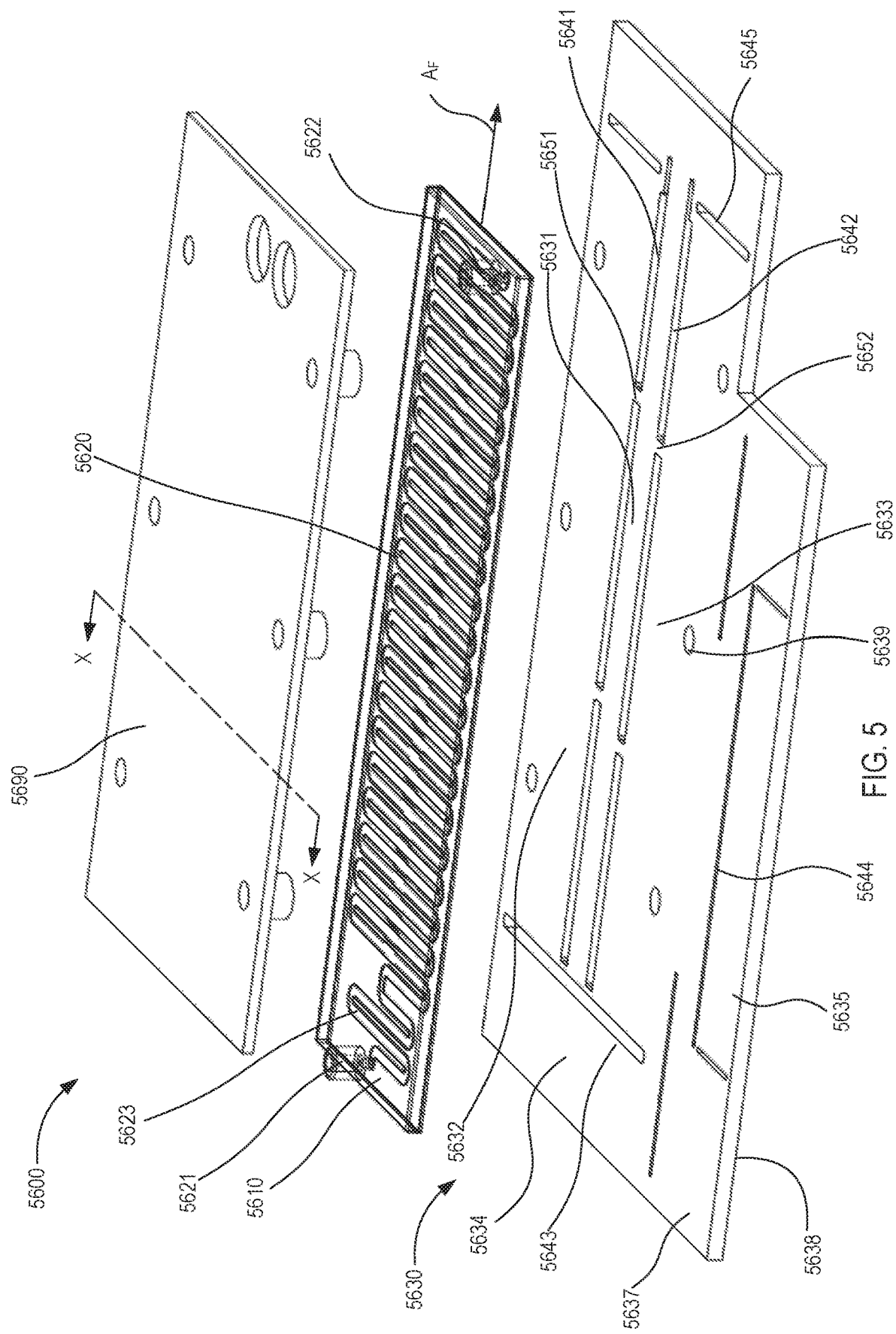
FIG. 5 is an exploded perspective view of an amplification module, according to an embodiment.

In some embodiments, a heater assembly of an amplification (or thermal reaction) module can be fabricated lithographically and/or can be integral with a printed circuit board. For example, FIG. 5 shows an exploded view of an amplification module 5600, according to an embodiment that includes a multi-layer heater assembly 5630 fabricated using lithography. The amplification module 5600 is configured to perform a thermal reaction (e.g., an amplification reaction) on an input of target nucleic acid mixed with required reagents, and can be included in any suitable diagnostic device. For example, the amplification module can be included in any of the diagnostic devices shown and described herein (including the device 6000 and the device 7000) or in International Patent Publication No. WO2016/109691, entitled "Devices and Methods for Molecular Diagnostic Testing," which is incorporated herein by reference in its entirety. In some embodiments, the amplification module 5600 is configured to conduct rapid amplification of an input target. In some embodiments, the amplification module 5600 is configured to generate an output copy number that reaches or exceeds the threshold of the sensitivity of an associated detection module (e.g., the detection module 3800 described below).

As described below, the heater assembly 5630 is a portion of a printed circuit board of a molecular diagnostics device (e.g., any of the devices described herein, including the device 6000 and the device 7000). Thus, the substrate, the circuit board layers and/or other structure of the heater assembly 5630 also support and/or is coupled to electronic components (not shown in FIGS. 5-17) that form the circuitry to control the heater assembly 5630 as well as the overall diagnostic device (e.g., flow pumps, introduction of reagents, sample preparation operations, or the like). For example, in some embodiments, a portion of the heater assembly 5630 (and any of the substrates or printed circuit board layers described herein) can be coupled to and/or support a processor, a controller, or the like. In this manner, the heater assembly 5630 can be a portion of a printed circuit board that performs many different electronic functions, including controlling the amplification of the sample, controlling sample movement, and other thermally-based functions described herein.

Figure 6:
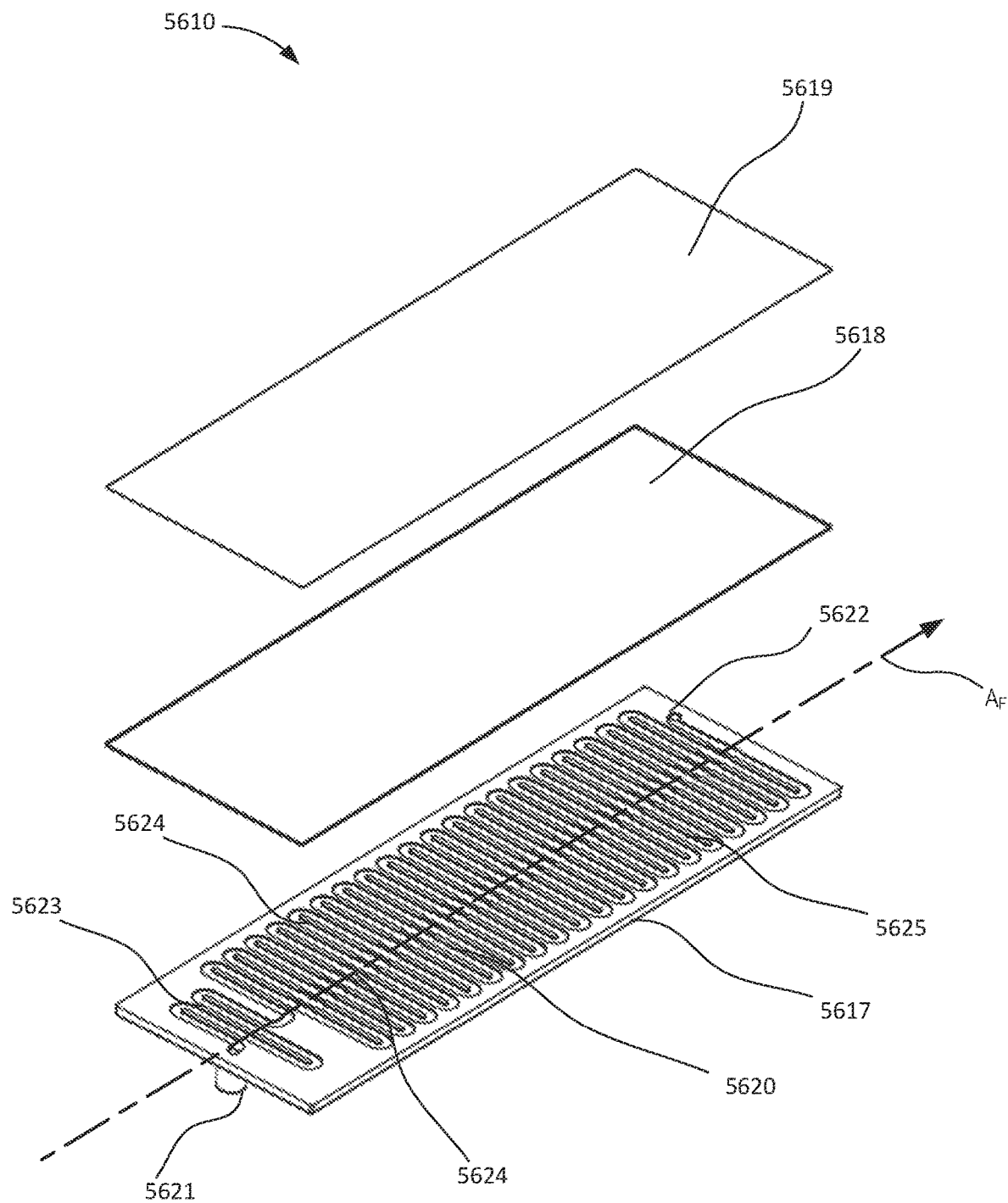
FIG. 6 is an exploded view of a flow member of the amplification module shown in FIG. 5.
Figure 7:
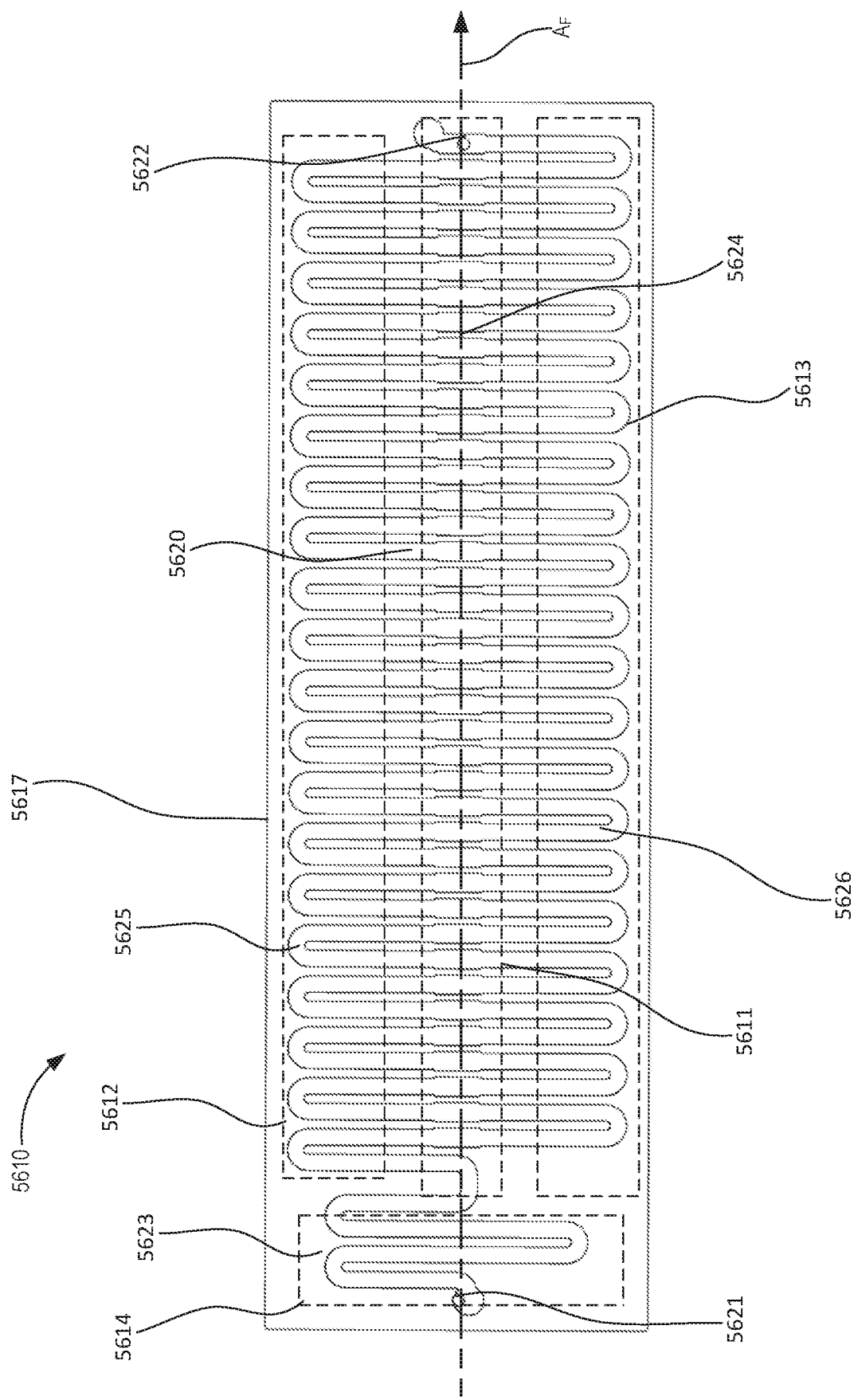
FIG. 7 is a top view of the flow member of the amplification module shown in FIG. 6.
Figure 8:
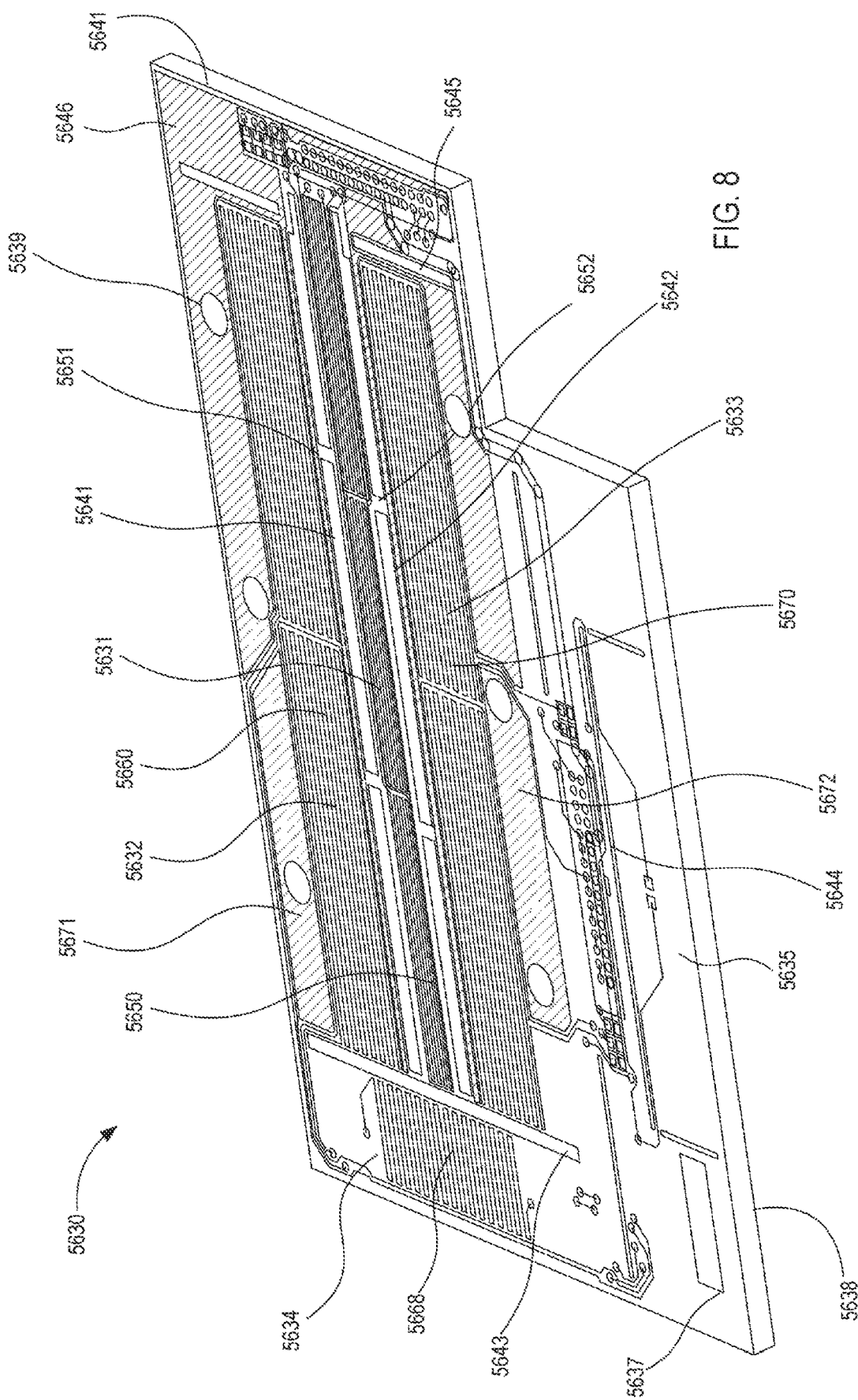
FIG. 8 is a perspective view of a heater assembly of the amplification module shown in FIG. 5.

Referring to FIG. 5, the amplification module 5600 includes a flow member 5610, a circuit board (or heater) assembly 5630, and a heat sink 5690. The flow member 5610 is coupled between the circuit board assembly 5630 and the heat sink 5690. As shown in FIGS. 5-7, the flow member 5610 includes a body 5617 and a lid 5619. The body 5617 is covered with a thin plastic lid 5619 which is attached with a pressure sensitive adhesive 5618. The lid 5619 allows for easy flow of thermal energy from the circuit board assembly 5630. In some embodiments, the flow member 5610 also contains features to allow other parts of the assembly (e.g., the circuit board assembly 5630) to align with the features on the flow member 5610, as well as features to allow the fluidic connections to be bonded correctly. The adhesive 5618 used to attach the lid 5619 is selected to be "PCR-safe" and is formulated to not deplete the reagent or target organism concentrations in the PCR reaction.

The body 5617 defines a flow path 5620 through which a sample can flow from an inlet port 5621 to an outlet port 5622. The flow member 5620 defines a flow axis $A_F$ that indicates the overall direction of the flow through the flow member 5610. As shown, the amplification flow path has a curved, switchback or serpentine pattern. More specifically, the flow member (or chip) 5610 has two serpentine patterns—an amplification pattern and a hot-start pattern 5623. The amplification pattern allows for amplification (i.e., PCR in this instance) to occur while the hot-start pattern 5623 accommodates the hot-start conditions of the PCR enzyme.

The serpentine arrangement provides a high flow length while maintaining the overall size of the amplification module 5600 within the desired limits. Moreover, the serpentine shape allows the flow path 5620 to intersect circuit board assembly 5630 at multiple locations (e.g., along the flow axis $A_F$). This arrangement can produce distinct "heating zones" throughout the flow path 5620, such that the amplification module 5600 can perform a "flow through" PCR when the sample flows through multiple different temperature regions. As shown, the flow path 5620 is shaped and/or has a geometry such that various portions of the flow path 5620 (e.g., a first portion 5624, a second portion 5625, and a third portion 5626) can be maintained at different temperatures by the circuit board assembly 5630. Specifically, as shown in FIG. 7, the circuit board assembly 5630 is coupled to the flow member 5610 to establish three temperature zones identified by the dashed lines: a first (i.e., central or "hot") temperature zone 5611, a second (or end) temperature zone 5612, and a third (or end) temperature zone 5613. The circuit board assembly 5630 and the flow member 5610 also establish a fourth (or hot start) temperature zone 5614. In use, the second temperature zone 5612 (which includes the second portion 5625 of the flow path 5620) and the third temperature zone 5613 (which includes the third portion 5626 of the flow path 5620) can be maintained at a temperature of about 60 degrees Celsius (and/or at a surface temperatures such that the fluid flowing therethrough reaches a temperature of about 60 degrees Celsius). The first temperature zone 5611 (which includes the first portion 5624 of the flow path 5620) can be maintained at a temperature of about 90 degrees Celsius (and/or at a surface temperatures such that the fluid flowing therethrough reaches a temperature of about 90 degrees Celsius). Thus, in use the first portion 5624, the second portion 5625, and the third portion 5626 can be maintained at two different temperatures by the circuit board assembly 5630.

As shown, the serpentine pattern establishes 40 different zones of "cold-to-hot-to-cold;" or 40 amplification cycles. In other embodiments, however, the flow member 5610 (or any of the other flow members described herein) can define any suitable number of switchbacks or amplification cycles to ensure the desired test sensitivity. In some embodiments, the flow member can define at least 30 cycles, at least 34 cycles, at least 36 cycles, at least 38 cycles, or at least 40 cycles.

The dimensions of the flow channel 5620 in the flow member 5610 impact the temperature conditions of the PCR and dictate the overall dimensions of the chip, and thus affect the overall power consumption of the amplification module 5600. For example, a deeper, narrower channel will develop a larger gradient in temperature from the side closest to the lid 5619 to the bottom (resulting in lower PCR efficiency). This arrangement, however, requires less overall space since the channels will take up less overall surface area facing the heater assembly 5630 (and thus require less energy to heat). The opposite holds true for a wide and shallow channel. In some embodiments, the depth of the flow channel 5620 is about 0.15 mm and the width of the flow channel 5620 is between about 1.1 mm and about 1.3 mm. More particularly, in some embodiments, the flow channel 5620 has a width of about 1.1 mm in the "narrow" sections (that are within the second temperature zone 5612 and the third temperature zone 5613) and about 1.3 mm in the "wide" section (that falls within the first temperature zone 5611). In some embodiments, the overall path length is about 960 mm (including both the amplification portion and the hot start portion 5623). In such embodiments, the total path length of the amplification portion is about 900 mm. This produces a total volume of the flow channel 5620 of about 160 µl (including the hot start portion 5623) and about 150 µl (without the hot start portion 5623). In some embodiments, the separation between each parallel path is between about 0.4 mm and about 0.6 mm.

The flow member 5610 and/or body 5617 can be constructed from any suitable material, and can have any suitable thickness. For example, in some embodiments, the flow member 5610 and/or body 5617 (and any of the flow members described herein) can be molded from COC (Cyclic Olefin Copolymer) plastic, which has inherent barrier properties and low chemical interactivity. In other embodiments, the flow member 5610 and/or body 5617 (and any of the flow members described herein) can be constructed from a graphite-based material (for improved thermal properties). The overall thickness of the flow member 5610 can be less than about 0.5 mm, less than about 0.4 mm, less than about 0.3 mm or less than about 0.2 mm.

The flow member 5610 can be coupled to the circuit board assembly 5630 in any suitable manner. For example, in some embodiments, the flow member 5610 can be coupled to the heater assembly 5630 at least in part by the mechanical fasteners used to couple the heat sink 5690 to the circuit board assembly 5630. In some such embodiments, the fasteners can also function as heat sinks to allow accurate control of the temperatures of the flow member 5610 and to avoid overheating. In other embodiments, the flow member 5610 can be coupled to the heater assembly 5630 by an adhesive (e.g., a pressure-sensitive adhesive). Similarly stated, in some embodiments, the flow member 5610 can be chemically bonded to the heater assembly 5630. In this manner, the flow member 5610 is fixedly and irreversibly coupled to the heater assembly 5630. Said another way, in some embodiments, the flow member 5610 is not designed to be removed and/or decoupled from the heater assembly 5630 during normal use. This arrangement facilitates a single-use, disposable device that includes the PCR module 5600.

Figure 9:
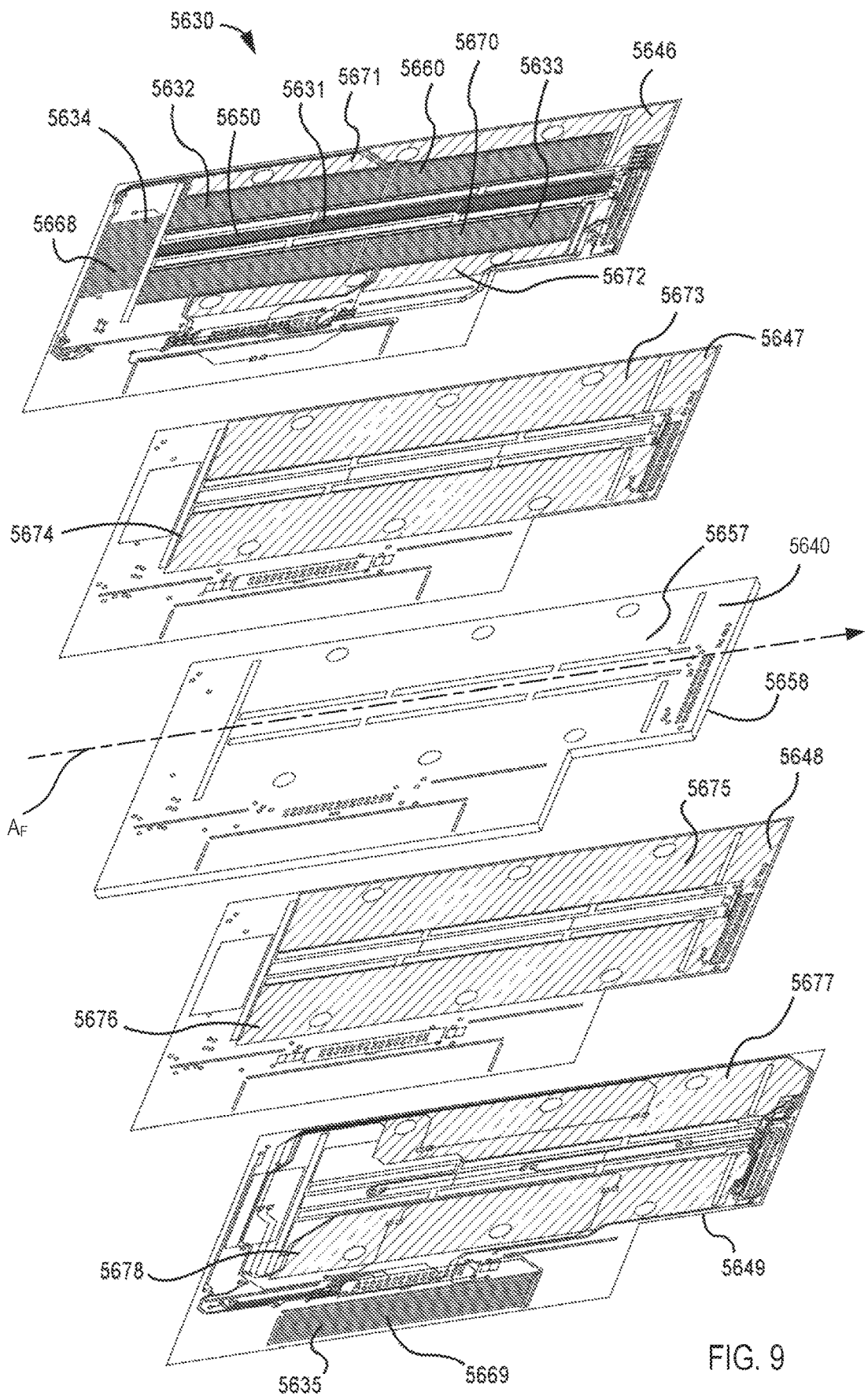
FIGS. 9 and 10 are exploded perspective views of the heater assembly shown in FIG. 8.
Figure 10:
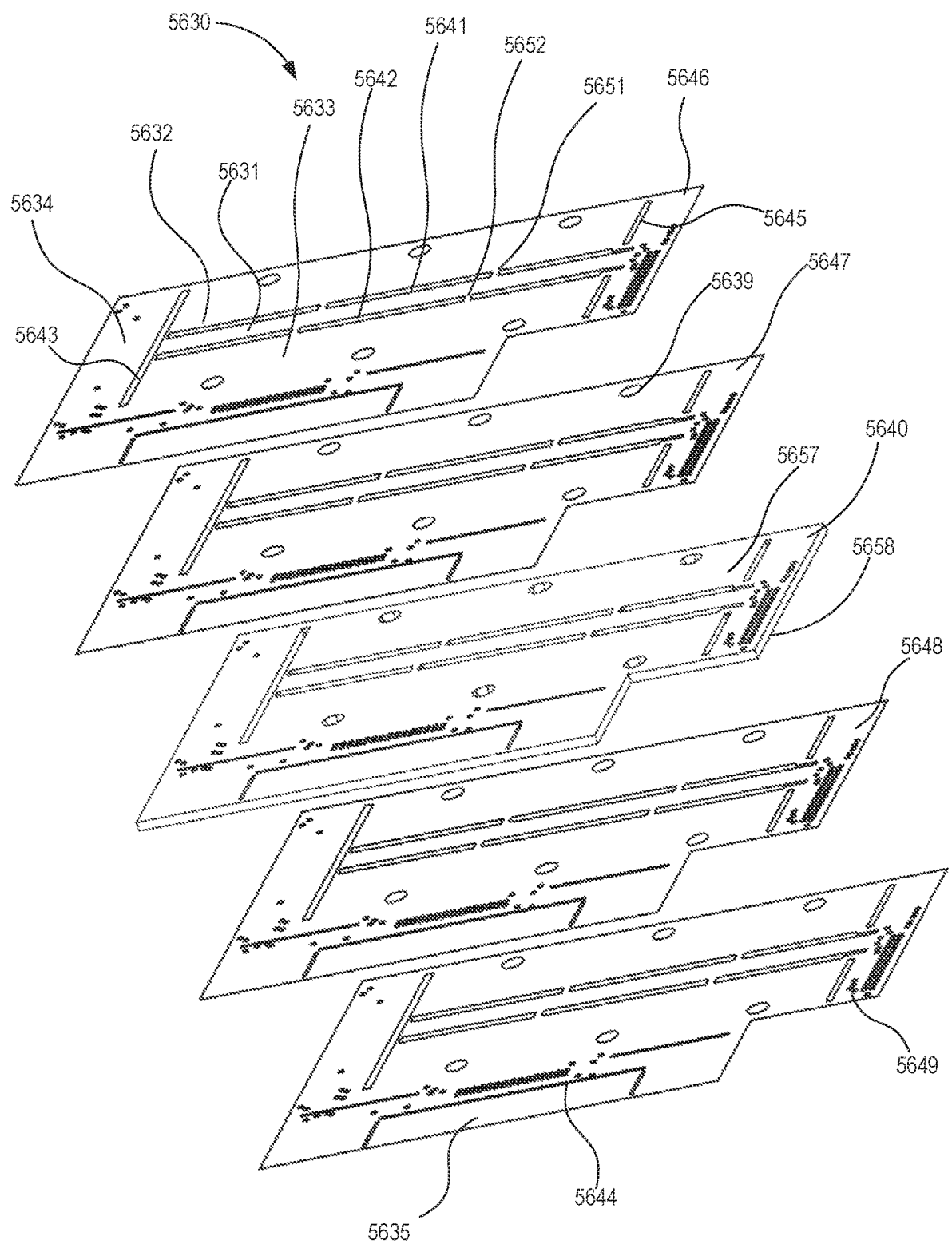

The circuit board (or heater) assembly 5630 is a multilayer circuit board having a first side 5637 and a second side 5638. FIGS. 9 and 10 show an exploded view of each layer of the circuit board assembly 5630. FIG. 9 shows various layers of the circuit board 5630, including the copper traces fabricated thereon, and FIG. 10 shows a structural representation of each layer. Although FIG. 9 shows the four layers including copper (or a conductive portion), in some embodiments, a thin film substrate (not shown) separates the adjacent copper layers. As shown, the circuit board assembly 5630 includes a substrate 5640 having a first side 5657 and a second side 5658, a first (or outer heater) layer 5646, a second (or inner heater) layer 5647, a third (or inner sensor) layer 5648, and a fourth (or outer sensor) layer 5649. The substrate 5640 provides structural support, and is constructed from an electrically isolative material upon which the four layers are fabricated using lithographic procedures. The substrate 5640 (and any of the substrates described herein) can be constructed from any suitable material, such as, for example, a composite material including woven glass and epoxy. In some embodiments, the substrate 5640 (and any of the substrates described herein) can be constructed from a material having a glass transition temperature (Tg) of greater than about 170 C. In other embodiments, the substrate 5640 (and any of the substrates described herein) can be constructed from a material having a glass transition temperature (Tg) of greater than about 180 C (e.g., material 370HR produced by the Isola Group). In this manner, the substrate 5640 can maintain the desired rigidity and dimensional integrity to provide repeatable thermal performance for each channel of the flow path 5620.

Figure 11:
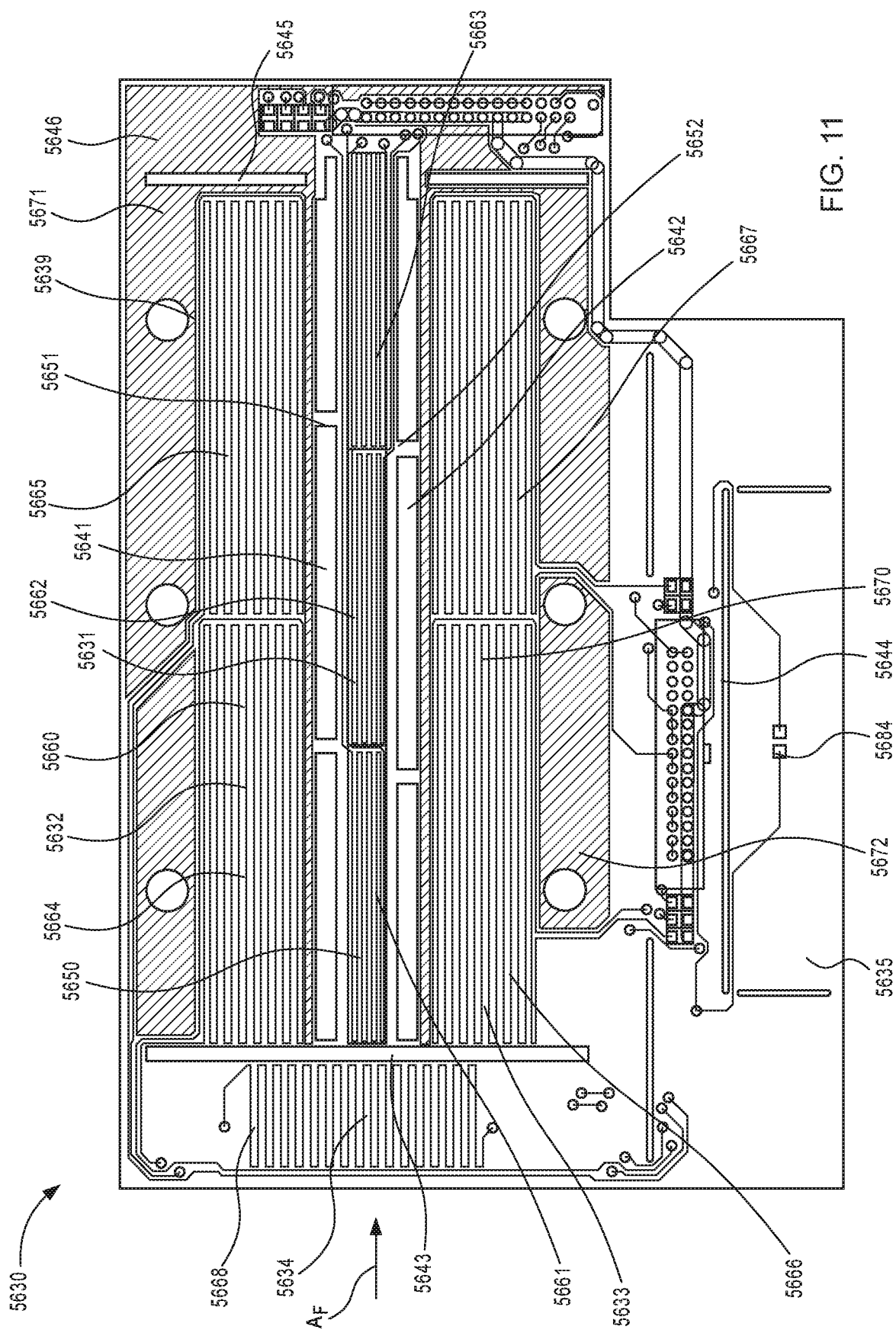
FIG. 11 is a top view of the heater assembly show in FIG. 8, showing a first (or top) layer of the assembly.
Figure 12:
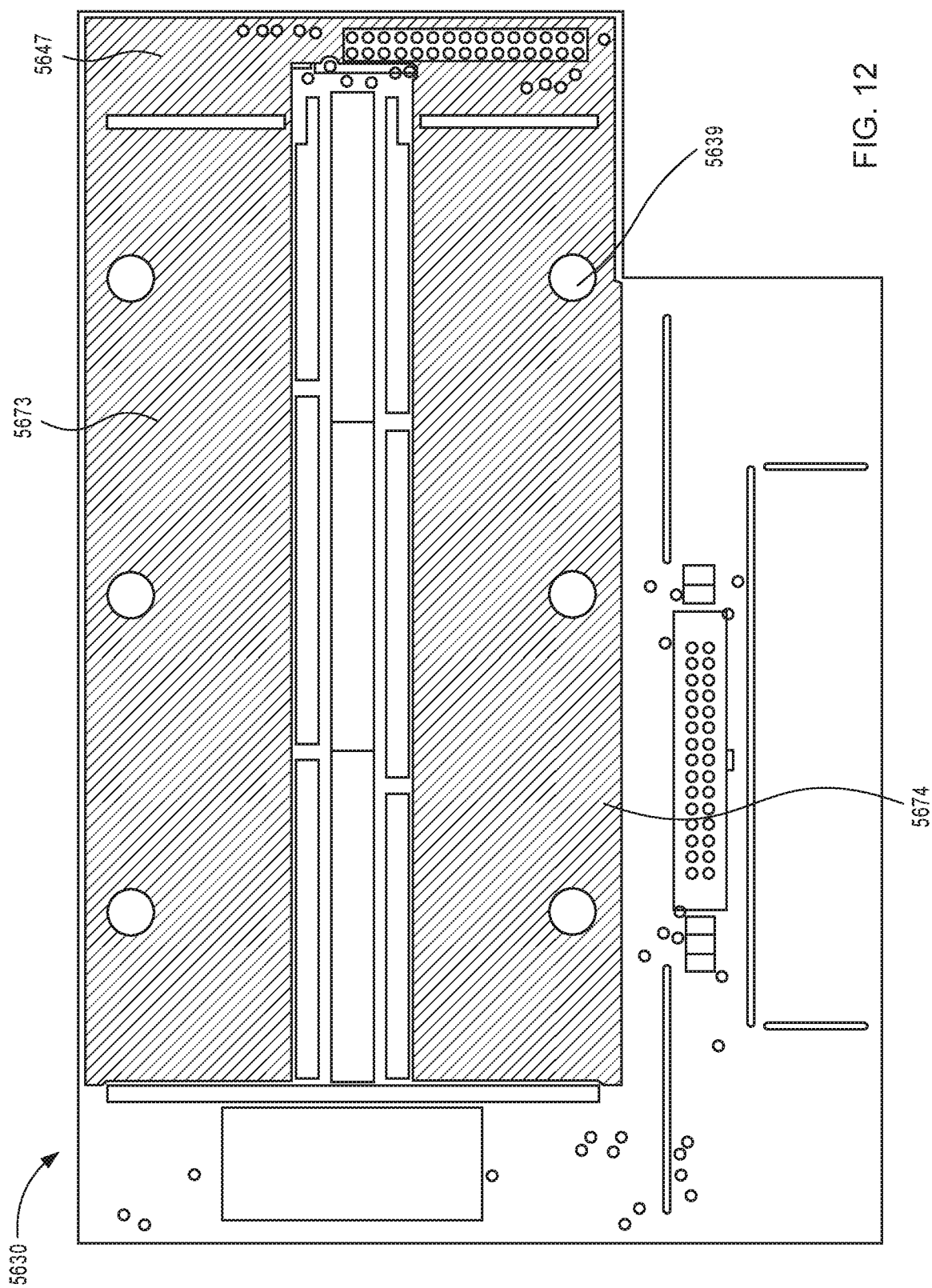
FIG. 12 is a top view of the heater assembly show in FIG. 8, showing a second layer of the assembly.
Figure 13:
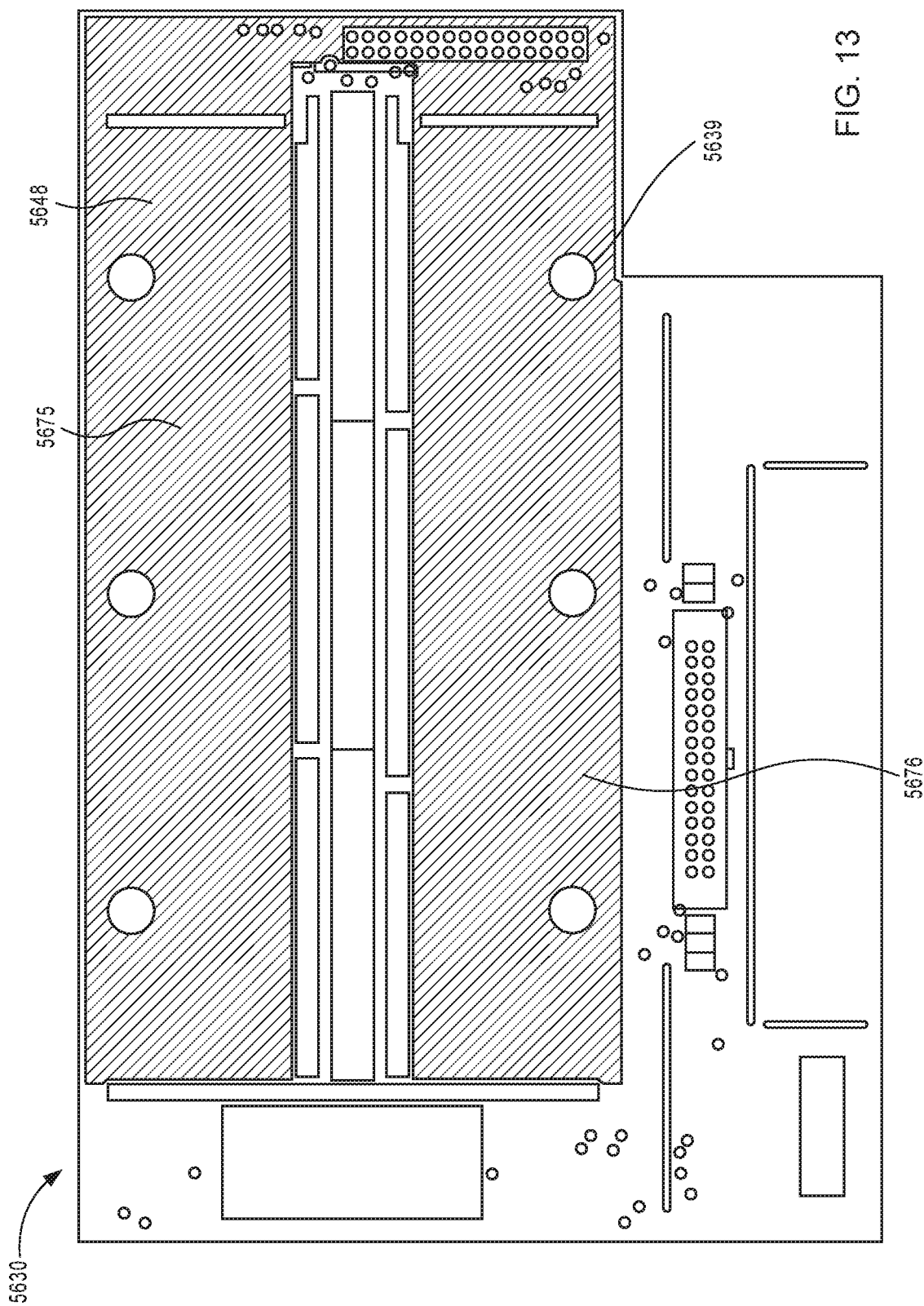
FIG. 13 is a top view of the heater assembly show in FIG. 8, showing a third layer of the assembly.
Figure 14:
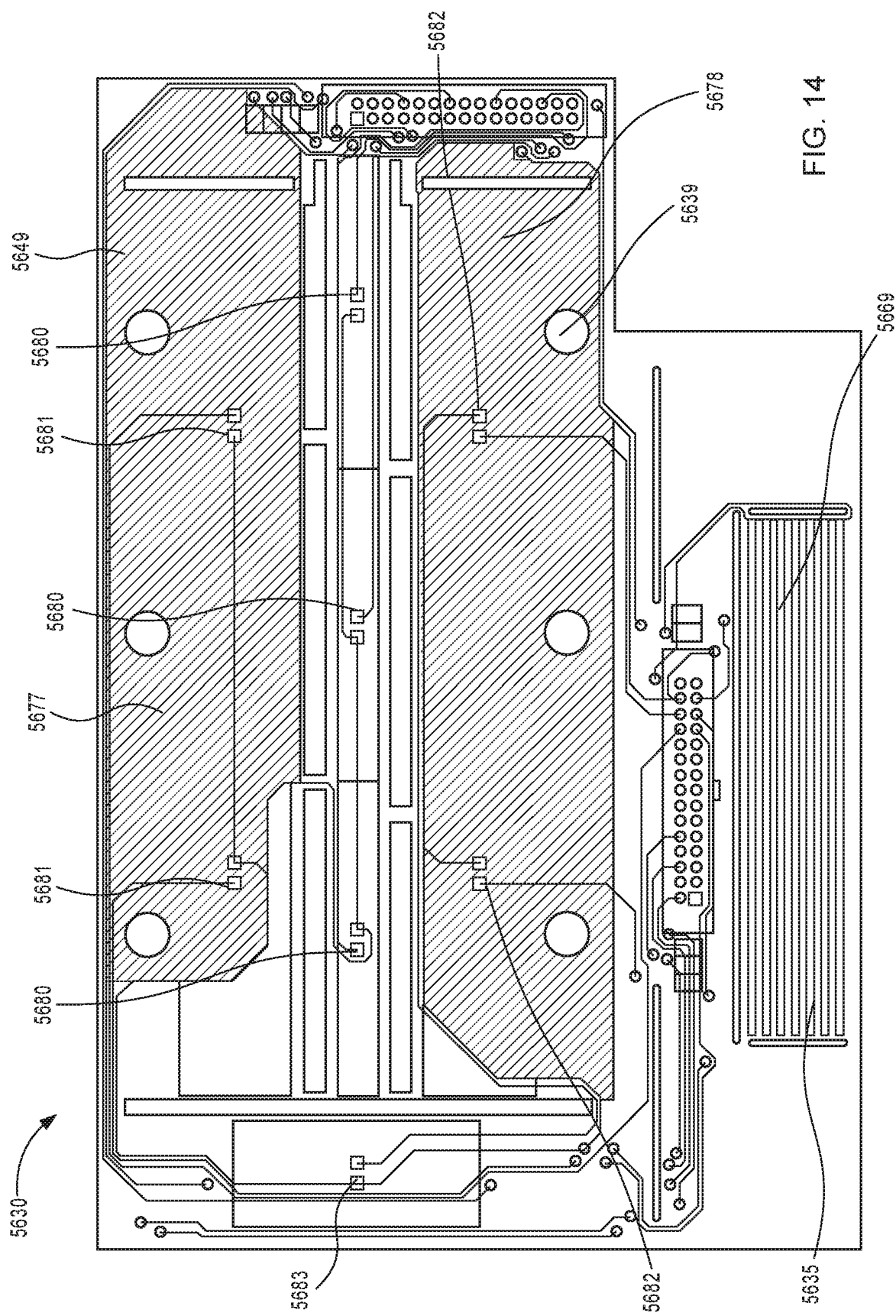
FIG. 14 is a top view of the heater assembly show in FIG. 8, showing a fourth (or bottom) layer of the assembly.

FIGS. 11-14 show top views of each of the four layers of the printed circuit board assembly 5630. Specifically, FIG. 11 shows a top view of the first (or outer heater) layer 5646. FIG. 12 shows a top view of the second (or inner heater) layer 5647. FIG. 13 shows a top view of the third layer 5648. FIG. 14 shows a top view of the fourth (or outer sensor) layer 5649. As discussed below, the fourth layer 5649 also includes the fifth heater assembly 5669. Each of these layers is discussed below within the description of the overall printed circuit board assembly 5630.

Referring again to FIG. 5, the circuit board assembly 5630 defines a series of apertures (also referred to as openings, cut-outs, or vias) that separate the circuit board assembly 5630 into several different portions (or heating zones). Specifically, the circuit board assembly 5630 defines a first set of apertures 5641 that separates a first portion (or heating zone) 5631 of the assembly 5630 from a second portion (or heating zone) 5632 of the assembly 5630. The first set of apertures 5641 includes three openings that are elongated along the flow axis $A_F$, and that are separated by two connection lugs 5651 (only one of the connection lugs 5651 is identified). Thus, the first set of apertures 5641 produces a longitudinally oriented thermal barrier between the first heating zone 5631 and the second heating zone 5632. Similarly, the circuit board assembly 5630 defines a second set of apertures 5642 that separates the first portion (or heating zone) 5631 of the assembly 5630 from a third portion 5633 (or heating zone) of the assembly 5630. The second set of apertures 5642 includes three openings that are elongated along the flow axis $A_F$, and that are separated by two connection lugs 5652 (only one of the connection lugs 5652 is identified). Thus, the second set of apertures 5642 produces a longitudinally oriented thermal barrier between the first heating zone 5631 and the third heating zone 5633.

The first heating zone 5631 is disposed between the second heating zone 5632 and the third heating zone 5633. Moreover, when the circuit board assembly 5630 is coupled to the flow member 5610, the first portion 5631 is aligned with the first (or "hot") temperature zone 5611, the second portion 5632 is aligned with the second (or "cold") temperature zone 5612, and the third portion 5633 is aligned with the third (or "cold") temperature zone 5613. This is illustrated in the cross-sectional view shown in FIG. 15, which shows the first temperature zone 5611 of the flow member (identified by the dashed lines) being surrounded and/or isolated by the first set of apertures 5641 and the second set of apertures 5642. This arrangement allows the first heater assembly 5650 located within first heating zone 5631 to heat the first temperature zone 5611 of the flow member 5610. In some embodiments, the first heater assembly 5650 can be controlled to maintain the first temperature zone 5611 at a temperature of about 90 degrees Celsius (and/or at a surface temperatures such that the fluid flowing therethrough reaches a temperature of about 90 degrees Celsius). This arrangement further allows the second heater assembly 5660 located within second heating zone 5632 to heat the second temperature zone 5612 of the flow member 5610. In some embodiments, the second heater assembly 5660 can be controlled to maintain the second temperature zone 5612 at a temperature of about 60 degrees Celsius (and/or at a surface temperatures such that the fluid flowing therethrough reaches a temperature of about 60 degrees Celsius). This arrangement further allows the third heater assembly 5670 located within third heating zone 5633 to heat the third temperature zone 5613 of the flow member 5610. In some embodiments, the third heater assembly 5670 can be controlled to maintain the third temperature zone 5613 at a temperature of about 60 degrees Celsius (and/or at a surface temperatures such that the fluid flowing therethrough reaches a temperature of about 60 degrees Celsius). In this manner, the heater assembly 5630 and the flow member 5610 can establish multiple temperature zones through which a sample can flow, and can define a desired number of amplification cycles to ensure the desired test sensitivity (e.g., at least 30 cycles, at least 34 cycles, at least 36 cycles, at least 38 cycles, or at least 40 cycles).

Referring to FIG. 11, the first heating zone 5631 of the printed circuit board assembly 5630 includes a first heater assembly 5650. The first heater assembly 5650 includes a first heating element 5661, a second heating element 5662, and a third heating element 5663, each of which is electrically isolated from the other two heating elements in the first heater assembly 5650. Said another way, each of the first heating element 5661, the second heating element 5662, and the third heating element 5663 is separate from (or electrically isolated from) the others. In this manner, an electrical current can be conveyed to each of the first heating element 5661, the second heating element 5662, and the third heating element 5663 independently from an electrical current being conveyed to the other heating elements of the first heater assembly 5650. This arrangement allows for independent control of the first heating element 5661, the second heating element 5662, and the third heating element 5663. Each of the first heating element 5661, the second heating element 5662, and the third heating element 5663 are conductive traces that are fabricated on the first layer 5646 by lithographic techniques. Although the first heater assembly 5650 is shown as being fabricated in the first layer 5646, in other embodiments, the first heater assembly 5650 can be fabricated in any layer of the circuit board assembly 5630.

The second heating zone 5632 of the printed circuit board assembly 5630 includes a second heater assembly 5660. The second heater assembly 5660 includes a first heating element 5664 and a second heating element 5665, each being electrically isolated from the other. Said another way, the first heating element 5664 is separate from the second heating element 5665, and vice-versa. In this manner, an electrical current can be conveyed to the first heating element 5664 independently from an electrical current being conveyed to the second heating element 5665, and vice-versa. This arrangement allows for independent control of the first heating element 5664 and the second heating element 5665. The first heating element 5664 and the second heating element 5665 are each conductive traces that are fabricated on the first layer 5646 by lithographic techniques. Although the second heater assembly 5660 is shown as being fabricated in the first layer 5646, in other embodiments, the second heater assembly 5660 can be fabricated in any layer of the circuit board assembly 5630.

The third heating zone 5633 of the printed circuit board assembly 5630 includes a third heater assembly 5670. The third heater assembly 5670 includes a first heating element 5666 and a second heating element 5667, each being electrically isolated from the other. Said another way, the first heating element 5666 is separate from the second heating element 5667, and vice-versa. In this manner, an electrical current can be conveyed to the first heating element 5666 independently from an electrical current being conveyed to the second heating element 5667, and vice-versa. This arrangement allows for independent control of the first heating element 5666 and the second heating element 5667. The first heating element 5666 and the second heating element 5667 are each conductive traces that are fabricated on the first layer 5646 by lithographic techniques. Although the third heater assembly 5670 is shown as being fabricated in the first layer 5646, in other embodiments, the third heater assembly 5670 can be fabricated in any layer of the circuit board assembly 5630.

In use, the first heater assembly 5650 produces a thermal output to maintain the first temperature zone 5611 of the flow member 5610 at a first temperature. The first temperature can be, for example, between about 100 C and 115 C (to heat the sample therein to about 90 C; e.g., the "hot" temperature for a PCR thermal cycle). Additionally, the segmented, independently controllable design allows the first heating element 5661 to produce a first thermal output, the second heating element 5662 to produce a second thermal output, and the third heating element 5663 to produce a third thermal output, each of which can be different from the others. By producing different thermal outputs, the hot portion of the flow channel 5620 can be more accurately maintained at the desired temperature. For example, in some embodiments, the thermal design of the diagnostic device may result in greater heat transfer away from the first or last channels of the flow path 5620 (e.g., due to adjacent structures, internal air movement that increases convection transfer, or the like). In such situations, the first heating element 5661 and the third heating element 5663 can be controlled to provide a greater thermal output, thereby maintaining a consistent temperature between the first channel and the last channel. This, in turn, increases the overall accuracy of the device.

The second heater assembly 5660 produces a thermal output to maintain the second temperature zone 5612 of the flow member 5610 at a second temperature. The second temperature can be different from the first temperature, and can be, for example, about 60 C to about 75 C (to heat the sample therein to about 60 C; e.g., the "cold" temperature for a PCR thermal cycle). Additionally, the segmented, independently controllable design allows the first heating element 5664 to produce a first thermal output and the second heating element 5665 to produce a second thermal output different from the first thermal output. By producing different thermal outputs, the cold portion of the flow channel 5620 can be more accurately maintained at the desired temperature. For example, in some embodiments, the thermal design of the diagnostic device may result in greater heat transfer away from the first or last channels of the flow path 5620 (e.g., due to adjacent structures, internal air movement that increases convection transfer, or the like). In such situations, the first heating element 5664 and the third heating element 5665 can be controlled to provide different thermal outputs, thereby maintaining a consistent temperature between the first channel and the last channel. This, in turn, increases the overall accuracy of the device.

In some embodiments, the sample flowing within the flow path 5620 is rapidly heated to about 90 C. To promote a rapid cooling down to about 60 C, in some embodiments, heat must flow out of the sample (and thus the flow member 5610). Thus, although the second temperature is described as being hotter than the desired sample temperature, in other embodiments, the output produced by the second heater assembly 5660 (or any of the heating elements described herein) can be such that heat flows out of the flow path 5620 and/or the flow member 5610. In such embodiments, a current can still be supplied to the second heater assembly 5660 to control the magnitude of the heat flow. In some embodiments, the second temperature can be, for example, between about 40 C and about 45 C (to allow heat transfer away from the sample at a controlled rate to facilitate maintaining the sample at about 60 C; e.g., the "cold" temperature for a PCR thermal cycle).

The third heater assembly 5670 produces a thermal output to maintain the third temperature zone 5613 of the flow member 5610 at a third temperature. The third temperature can be different from the first temperature and/or the second temperature. In some embodiments, the third temperature can be the same as the second temperature, and can be, for example, about 60 C to about 75 C (to heat the sample therein to about 60 C; e.g., the "cold" temperature for a PCR thermal cycle). Additionally, the segmented, independently controllable design allows the first heating element 5666 to produce a first thermal output and the second heating element 5667 to produce a second thermal output different from the first thermal output. By producing different thermal outputs, the cold portion of the flow channel 5620 can be more accurately maintained at the desired temperature. For example, in some embodiments, the thermal design of the diagnostic device may result in greater heat transfer away from the first or last channels of the flow path 5620 (e.g., due to adjacent structures, internal air movement that increases convection transfer, or the like). In such situations, the first heating element 5665 and the third heating element 5667 can be controlled to provide different thermal outputs, thereby maintaining a consistent temperature between the first channel and the last channel. This, in turn, increases the overall accuracy of the device.

As described above, the first set of apertures 5641 produces a longitudinally oriented thermal barrier between the first heating zone 5631 and the second heating zone 5632, and the second set of apertures 5642 produces a longitudinally oriented thermal barrier between the first heating zone 5631 and the third heating zone 5633. Thus, the first set of apertures 5641 and the second set of apertures 5642 collectively thermally isolate the first heating zone 5631 of the circuit board assembly 5630. By minimizing the heat transfer between the first heating zone 5631, the second heating zone 5632, and the third heating zone 5633, accuracy and control of the temperature to which each heating zone is heated can be improved.

Referring to FIG. 11, the connection lugs (or portions) 5651 that separate the first set of apertures 5641 into three openings are offset from the connection lugs (or portions) 5652 that separate the second set of apertures 5642 into three openings. Similarly stated, a connection lug 5651 is located at a different longitudinal position than a corresponding connection lug 5652. Said another way, the connection lugs 5651 are positioned at a different location along the flow axis $A_F$ than are the connection lugs 5652. This arrangement allows each of the connection lugs 5651 and the connection lugs 5652 to be positioned below (or aligned with) a different channel of the flow path 5620 when the circuit board assembly 5630 is coupled to the flow member 5610. As an example, this arrangement allows a connection lug 5651 to be aligned with, for example, the tenth channel within the flow path 5620 while the corresponding connection lug 5652 is aligned with, for example, the twelfth channel within the flow path 5620. Because the thermal performance of the first heating zone 5631 in the areas adjacent the connection lugs 5651 and 5652 is different than the thermal performance at other spatial locations, the offset arrangement of the connection lugs minimizes any differences in the temperature of the flow channel. This, in turn, increases the overall accuracy of the device.

The connection lugs (or portions) 5651 and the connection lugs (or portions) 5652 can be of any suitable size. For example, the width of the connection lugs 5651 and the connection lugs 5652 can be such that during normal use deflection and/or warping of the circuit board assembly 5630 is minimized. Any such warping could result in changes in the contact between the flow member 5610 and the heater assemblies, thereby resulting in variation in the temperatures maintained within the flow channel 5620. In some embodiments, the width of the connection lugs 5651 and/or the connection lugs 5652 can be about 5 percent of the width of one of the openings from the first set of apertures 5641 and/or the second set of apertures 5642. In other embodiments, the width of the connection lugs 5651 and/or the connection lugs 5652 can be between about 5 percent and about 10 percent of the width of one of the openings from the first set of apertures 5641 and/or the second set of apertures 5642. In other embodiments, the width of the connection lugs 5651 and/or the connection lugs 5652 can be between about 10 percent and about 20 percent of the width of one of the openings from the first set of apertures 5641 and/or the second set of apertures 5642.

In addition to including three heating zones for the PCR reaction, the circuit board assembly 5630 also defines a third aperture 5643 that separates a fourth portion (or heating zone) 5634 from the other heating zones. The third aperture 5643 is elongated substantially perpendicular to the flow axis $A_F$, and thus produces a laterally-oriented thermal barrier between the fourth heating zone 5634 and the amplification heating zones (i.e., the first heating zone 5631, the second heating zone 5632, and the third heating zone 5633). Although shown as being a single opening, in other embodiments the fourth heating zone 5634 can be separated by a series of apertures and connection lugs.

As shown, the fourth heating zone 5634 is disposed at an end portion of the circuit board assembly 5630, opposite the first heating zone, 5631, the second heating zone 5632, and the third heating zone 5633. Moreover, when the circuit board assembly 5630 is coupled to the flow member 5610, the fourth portion 5634 is aligned with the hot-start pattern 5623 of the flow member 5610. This arrangement allows the fourth heater assembly 5668 located within fourth heating zone 5634 to heat the hot-start pattern 5623 of the flow member 5610. The hot-start portion 5623 reduces non-specific amplification and allows the use of certain PCR reagents that remain inactive until heated. In some embodiments, the first heater assembly 5650 can be controlled to maintain the first temperature zone 5611 at a temperature of between about 45 degrees Celsius and about 95 degrees Celsius (and/or at a surface temperatures such that the fluid flowing therethrough reaches a temperature between about 45 degrees Celsius and about 95 degrees Celsius).

The fourth heating zone 5634 of the printed circuit board assembly 5630 includes a fourth heater assembly 5668. The fourth heater assembly 5668 includes a single heating element that is electrically isolated from the heating elements included in the other heating assemblies (e.g., the first heating assembly 5650). In this manner, an electrical current can be conveyed to the fourth heater assembly 5668 independently from an electrical current being conveyed to the other heating elements of the first heater assembly 5650, the second heater assembly 5660 and/or the third heater assembly 5670. This arrangement allows for independent control of the hot-start portion of the amplification module 5600. The heating element of the fourth heater assembly 5668 includes conductive traces that are fabricated on the first layer 5646 by lithographic techniques. Although the fourth heater assembly 5668 is shown as being fabricated in the first layer 5646, in other embodiments, the fourth heater assembly 5668 can be fabricated in any layer of the circuit board assembly 5630. Moreover, although the fourth heater assembly 5668 is shown as including a single heating element, in other embodiments, the fourth heater assembly 5668 can include any number if independently controllable (or segmented) heating elements.

The circuit board assembly 5630 defines a fourth set of apertures 5644 that separates the fifth portion (or heating zone) 5635 from the other portions of the board. The fourth set of apertures 5644 includes three openings that are separated by two connection lugs (the connection lugs are not identified). The fourth set of apertures 5644 includes one opening that is elongated along the flow axis $A_F$, and two openings that are elongated substantially perpendicular to the flow axis $A_F$. Thus, the fourth set of apertures 5644 produces thermal barrier that surrounds the fifth heating zone 5635.

Figure 16:
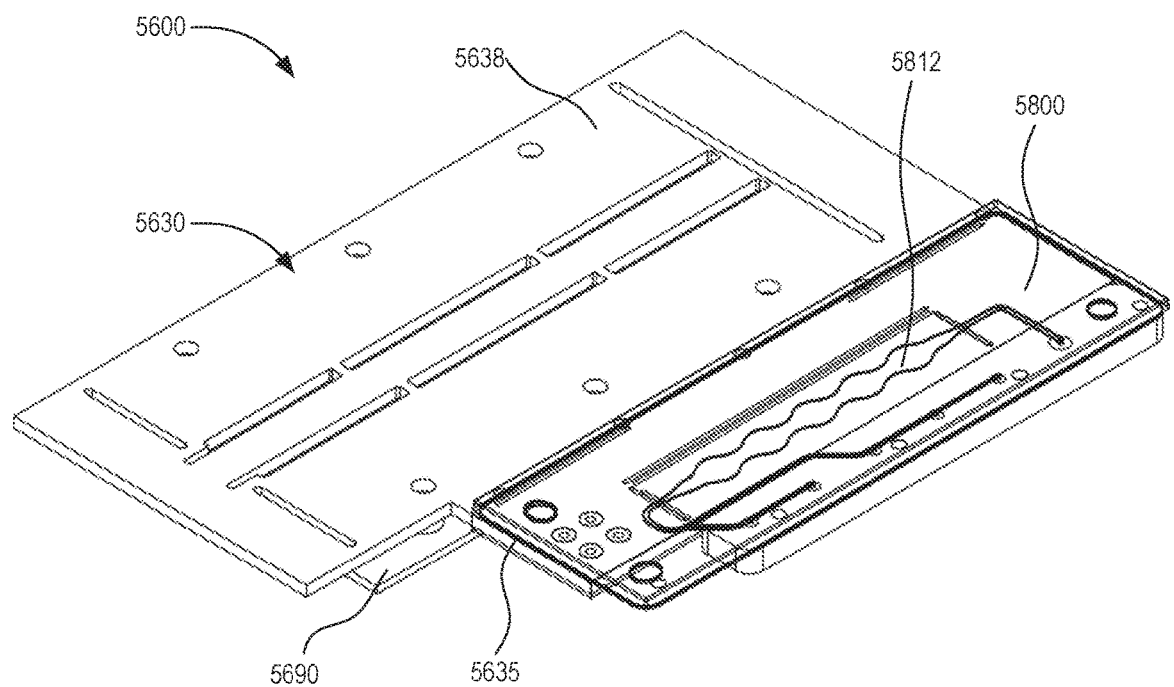
FIG. 16 is a bottom perspective view of the amplification module shown in FIG. 5 coupled to a detection module, according to an embodiment.

As shown, the fifth heating zone 5635 is disposed at a side portion of the circuit board assembly 5630, opposite the first heating zone, 5631, the second heating zone 5632, and the third heating zone 5633. Moreover, when the circuit board assembly 5630 is coupled to the flow member 5610, the fifth heating zone 5635 is spaced apart from the flow member 5610. Thus, the heat produced by fifth heater assembly 5669 (see FIG. 14) is not directed towards any portion of the flow path 5620. Rather, as shown in FIG. 16, the fifth heating zone 5635 is aligned with a detection module 5800. This arrangement allows the fifth heater assembly 5669 located within fifth heating zone 5635 to heat portions of the detection module 5800 to facilitate post-amplification detection of a target organism. In this manner, the circuit board assembly 5630 can function to heat both the flow member 5610 to facilitate amplification and the detection module 5800 to facilitate detection.

Referring to FIG. 14, the fifth heating zone 5635 of the printed circuit board assembly 5630 includes a fifth heater assembly 5669. The fifth heater assembly 5669 includes a single heating element that is electrically isolated from the heating elements included in the other heating assemblies (e.g., the first heating assembly 5650). In this manner, an electrical current can be conveyed to the fifth heater assembly 5669 independently from an electrical current being conveyed to the other heating elements of the first heater assembly 5650, the second heater assembly 5660, the third heater assembly 5670, and/or the fourth heater assembly 5668. This arrangement allows for independent control of the detection module 5800. The heating element of the fifth heater assembly 5669 includes conductive traces that are fabricated on the fourth layer 5646 by lithographic techniques. Although the fifth heater assembly 5669 is shown as being fabricated in the fourth layer 5649, in other embodiments, the fifth heater assembly 5669 can be fabricated in any layer of the circuit board assembly 5630. Moreover, although the fifth heater assembly 5669 is shown as including a single heating element, in other embodiments, the fifth heater assembly 5669 can include any number if independently controllable (or segmented) heating elements.

Figure 17:
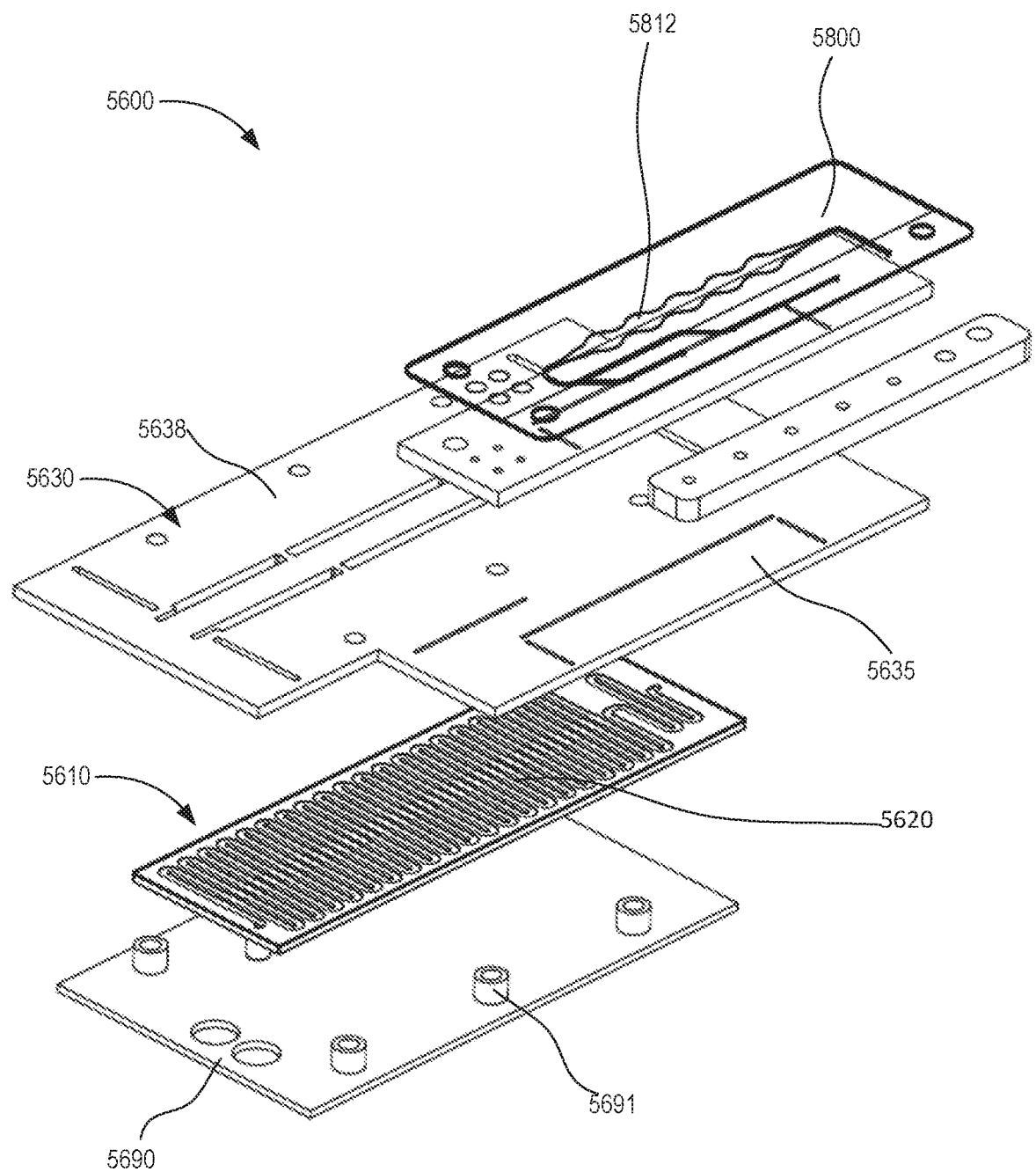
FIG. 17 is an exploded view of the amplification module and the detection module shown in FIG. 16.

Referring to FIGS. 16 and 17, the detection module 5800 is coupled to the second side 5638 of the printed circuit board assembly 5630. Similarly stated, the detection module 5800 is coupled to the opposite side of the printed circuit board assembly 5630 than the flow member 5610. The detection module 5800 is configured to receive output from the amplification module 5600 (i.e., from the flow member 5610) and reagents from a reagent module (not shown) to produce an output to indicate presence or absence of target organism in the initial input sample. The detection module 5800 can also produce an output to indicate the general correct operation of the test (positive control and negative control). For example, in some embodiments, the detection module 5800 can produce one or more colorimetric outputs. The detection module 6800 can be any of the detection modules shown and described in International Patent Publication No. WO2016/109691, entitled "Devices and Methods for Molecular Diagnostic Testing," which is incorporated herein by reference in its entirety.

The detection module 5800 includes a detection flow cell that defines a detection chamber/channel 5812 having a series of inlet and outlet portions, through which the sample and the reagents are conveyed to produce the detected output. The detection chamber 5812 includes a "read lane" that includes one or more detection surfaces or zones. In some embodiments, the detection surfaces can be chemically modified to contain hybridization probes (i.e., single stranded nucleic acid sequences that capture complementary strand of target nucleic acid.) to capture complementary strands of the amplified nucleic acid. For example, in some embodiments, the read lane can include a first detection surface that includes a hybridization probe specific to *Neisseria* gonorrhea (NG), a second detection surface that includes a hybridization probe specific to *Chlamydia trachomatis* (CT), and a third detection surface that includes a hybridization probe specific to *Trichomonas vaginalis* (TV).

In use, the post-amplification solution (from the outlet portion 5622 of the flow member 5610) is conveyed into the detection chamber 5812. After the sample is in the detection chamber 5812, DNA strands in the post-amplification solution can bind to certain detection surfaces to facilitate production of the output signal. In some embodiments, to facilitate such binding, the detection module 5800 and/or the detection surfaces therein are heated via the fifth heater assembly 5669 to incubate the amplicon within the read lane (e.g., in the presence of a hybridizing probe). The independently controllable and isolated fifth heater assembly 5669 allows for accurate control of the temperature of the detection chamber 5812, and also allows for the fifth heater assembly 5669 to be activated at a different time than the other heater assemblies (e.g., after the PCR is completed).

After the amplicon hybridization has occurred, additional wash solutions and/or reagents can be conveyed through the detection module 5800 to facilitate the production of an output signal. The fifth heater assembly 5669 can heat the detection chamber 5812 (and the contents therein) at various stages of the detection cycle to further facilitate and/or enhance the production of the output signal.

Figure 15:
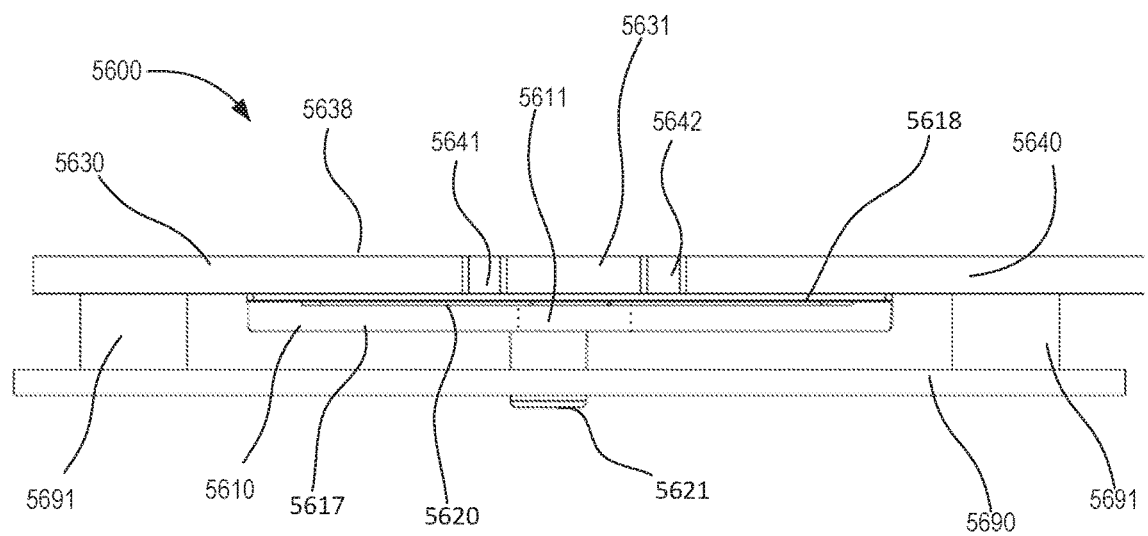
FIG. 15 is a side cross-sectional view of the of the amplification module shown in FIG. 5 taken along the line X-X in FIG. 5.

Referring to FIGS. 5 and 15, the heat sink 5690 is a thermally conductive material (e.g., aluminum) that is coupled to the circuit board assembly 5630 by a series of fasteners (not shown) that are coupled within the mounting openings (or vias) 5639 defined by the circuit board assembly 5630. The heat sink 5690 includes a series of offsets 5691 that are aligned with the openings 5639, and that maintain spacing between the heat sink 5690 and the flow member 5610. This arrangement allows for a consistent heat transfer path (or thermal coupling) between the circuit board assembly 5630 and the heat sink 5690 via the fasteners and the internal structure of the circuit board assembly 5630.

The heat transfer between the circuit board assembly 5630 and the heat sink 5690 is further facilitated by a series of conductive layers beneath and/or surrounding the second heater assembly 5660 and the third heater assembly 5670. The conductive layers provide a conductive path to facilitate heat transfer away from the second heater assembly 5660 and the third heater assembly 5670 to prevent overheating of the second heating zone 5632 and the third heating zone 5633, respectively. Referring to FIG. 11, the first layer 5646 of the circuit board assembly 5630 includes a first conductive region 5671 and a second conductive region 5672. The first conductive region 5671 (also referred to as a copper pour) surrounds, but is electrically isolated from the second heater assembly 5660. The second conductive region 5672 (also referred to as a copper pour) surrounds, but is electrically isolated from the third heater assembly 5670. The first conductive region 5671 and the second conductive region 5672 are thermally coupled to the mounting openings 5639 (or vias), and thus provide a low resistance thermal connection to the fasteners (not shown) that couple the printed circuit board assembly 5630 to the heat sink 5690. In this manner, the first conductive region 5671 and the second conductive region 5672 provide a conduction path to facilitate heat transfer away from the second heater assembly 5660 and the third heater assembly 5670 to prevent overheating of the second heating zone 5632 and the third heating zone 5633, respectively.

As shown in FIG. 12, the second layer 5647 of the circuit board assembly 5630 includes a first conductive region 5673 and a second conductive region 5674. The first conductive region 5673 (also referred to as a copper pour) is beneath, but is electrically isolated from the second heater assembly 5660. The second conductive region 5674 (also referred to as a copper pour) is beneath, but is electrically isolated from the third heater assembly 5670. The first conductive region 5673 and the second conductive region 5674 are thermally coupled to the mounting openings 5639 (or vias), and thus provide a low resistance thermal connection to the fasteners (not shown) that couple the printed circuit board assembly 5630 to the heat sink 5690. In this manner, the first conductive region 5673 and the second conductive region 5674 provide a conduction path to facilitate heat transfer away from the second heater assembly 5660 and the third heater assembly 5670 to prevent overheating of the second heating zone 5632 and the third heating zone 5633, respectively. Further, in this embodiment, the portion of the second layer 5647 that is aligned with (or beneath) the first heater assembly 5650 is devoid of a conductive material or copper pour. Because the first heater assembly 5650 is configured to operate at higher temperatures than either the second heater assembly 5660 or the third heater assembly 5670, an additional conduction path to facilitate heat transfer away from the first heating zone 5631 is not desired. In other embodiments, however, any suitable layer of a printed circuit board can include conductive layers (or copper pour layers) beneath and/or aligned with any of the heater assemblies and/or heating zones.

As shown in FIG. 13 the third layer 5648 of the circuit board assembly 5630 includes a first conductive region 5675 and a second conductive region 5676. The first conductive region 5675 (also referred to as a copper pour) is beneath, but is electrically isolated from the second heater assembly 5660. The second conductive region 5676 (also referred to as a copper pour) is beneath, but is electrically isolated from the third heater assembly 5670. The first conductive region 5675 and the second conductive region 5676 are thermally coupled to the mounting openings 5639 (or vias), and thus provide a low resistance thermal connection to the fasteners (not shown) that couple the printed circuit board assembly 5630 to the heat sink 5690. In this manner, the first conductive region 5675 and the second conductive region 5676 provide a conduction path to facilitate heat transfer away from the second heater assembly 5660 and the third heater assembly 5670 to prevent overheating of the second heating zone 5632 and the third heating zone 5633, respectively. Further, in this embodiment, the portion of the third layer 5648 that is aligned with (or beneath) the first heater assembly 5650 is devoid of a conductive material or copper pour. Because the first heater assembly 5650 is configured to operate at higher temperatures than either the second heater assembly 5660 or the third heater assembly 5670, an additional conduction path to facilitate heat transfer away from the first heating zone 5631 is not desired. In other embodiments, however, any suitable layer of a printed circuit board can include conductive layers (or copper pour layers) beneath and/or aligned with any of the heater assemblies and/or heating zones.

As shown in FIG. 14, the fourth layer 5649 of the circuit board assembly 5630 includes a first conductive region 5677 and a second conductive region 5678. The first conductive region 5677 (also referred to as a copper pour) is beneath, but is electrically isolated from the second heater assembly 5660. The second conductive region 5678 (also referred to as a copper pour) is beneath, but is electrically isolated from the third heater assembly 5670. The first conductive region 5677 and the second conductive region 5678 are thermally coupled to the mounting openings 5639 (or vias), and thus provide a low resistance thermal connection to the fasteners (not shown) that couple the printed circuit board assembly 5630 to the heat sink 5690. In this manner, the first conductive region 5677 and the second conductive region 5678 provide a conduction path to facilitate heat transfer away from the second heater assembly 5660 and the third heater assembly 5670 to prevent overheating of the second heating zone 5632 and the third heating zone 5633, respectively. Further, in this embodiment, the portion of the fourth layer 5649 that is aligned with (or beneath) the first heater assembly 5650 is devoid of a conductive material or copper pour. Because the first heater assembly 5650 is configured to operate at higher temperatures than either the second heater assembly 5660 or the third heater assembly 5670, an additional conduction path to facilitate heat transfer away from the first heating zone 5631 is not desired. In other embodiments, however, any suitable layer of a printed circuit board can include conductive layers (or copper pour layers) beneath and/or aligned with any of the heater assemblies and/or heating zones.

As shown in FIGS. 11-14, the conductive regions for each layer of the printed circuit board assembly 5630 are discontinuous (segmented). Specifically, the first (or hot) heating zone 5631 is devoid of a conductive region, because the higher operating temperatures of the first heating zone 5631 do not necessitate a conductive region to facilitate heat transfer away from the first heating assembly 5650. Similarly stated, the first heating zone 5631 is devoid of a conductive region to keep the thermal energy localized and to prevent it from spilling over into the other heating zones. In other embodiments, however, a printed circuit board assembly can include one or more conductive regions surrounding and/or beneath any of the heating zones.

Moreover, in some embodiments, one or more additional conductive regions can be included in any layer of the printed circuit board assembly 5630 to facilitate reduction of electromagnetic interference conveyed to any components on the printed circuit board assembly 5630 (e.g. a controller, a processor, or the like).

The printed circuit board assembly 5630 includes a series of temperature sensors that provide feedback to enable control of the heater assemblies described herein. Specifically, as shown in FIG. 14, the fourth layer 5649 of the printed circuit board assembly 5630 includes a first series of temperature sensors 5680 disposed beneath each of the heating elements of the first heater assembly 5650, a second series of temperature sensors 5681 disposed beneath each of the heating elements of the second heater assembly 5660, a third series of temperature sensors 5682 disposed beneath each of the heating elements of the third heater assembly 5670, and a fourth temperature sensor 5683 disposed beneath the fourth heater assembly 5668. The temperature sensors can be any suitable sensor, such as a thermistor, thermocouple or the like. Moreover, although the temperature sensors are shown as being fabricated in the fourth layer 5649, in other embodiments, the temperature sensors can be fabricated in any layer of the circuit board assembly 5630.

As shown in FIG. 11, the first layer 5646 of the printed circuit board assembly 5630 includes a detection temperature sensor 5684 disposed beneath the fifth heater assembly 5669. The detection temperature sensor 5684 can be any suitable sensor, such as a thermistor, thermocouple or the like. Moreover, although the detection temperature sensor 5684 is shown as being fabricated in the first layer 5646, in other embodiments, the temperature sensors can be fabricated in any layer of the circuit board assembly 5630.

In some embodiments, the amplification module 5600 (and any of the amplification modules described herein) can include a power source (not shown) and a controller (not shown). The power source can be any suitable power source to power the amplification module 5600. In some embodiments, power source can include an on-board AC converter that receives AC power and converts the power to a level suitable for supplying current to the heater assemblies. In other embodiments, the power source can be a DC power source (e.g., a battery) coupled to the printed circuit board assembly 5630. For example, in some embodiments, the amplification module 5600 (and the diagnostic device within which it is disposed) is configured for a single use. In such embodiments, the power source can have a capacity sufficient for only one test. In some embodiments, for example, the power source is a battery having a nominal voltage of about 9 VDC and a capacity of less than about 1200 mAh. In other embodiments, the power source can include multiple DC batteries, such as, for example, multiple 1.5 VDC cells (e.g., AAA or AA alkaline batteries).

The controller can be coupled to the printed circuit board assembly 5630, and can control the timing and amount of current supplied from the power source to each of the heater assemblies included in the printed circuit board assembly 5630. In some embodiments, the controller can also include a temperature feedback module (not shown) that receives temperature signal from the temperature sensors described above (e.g., the temperature sensors 5680). The temperature feedback module includes circuitry, components, and/or code to produce a control signal that can facilitate controlling current to the heater assemblies. In some embodiments, the controller 1500 can also include a flow module (not shown) that receives information associated with flow of the sample through the amplification module 5600 (and the diagnostic device within which the amplification module 5600 is employed). The controller can be coupled to a computer (not shown) or other input/output device via the input/output module (or interface).

Figure 18:
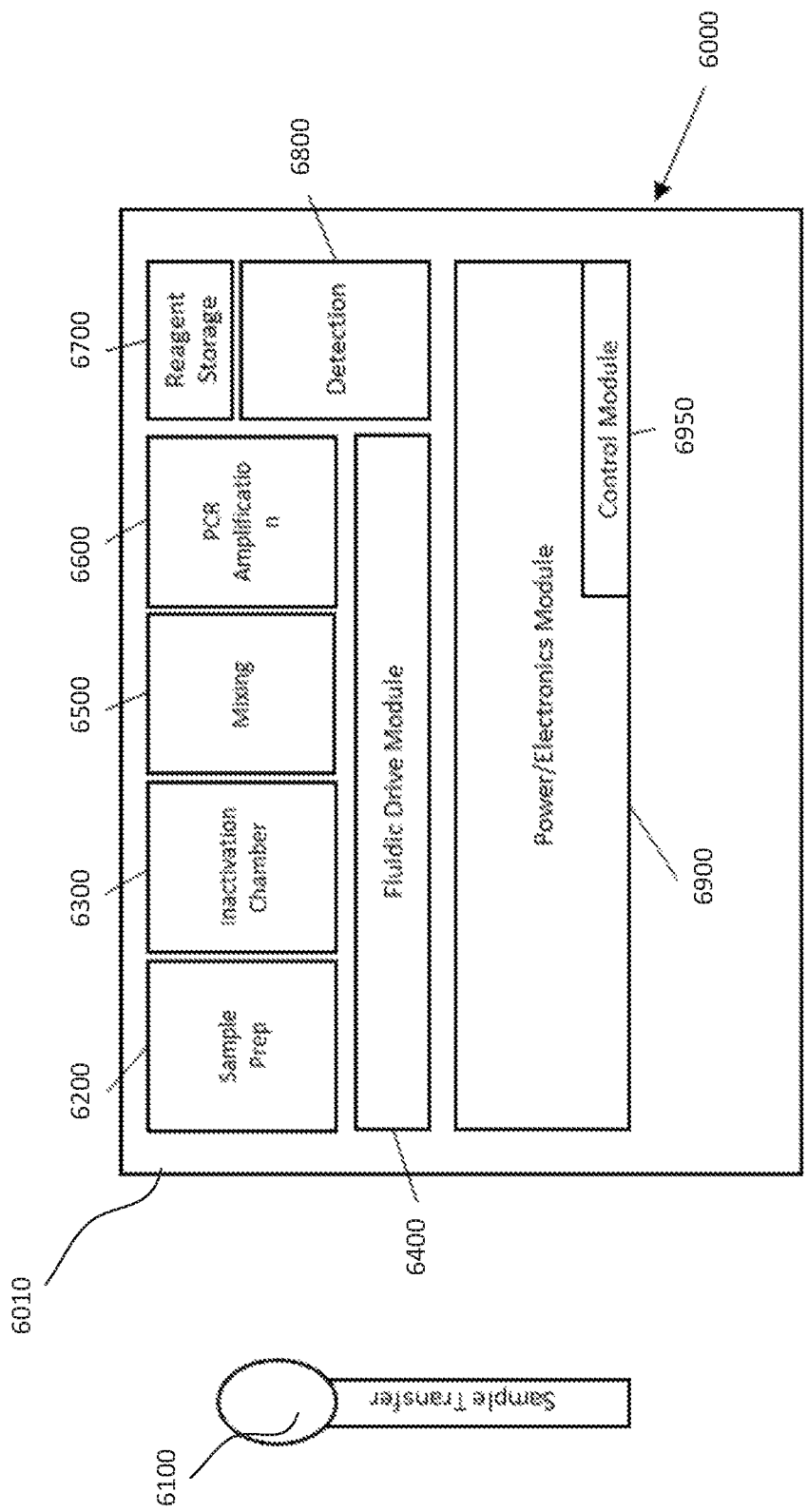
FIG. 18 is a schematic illustration of a molecular diagnostic device, according to an embodiment.
Figure 19:
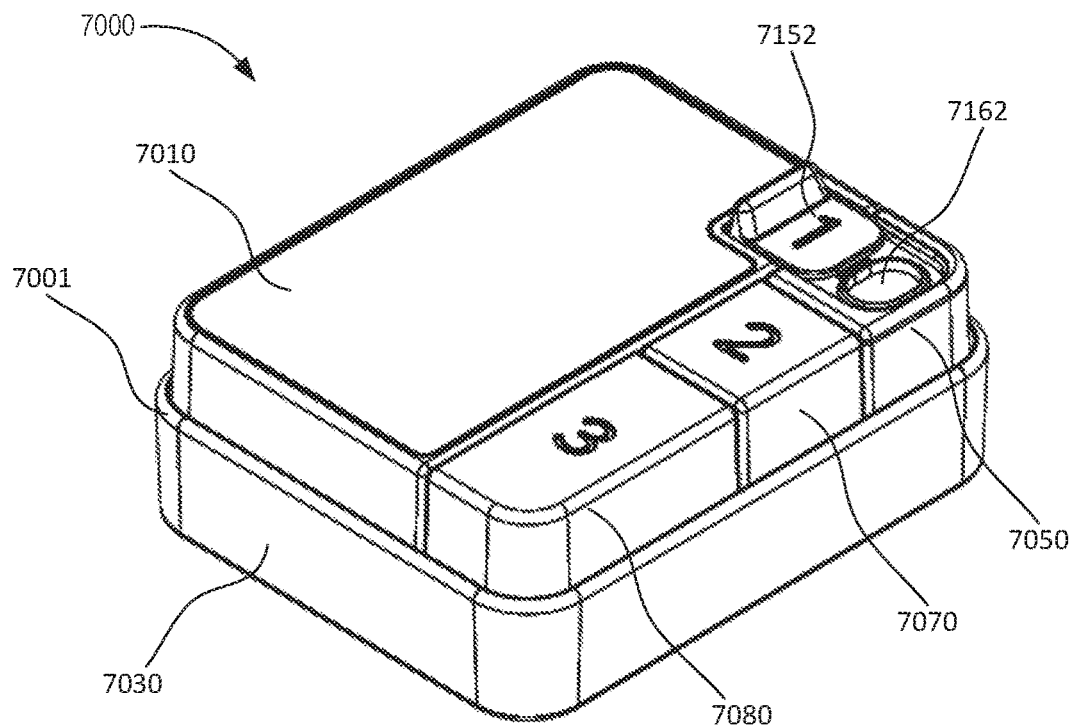
FIG. 19 is a perspective view of a molecular diagnostic device, according to an embodiment.

The amplification module 5600 (and any of the amplification module described herein) can be used within any suitable diagnostic device, such as in any of the diagnostic devices shown and described in International Patent Publication No. WO2016/109691, entitled "Devices and Methods for Molecular Diagnostic Testing," which is incorporated herein by reference in its entirety. One example of an integrated test device is shown in FIG. 18, which is a schematic block diagram of a molecular diagnostic system 6000 (also referred to as "system" or "diagnostic device"), according to an embodiment. The diagnostic device 6000 is configured to manipulate a sample to produce an optical indication associated with a target cell according to any of the methods described herein. In some embodiments, the diagnostic device 6000 can be a single-use, disposable device that can provide an optical output without need for any additional instrument to manipulate or otherwise condition the diagnostic device 6000. Said another way, the diagnostic device 6000 is an integrated cartridge/instrument, and the entire unit can be used to perform a diagnostic assay and then be disposed. The diagnostic device 6000 includes a sample transfer device 6100, a sample preparation module 6200, an inactivation chamber 6300, a fluidic drive module 6400, a mixing chamber 6500, an amplification module 6600, a reagent storage module 6700, a detection module 6800, a power/electronics module 6900, and a control module 6950. A brief description of the major subsystems of the diagnostic device 6000 is provided below.

The sample transfer device 6100 is configured to transport a sample such as, for example, a blood, urine, male urethral specimens, vaginal specimens, cervical swab specimens, and/or nasal swab specimens sample gathered using a commercially available sample collection kit, to the sample preparation module 6200. The sample collection kit can be a urine collection kit or swab collection kit. Non-limiting examples of such sample collection kits include Copan Mswab or BD ProbeTec Urine Preservative Transport Kit, Cat #440928, neat urine. The sample transfer device 6100 dispenses and/or otherwise transfers an amount of sample or sample/media to the sample preparation module 6200 through an input port (not shown). The input port can then be capped. In some embodiments, the sample transfer device 6100 can be locked and/or fixedly coupled to the sample preparation module 6200 as a part of the dispensing operation. In this manner, the interface between the sample transfer device 6100 and the sample preparation module 6200 can be configured to prevent reuse of the diagnostic device 6000, transfer of additional samples, or the like. Although shown as including the sample transfer device 6100, in other embodiments, the diagnostic device 6000 need not include a sample transfer device.

In some embodiments, through a series of user actions or in an automated/semi-automated matter, the sample preparation module 6200 is configured to process the sample. For example, the sample preparation module 6200 can be configured to concentrate and lyse cells in the sample, thereby allowing subsequent extraction of DNA. In some embodiments, the processed/lysed sample is pushed and/or otherwise transferred from the sample preparation module 6200 to the inactivation chamber 6300, which is configured to inactivate, in the lysed sample, the proteins used during lysing. In some embodiments, the fluidic drive module 6400 is configured to aspirate the sample from the inactivation chamber 6300, and is further configured to convey the sample to the amplification module 6600. The fluidic drive module 6400 is also configured to convey the sample and/or reagents (e.g., from the reagent storage module 6700) to perform any of the methods of diagnostic testing described herein. Similarly stated, the fluidic drive module 6400 is configured to generate fluid pressure, fluid flow and/or otherwise convey the input sample through the modules of the device.

The mixing chamber 6500 mixes the output of inactivation chamber 6300 with the reagents necessary to conduct a PCR reaction. In some embodiments, the mixing chamber 6500 can contain the PCR reagents in the form of one or more lyophilized reagent beads that contain the primers and enzymes necessary for PCR. In such embodiments, the mixing chamber 6500 can be configured to hydrate and/or reconstitute the lyophilized beads in a given input volume, while ensuring even local concentrations of reagents in the entirety of the volume. The mixing chamber 6500 can include any suitable mechanism for producing the desired solution, such as, for example, a continuous flow mixing channel, an active mixing element (e.g., a stir rod) and/or a vibratory mixing element. The mixed sample is then conveyed to the amplification module 6600 (e.g., by the fluidic drive module 6400).

The amplification module 6600 is configured to run polymerase chain reaction (PCR) on the sample to generate an amplified sample, in any manner as described herein. For example, in some embodiments, the amplification module 6600 can be similar to the amplification module 5600 (or any other amplification module described herein). After PCR, the amplified sample is further pushed, transferred or conveyed to a detection module 6800. In some embodiments, the detection module 6800 is configured to run and/or facilitate a colorimetric enzymatic reaction on the amplified sample. In particular, a series of reagents from the reagent storage module 6700 can be conveyed by the fluidic drive module 6400 to facilitate the optical output from the test. In some embodiments, the various modules/subsystems of the main diagnostic device 6000 are controlled and/or powered by the power/electronics module 6900 and the control module 6950.

In some embodiments, the control module 6950 can include one or more modules, and can automatically control the valves, pumps, power delivery and/or any other components of the diagnostic device 6000 to facilitate the molecular testing as described herein. The control module 6950 can include a memory, a processor, an input/output module (or interface), and any other suitable modules or software to perform the functions described herein.

Although the printed circuit board (or heater) assembly 5630 is shown and described as including a series of heater assemblies (i.e., the first heater assembly 5650, the second heater assembly 5660, and the third heater assembly 5670) fabricated with and/or coupled to a first (or outer) layer of the printed circuit board assembly 5630, in other embodiments, a printed circuit board (or heater) assembly can include heater assemblies and/or heating elements within any suitable layer or portion of the circuit board. For example, in some embodiments, a printed circuit board (or heater) assembly can include one or more heating elements within an inner layer. Such an arrangement can, for example, allow the thickness of lithographically produced heating elements to be controlled and/or set to a desired value. This, in turn, can allow the resistance of the heating element to be set to a desired value. Moreover, including the heating elements within an inner layer can reduce the amount of electromagnetic field (EMF) noise to which the other electronic components on the printed circuit board assembly (e.g., processors and/or controllers) are exposed. Specifically, the placement of the heating elements within the printed circuit board assembly can limit the amount of noise generated by the high return current (i.e., "ground noise") to which the processors and/or controllers are exposed.

Moreover, although the amplification assembly 5600 is shown and described as including a single heat sink (i.e., the heat sink 5690), in other embodiments, any of the amplification assemblies described herein can include any suitable heat sink and/or thermal management arrangement.

For example, FIGS. 19-25 show various views of a molecular diagnostic test device 7000 (also referred to as a "test device" or "device") within which any of the amplification modules described herein can be included. The test device 7000 can be similar to, and can contain any of the structure as, the molecular diagnostic test device 6000 or any other molecular diagnostic test devices shown and described in International Patent Publication No. WO2016/109691, entitled "Devices and Methods for Molecular Diagnostic Testing" ("the '691 PCT Application") which is incorporated herein by reference in its entirety. In particular, the test device 7000 is an integrated device (i.e., the modules are contained within a single housing) that is suitable for use within a point-of-care setting (e.g., doctor's office, pharmacy or the like), decentralized test facility, or at the user's home. In some embodiments, the device 7000 can have a size, shape and/or weight such that the device 7000 can be carried, held, used and/or manipulated in a user's hands (i.e., it can be a "handheld" device). In other embodiments, the test device 7000 can be a self-contained, single-use device. Similarly stated, in some embodiments, the test device 7000 can be configured with lock-outs or other mechanisms to prevent re-use or attempts to re-use the device.

Further, in some embodiments, the device 7000 can be a CLIA-waived device and/or can operate in accordance with methods that are CLIA waived. Similarly stated, in some embodiments, the device 7000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 7000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 7000 can be configured for long term storage in a manner that poses a limited likelihood of misuse (spoilage of the reagent(s), expiration of the reagents(s), leakage of the reagent(s), or the like). In some embodiments, the molecular diagnostic test device 7000 is configured to be stored for up to about 36 months, up to about 32 months, up to about 26 months, up to about 24 months, up to about 20 months, up to about 18 months, or any values there between.

The test device 7000 is configured to manipulate an input sample to produce one or more output signals associated with a target cell, according to any of the methods described herein. FIGS. 10 and 11 show perspective views of the molecular diagnostic test device 7000. The diagnostic test device 7000 includes a housing 7001 (including a top portion 7010 and a bottom portion 7030), within which a variety of modules are contained. Specifically, the device 7000 includes a sample preparation module (not shown, but which is similar to the sample preparation module 6200 described herein or in the '691 PCT Application), an inactivation module (not shown, but which is similar to the inactivation module 6300 described herein or in the '691 PCT Application), a fluidic drive (or fluid transfer) module (not shown, but which is similar to the fluidic drive module 6400 described herein or in the '691 PCT Application), a mixing chamber (not shown, but which is similar to the mixing chamber 6500 described herein or in the '691 PCT Application), an amplification module 7600, a detection module 7800, a reagent storage module (not shown, but which is similar to the reagent storage module 6700 described herein or in the '691 PCT Application), and a power and control module 7900.

Figure 20:
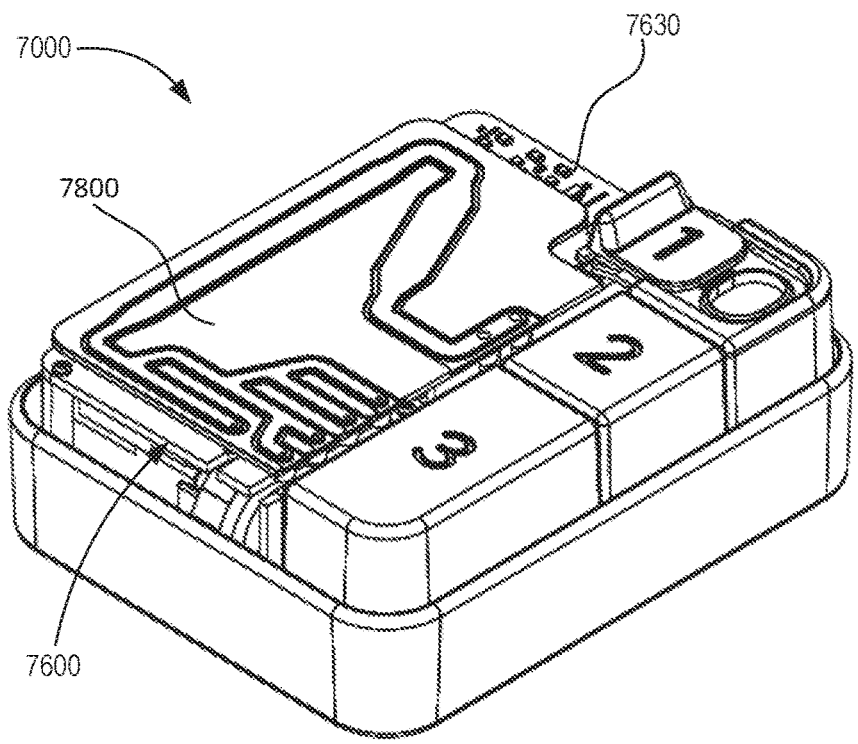
FIG. 20 is a perspective view of a molecular diagnostic device shown in FIG. 19 with a portion of the housing removed.
Figure 21:
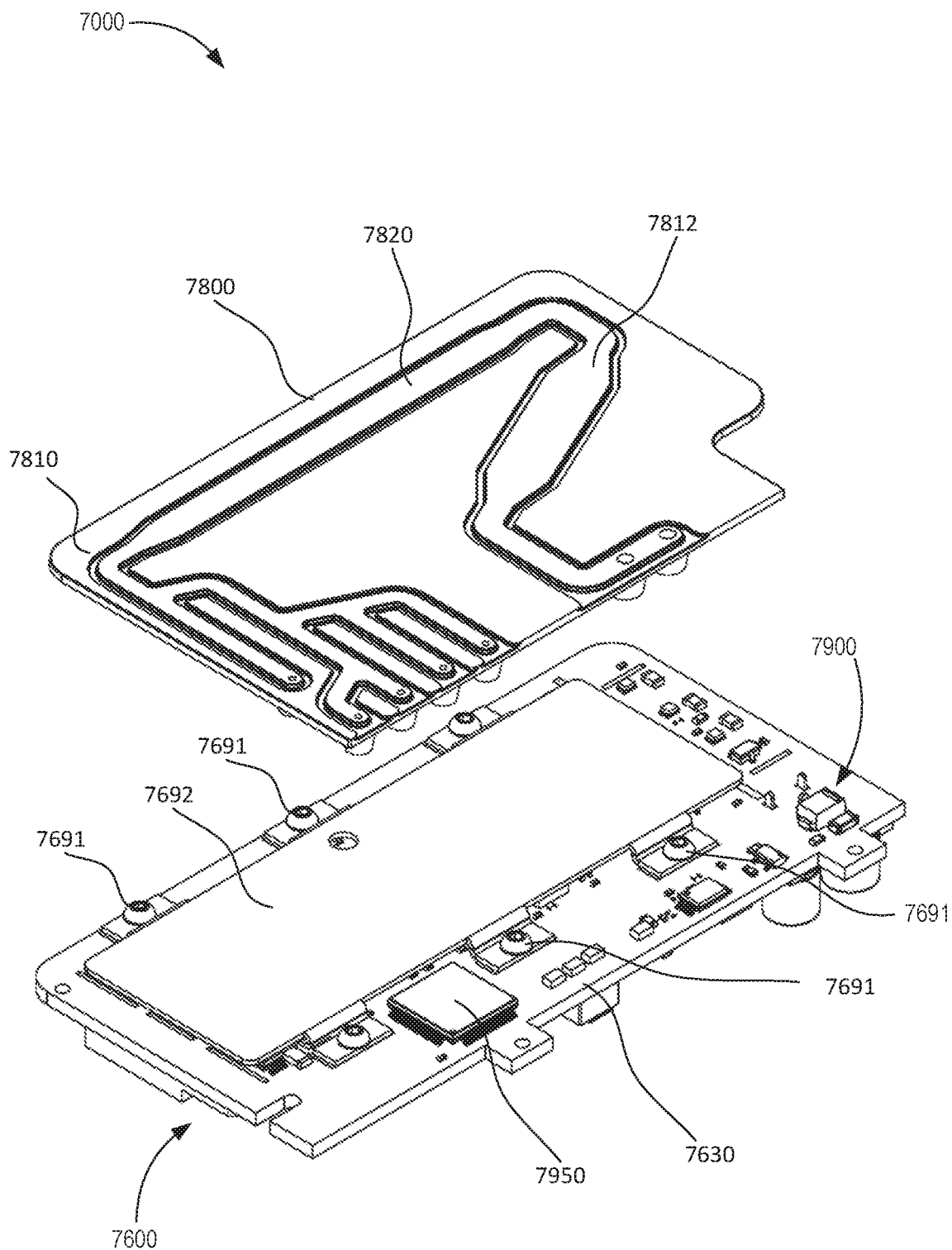
FIG. 21 is an exploded perspective view of a detection module and an amplification module of the molecular diagnostic device shown in FIGS. 19 and 20.

The lower housing 7030 defines a volume 7032 within which the modules and or components of the device 7000 are disposed. The top housing 7010 covers and/or surrounds at least a portion of the lower housing 7030. FIG. 20 shows the device 7000 with the top housing 7010 removed so that the placement of the modules can be seen. In some embodiments, the top housing 7010 can define a series of detection (or "status") openings that allow the user to visually inspect the output signal(s) produced by the device 7000. In such embodiments, when the top housing 7010 is coupled to the lower housing 7030, the detection openings are aligned with the corresponding detection surfaces of the detection module 7800 such that the signal produced by and/or on each detection surface is visible through the corresponding detection opening.

Although not described in detail herein, the sample preparation module includes any or all of a sample input portion (or module), a wash portion (or module), an elution portion (or module), a filter portion (or module), and various fluidic conduits (e.g., tubes, lines, valves, etc.) connecting the various components. The input sample can be conveyed into the test device 7000 by moving the cap 7152 and depositing the sample into the input opening 7162. The sample preparation module is at least partially actuated by depressing the first actuator (or button) 7050. In some embodiments, the first actuator 7050 includes tabs, locks, or the like that prevent the user from reusing the first actuator 7050 and/or the device 7000 after an initial use has been attempted and/or completed. Further aspects of the sample preparation module (e.g., the elution portion or the filter portion) can be actuated by depressing the second actuator (or button) 7070. In some embodiments, the second actuator 7070 includes tabs, locks, or the like that prevent the user from reusing the second actuator 7070 and/or the device 7000 after an initial use has been attempted and/or completed. The reagent storage module and/or other aspects of the test device 7000 (including the power and control module 7900) can be actuated by depressing the third actuator (or button) 7080. In some embodiments, the third actuator 7080 includes tabs, locks, or the like that prevent the user from reusing the third actuator 7080 and/or the device 7000 after an initial use has been attempted and/or completed. Moreover, in some embodiments, the first actuator 7050, the second actuator 7070, and the third actuator can include tabs, locks, or other structure to control the order of operation of the actuators.

Figure 22:
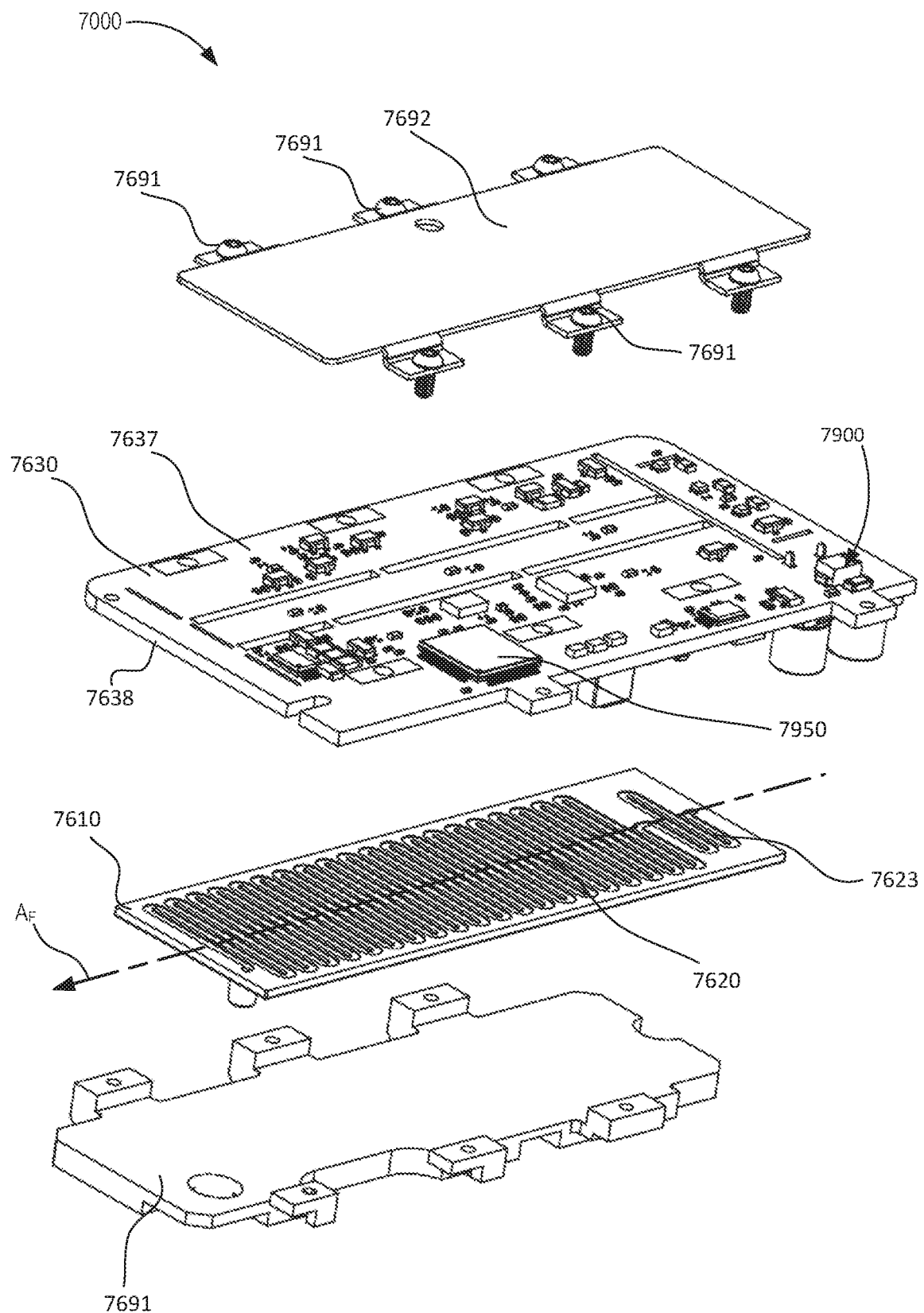
FIG. 22 is an exploded perspective view of the amplification module shown in FIG. 21.

The amplification module 7600 is configured to perform a thermal reaction (e.g., an amplification reaction) on an input of target nucleic acid mixed with required reagents. Referring to FIG. 22, the amplification module 7600 includes a flow member 7610, a circuit board (or heater) assembly 7630, a first (or lower) heat sink 7690, and a second (or upper) heat sink 7692. The flow member 7610 is coupled between the circuit board assembly 7630 and the first heat sink 7690. The flow member 7610 has the same structure and function as the flow member 6610 described above, and is therefore not described in detail below. In particular, the flow member defines a flow path 7620 through which a sample can flow from an inlet port to an outlet port. The flow member 7620 defines a flow axis $A_F$ that indicates the overall direction of the flow through the flow member 7610. As shown, the amplification flow path has a curved, switchback or serpentine pattern. More specifically, the flow member (or chip) 7610 has two serpentine patterns—an amplification pattern and a hot-start pattern 7623. The amplification pattern allows for amplification (i.e., PCR in this instance) to occur while the hot-start pattern 7623 accommodates the hot-start conditions of the PCR enzyme.

As shown, the serpentine pattern establishes 40 different zones of "cold-to-hot-to-cold;" or 40 amplification cycles. In other embodiments, however, the flow member 7610 (or any of the other flow members described herein) can define any suitable number of switchbacks or amplification cycles to ensure the desired test sensitivity. In some embodiments, the flow member can define at least 30 cycles, at least 34 cycles, at least 36 cycles, at least 38 cycles, or at least 40 cycles. The dimensions of the flow channel 7620 in the flow member 7610 impact the temperature conditions of the PCR and dictate the overall dimensions of the chip, and thus affect the overall power consumption of the amplification module 7600. For example, a deeper, narrower channel will develop a larger gradient in temperature from the side closest to the lid 7619 to the bottom (resulting in lower PCR efficiency). This arrangement, however, requires less overall space since the channels will take up less overall surface area facing the heater assembly 7630 (and thus require less energy to heat). The opposite holds true for a wide and shallow channel. In some embodiments, the depth of the flow channel 7620 is about 0.15 mm and the width of the flow channel 7620 is between about 1.1 mm and about 1.3 mm. More particularly, in some embodiments, the flow channel 7620 has a width of about 1.1 mm in the "narrow" sections (that are within the second temperature zone 7612 and the third temperature zone 7613) and about 1.3 mm in the "wide" section (that falls within the first temperature zone 7611). In some embodiments, the overall path length is about 960 mm (including both the amplification portion and the hot start portion 7623). In such embodiments, the total path length of the amplification portion is about 900 mm. This produces a total volume of the flow channel 7620 of about 160 µl (including the hot start portion 7623) and about 150 µl (without the hot start portion 7623). In some embodiments, the separation between each parallel path is between about 0.4 mm and about 0.6 mm.

The flow member 7610 can be constructed from any suitable material, and can have any suitable thickness. For example, in some embodiments, the flow member 7610 (and any of the flow members described herein) can be molded from COC (Cyclic Olefin Copolymer) plastic, which has inherent barrier properties and low chemical interactivity. In other embodiments, the flow member 7610 (and any of the flow members described herein) can be constructed from a graphite-based material (for improved thermal properties). The overall thickness of the flow member 7610 can be less than about 0.5 mm, less than about 0.4 mm, less than about 0.3 mm or less than about 0.2 mm.

The flow member 7610 can be coupled to the circuit board assembly 7630 in any suitable manner. For example, in some embodiments, the flow member 7610 can be coupled to the heater assembly 7630 at least in part by the mechanical fasteners 7691 used to couple the first heat sink 7690 and the second heat sink 7692 to the circuit board assembly 7630. In some such embodiments, the fasteners 7691 can also function as heat sinks (or conduits) to allow accurate control of the temperatures of the flow member 7610 and to avoid overheating. In other embodiments, the flow member 7610 can be coupled to the heater assembly 7630 by an adhesive (e.g., a pressure-sensitive adhesive). Similarly stated, in some embodiments, the flow member 7610 can be chemically bonded to the heater assembly 7630. Thus, the flow member 7610 can be fixedly and irreversibly coupled to the heater assembly 7630. Said another way, in some embodiments, the flow member 7610 is not designed to be removed and/or decoupled from the heater assembly 7630 during normal use. This arrangement facilitates the test device 7000 being a single-use, disposable device.

Figure 24:
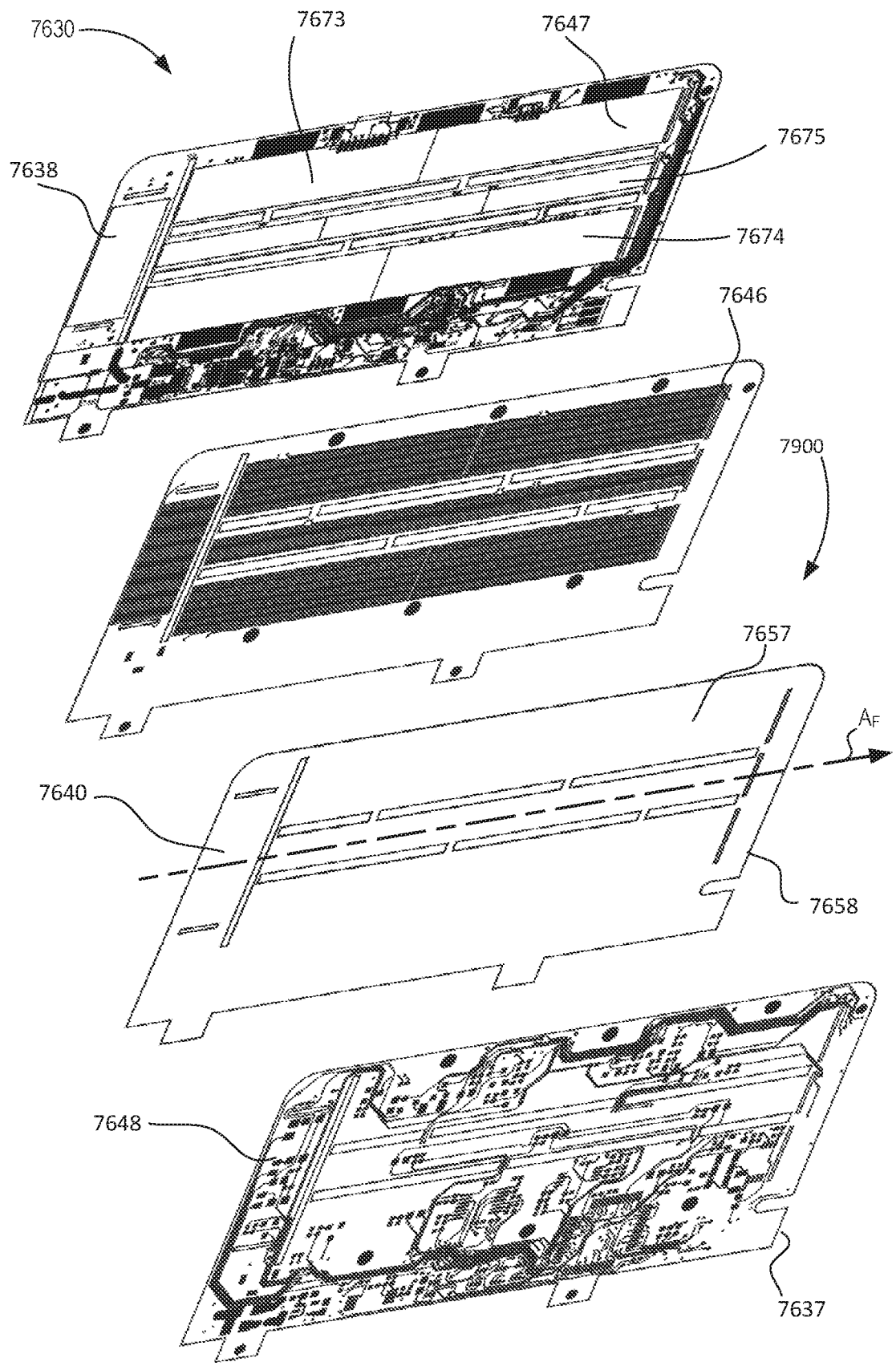
FIG. 24 is an exploded perspective view of the printed circuit board shown in FIG. 23.

The circuit board (or heater) assembly 7630 is a multilayer circuit board having a first side 7637 and a second side 7638. FIG. 24 shows an exploded view of various layers of the circuit board assembly 7630, including certain copper traces fabricated thereon. Although FIG. 24 shows a substrate and three layers, in some embodiments, a thin film substrate (not shown) separates adjacent layers. In other embodiments, a circuit board assembly can include any suitable number of layers. For example, the circuit board assembly 7630 (and any other circuit board assemblies described herein) can include one or more layers having conductive regions similar to the conductive regions 5671, 5672 shown and described above with reference to the circuit board assembly 5630.

Specifically, at least the second (or outer bottom) layer 7647 includes a first conductive region 7675, a second conductive region 7673, and a third conductive region 7674. The first conductive region 7675 (also referred to as a copper pour) is beneath, but is electrically isolated from the first heater assembly 7650. The inclusion of the first conductive region 7675 is different than the design shown above for the amplification module 5600, in which the portion of the second layer 5647 aligned with (or beneath) the first heater assembly 5650 is devoid of a conductive material or copper pour. Here, the first conductive region 7675 is isolated from the other conductive regions, and provides accurate control of the temperatures in the first region. The second conductive region 7673 (also referred to as a copper pour) is beneath, but is electrically isolated from the second heater assembly 7660. The third conductive region 7674 (also referred to as a copper pour) is beneath, but is electrically isolated from the third heater assembly 7670. The second conductive region 7673 and the third conductive region 7674 are thermally coupled to the mounting openings, and thus provide a low resistance thermal connection to the fasteners (not shown) that couple the printed circuit board assembly 7630 to the first heat sink 7690 and/or the second heat sink 7692. In this manner, the conductive regions provide a conduction path to facilitate heat transfer away from the first heater assembly 7650, the second heater assembly 7660 and the third heater assembly 7670.

Moreover, in addition to including the heater assemblies as described herein, the circuit board assembly 7630 is also coupled to and/or supports the processor 7950, and other electronic components of the power and control module 7900. Thus, the circuit board (or heater) assembly 7630 performs and/or facilitates the performance of many different electronic functions, including controlling the amplification of the sample, controlling sample movement, and other thermally-based functions described herein.

As shown, the circuit board assembly 7630 includes a substrate 7640 having a first side 7657 and a second side 7658, a first (or heater) layer 7646, a second (or outer bottom) layer 7647, and a third (or outer top) layer 7648. The substrate 7640 provides structural support, and is constructed from an electrically isolative material upon which the four layers are fabricated using lithographic procedures. The substrate 7640 (and any of the substrates described herein) can be constructed from any suitable material, such as, for example, a composite material including woven glass and epoxy. In some embodiments, the substrate 7640 (and any of the substrates described herein) can be constructed from a material having a glass transition temperature (Tg) of greater than about 170 C. In other embodiments, the substrate 7640 (and any of the substrates described herein) can be constructed from a material having a glass transition temperature (Tg) of greater than about 180 C (e.g., material 370HR produced by the Isola Group). In this manner, the substrate 7640 can maintain the desired rigidity and dimensional integrity to provide repeatable thermal performance for each channel of the flow path 7620.

Referring again to FIG. 23, the circuit board assembly 7630 defines a series of apertures (also referred to as openings, cut-outs, or vias) that separate the circuit board assembly 7630 into several different portions (or heating zones). Specifically, the circuit board assembly 7630 defines a first set of apertures 7641 that separates a first portion (or heating zone) 7631 of the assembly 7630 from a second portion (or heating zone) 7632 of the assembly 7630. The first set of apertures 7641 includes three openings that are elongated along the flow axis $A_F$, and that are separated by two connection lugs 7651. Thus, the first set of apertures 7641 produces a longitudinally oriented thermal barrier between the first heating zone 7631 and the second heating zone 7632. Similarly, the circuit board assembly 7630 defines a second set of apertures 7642 that separates the first portion (or heating zone) 7631 of the assembly 7630 from a third portion 7633 (or heating zone) of the assembly 7630. The second set of apertures 7642 includes three openings that are elongated along the flow axis $A_F$, and that are separated by two connection lugs 7652. Thus, the second set of apertures 7642 produces a longitudinally oriented thermal barrier between the first heating zone 7631 and the third heating zone 7633.

Figure 25:
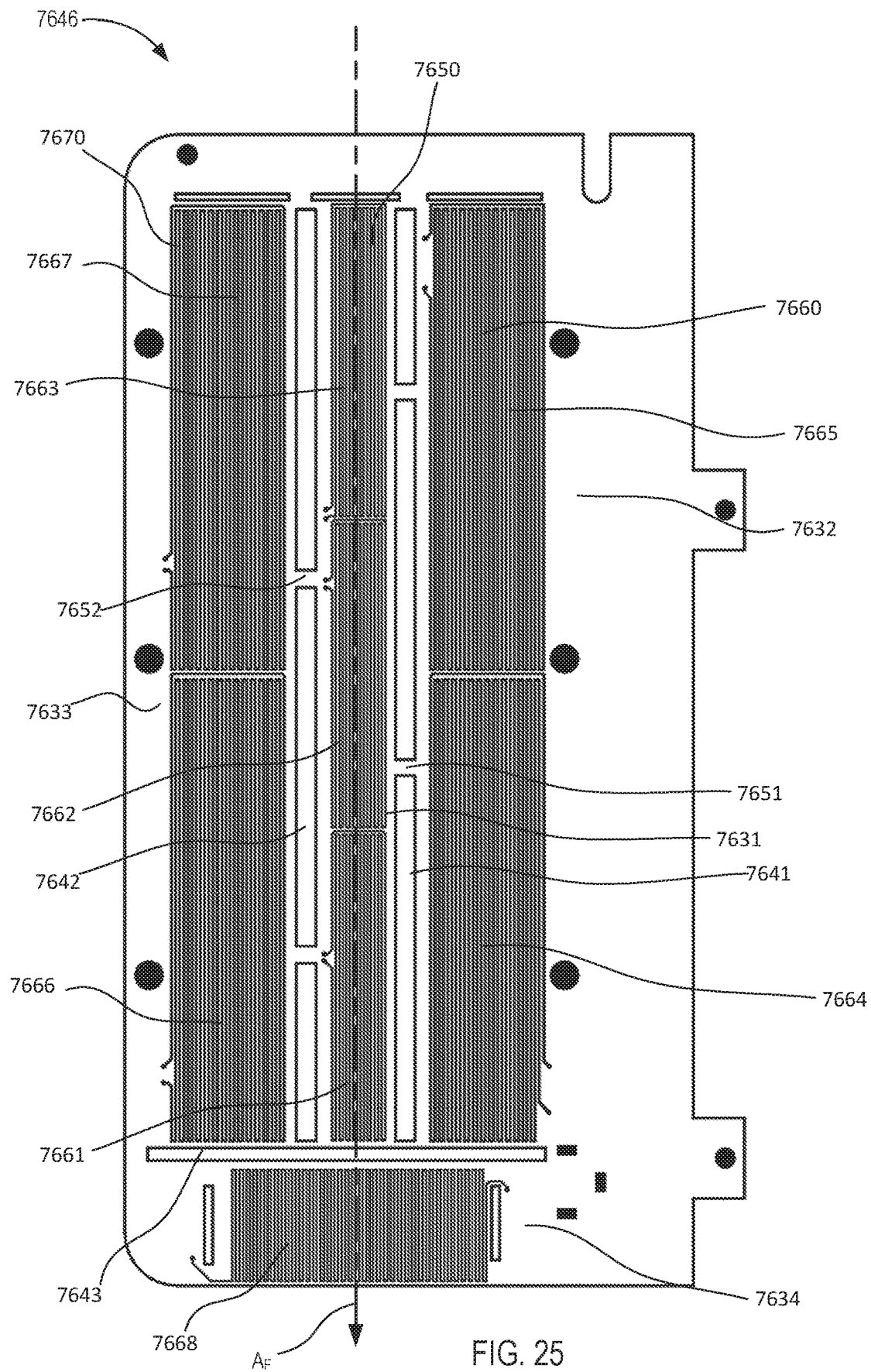
FIG. 25 is a bottom view of a heater layer of the printed circuit board shown in FIG. 23.

The first heating zone 7631 is disposed between the second heating zone 7632 and the third heating zone 7633. Moreover, like the arrangement of the circuit board assembly 5630 described above, when the circuit board assembly 7630 is coupled to the flow member 7610, the first heating zone 7631 is aligned with a first (or "hot") temperature zone of the flow member 7610, the second heating zone 7632 is aligned with a second (or "cold") temperature zone of the flow member 7610, and the third heating zone 7633 is aligned with a third (or "cold") temperature zone of the flow member 7610. Referring to FIG. 25, this arrangement allows the first heater assembly 7650 located within first heating zone 7631 to heat the first temperature zone (or central portion) of the flow member 7610. This arrangement further allows the second heater assembly 7660 located within second heating zone 7632 to heat the second temperature zone (or side portion) of the flow member 7610. This arrangement further allows the third heater assembly 7670 located within third heating zone 7633 to heat the third temperature zone (or opposite side portion) of the flow member 7610. In this manner, the heater assembly 7630 and the flow member 7610 can establish multiple temperature zones through which a sample can flow, and can define a desired number of amplification cycles to ensure the desired test sensitivity (e.g., at least 30 cycles, at least 34 cycles, at least 36 cycles, at least 38 cycles, or at least 40 cycles).

As shown in FIG. 25, the first heater assembly 7650 includes a first heating element 7661, a second heating element 7662, and a third heating element 7663, each of which is electrically isolated from the other two heating elements in the first heater assembly 7650. Said another way, each of the first heating element 7661, the second heating element 7662, and the third heating element 7663 is separate from (or electrically isolated from) the others. In this manner, an electrical current can be conveyed to each of the first heating element 7661, the second heating element 7662, and the third heating element 7663 independently from an electrical current being conveyed to the other heating elements of the first heater assembly 7650. This arrangement allows for independent control of the first heating element 7661, the second heating element 7662, and the third heating element 7663. The second heater assembly 7660 includes a first heating element 7664 and a second heating element 7665, each being electrically isolated from the other. Said another way, the first heating element 7664 is separate from the second heating element 7665, and vice-versa. In this manner, an electrical current can be conveyed to the first heating element 7664 independently from an electrical current being conveyed to the second heating element 7665, and vice-versa. This arrangement allows for independent control of the first heating element 7664 and the second heating element 7665. The third heater assembly 7670 includes a first heating element 7666 and a second heating element 7667, each being electrically isolated from the other. Said another way, the first heating element 7666 is separate from the second heating element 7667, and vice-versa. In this manner, an electrical current can be conveyed to the first heating element 7666 independently from an electrical current being conveyed to the second heating element 7667, and vice-versa. This arrangement allows for independent control of the first heating element 7666 and the second heating element 7667.

Each of the heating elements described above are conductive traces that are fabricated on the heater layer 7646 by lithographic techniques. The first layer 7646 is between the outer bottom-most layer 7647. By arranging the heater layer 7646 within the overall circuit board, the effect of any EMF noise generated by the current supply or return to the heaters on the processor 7950 can be minimized. In other embodiments, the first heater assembly 7650 can be fabricated in any layer of the circuit board assembly 7630.

In use, the first heater assembly 7650 produces a thermal output to maintain the first temperature zone of the flow member 7610 at a first temperature. The first temperature can be, for example, between about 100 C and 115 C (to heat the sample therein to about 90 C; e.g., the "hot" temperature for a PCR thermal cycle). Additionally, the segmented, independently controllable design allows the first heating element 7661 to produce a first thermal output, the second heating element 7662 to produce a second thermal output, and the third heating element 7663 to produce a third thermal output, each of which can be different from the others. By producing different thermal outputs, the hot portion of the flow channel 7620 can be more accurately maintained at the desired temperature. The second heater assembly 7660 produces a thermal output to maintain the second temperature zone of the flow member 7610 at a second temperature. The second temperature can be different from the first temperature, and can be, for example, about 60 C to about 75 C (to heat the sample therein to about 60 C; e.g., the "cold" temperature for a PCR thermal cycle). Additionally, the segmented, independently controllable design allows the first heating element 7664 to produce a first thermal output and the second heating element 7665 to produce a second thermal output different from the first thermal output. By producing different thermal outputs, the cold portion of the flow channel 7620 can be more accurately maintained at the desired temperature. The third heater assembly 7670 produces a thermal output to maintain the third temperature zone 7613 of the flow member 7610 at a third temperature. The third temperature can be different from the first temperature and/or the second temperature. In some embodiments, the third temperature can be the same as the second temperature, and can be, for example, about 60 C to about 75 C (to heat the sample therein to about 60 C; e.g., the "cold" temperature for a PCR thermal cycle). Additionally, the segmented, independently controllable design allows the first heating element 7666 to produce a first thermal output and the second heating element 7667 to produce a second thermal output different from the first thermal output. By producing different thermal outputs, the cold portion of the flow channel 7620 can be more accurately maintained at the desired temperature.

In some embodiments, the sample flowing within the flow path 3620 is rapidly heated to about 90 C. To promote a rapid cooling down to about 60 C, in some embodiments, heat must flow out of the sample (and thus the flow member 7610). Thus, although the second temperature is described as being hotter than the desired sample temperature, in other embodiments, the output produced by the second heater assembly 7660 and/or the third heater assembly 7670 (or any of the heating elements described herein) can be such that heat flows out of the flow path 7620 and/or the flow member 7610. In such embodiments, a current can still be supplied to the second heater assembly 7660 and/or the third heater assembly 7670 to control the magnitude of the heat flow. In some embodiments, the second temperature and/or the third temperature can be, for example, between about 40 C and about 45 C (to allow heat transfer away from the sample at a controlled rate to facilitate maintaining the sample at about 60 C; e.g., the "cold" temperature for a PCR thermal cycle).

As described above, the first set of apertures 7641 produces a longitudinally oriented thermal barrier between the first heating zone 7631 and the second heating zone 7632, and the second set of apertures 7642 produces a longitudinally oriented thermal barrier between the first heating zone 7631 and the third heating zone 7633. Thus, the first set of apertures 7641 and the second set of apertures 7642 collectively thermally isolate the first heating zone 7631 of the circuit board assembly 7630. By minimizing the heat transfer between the first heating zone 7631, the second heating zone 7632, and the third heating zone 7633, accuracy and control of the temperature to which each heating zone is heated can be improved.

Figure 23:
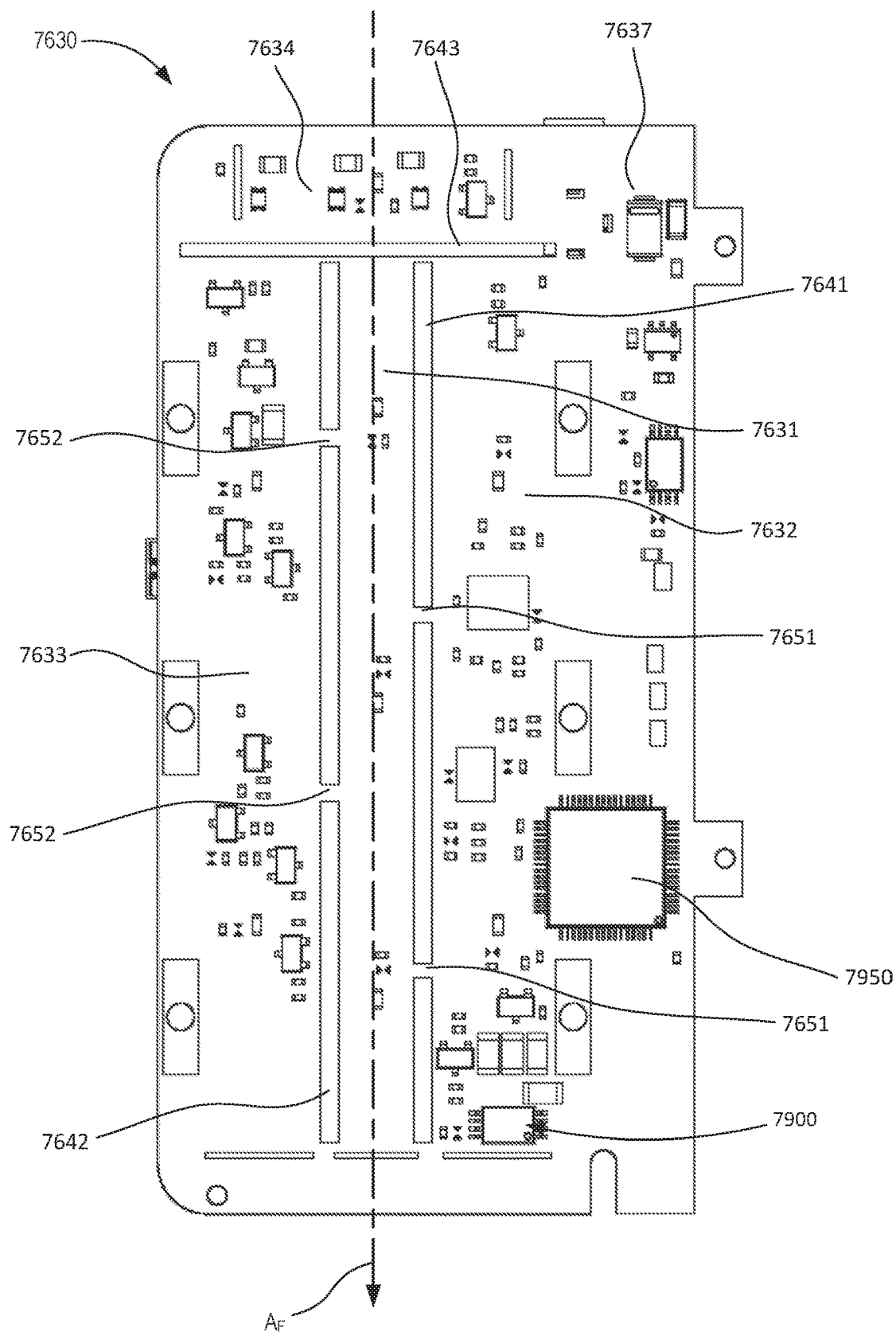
FIG. 23 is a top view of a printed circuit board of the amplification module shown in FIG. 21.

Referring to FIG. 23, the connection lugs (or portions) 7651 that separate the first set of apertures 7641 into three openings are offset from the connection lugs (or portions) 7652 that separate the second set of apertures 7642 into three openings. Similarly stated, a connection lug 7651 is located at a different longitudinal position than a corresponding connection lug 7652. Said another way, the connection lugs 7651 are positioned at a different location along the flow axis $A_F$ than are the connection lugs 7652. This arrangement allows each of the connection lugs 7651 and the connection lugs 7652 to be positioned below (or aligned with) a different channel of the flow path 7620 when the circuit board assembly 7630 is coupled to the flow member 7610. As an example, this arrangement allows a connection lug 7651 to be aligned with, for example, the tenth channel within the flow path 7620 while the corresponding connection lug 7652 is aligned with, for example, the eighteenth channel within the flow path 7620. Because the thermal performance of the first heating zone 7631 in the areas adjacent the connection lugs 7651 and 7652 is different than the thermal performance at other spatial locations, the offset arrangement of the connection lugs minimizes any differences in the temperature of the flow channel. This, in turn, increases the overall accuracy of the device.

In addition to including three heating zones for the PCR reaction, the circuit board assembly 7630 also defines a third aperture 7643 that separates a fourth portion (or heating zone) 7634 from the other heating zones. The third aperture 7643 is elongated substantially perpendicular to the flow axis $A_F$, and thus produces a laterally-oriented thermal barrier between the fourth heating zone 7634 and the amplification heating zones (i.e., the first heating zone 7631, the second heating zone 7632, and the third heating zone 7633). Although shown as being a single opening, in other embodiments the fourth heating zone 7634 can be separated by a series of apertures and connection lugs.

As shown, the fourth heating zone 7634 is disposed at an end portion of the circuit board assembly 7630. When the circuit board assembly 7630 is coupled to the flow member 7610, the fourth portion 7634 is aligned with the hot-start pattern 7623 of the flow member 7610. This arrangement allows the fourth heater assembly 7668 located within fourth heating zone 7634 to heat the hot-start pattern 7623 of the flow member 7610. The hot-start portion 7623 reduces non-specific amplification and allows the use of certain PCR reagents that remain inactive until heated. In some embodiments, the first heater assembly 7650 can be controlled to maintain the first temperature zone 7611 at a temperature of between about 45 degrees Celsius and about 95 degrees Celsius (and/or at a surface temperatures such that the fluid flowing therethrough reaches a temperature between about 45 degrees Celsius and about 95 degrees Celsius).

The fourth heating zone 7634 of the printed circuit board assembly 7630 includes a fourth heater assembly 7668. The fourth heater assembly 7668 includes a single heating element that is electrically isolated from the heating elements included in the other heating assemblies (e.g., the first heating assembly 7650). In this manner, an electrical current can be conveyed to the fourth heater assembly 7668 independently from an electrical current being conveyed to the other heating elements of the first heater assembly 7650, the second heater assembly 7660 and/or the third heater assembly 7670. This arrangement allows for independent control of the hot-start portion of the amplification module 7600.

Unlike the detection module 5800, the detection module 7800 is not coupled directly to the printed circuit board assembly 7630. Instead the detection module 7800 is coupled to (either directly or via intervening structure), the second heat sink 7692. In some embodiments, for example, the detection module 7800 can be coupled to a detection heater (not shown) that is mounted to the second heat sink 7692, and that heats portions of the detection module 7800. In other embodiments, the detection module 7800 can be coupled directly to the second heat sink 7692, which provides the desired heat (via the heater assemblies within the circuit board assembly 7630) to heat portions of the detection module 7800. In yet other embodiments, the detection module 7800 can be coupled to the second heat sink 7692 in a manner such that an air gap between the detection module 7800 and the second heat sink 7692 is produced.

The detection module 7800 is configured to receive output from the amplification module 7600 (i.e., from the flow member 7610) and reagents from a reagent module (not shown) to produce an output to indicate presence or absence of target organism in the initial input sample. The detection module 7800 can also produce an output to indicate the general correct operation of the test (positive control and negative control). For example, in some embodiments, the detection module 7800 can produce one or more colorimetric outputs. The detection module 6800 can be any of the detection modules shown and described in International Patent Publication No. WO2016/109691, entitled "Devices and Methods for Molecular Diagnostic Testing," which is incorporated herein by reference in its entirety.

The detection module 7800 includes a detection flow cell 7810 that defines a detection chamber/channel 7812 having a series of inlet and outlet portions, through which the sample and the reagents are conveyed to produce the detected output. The detection chamber 7812 includes a "read lane" 7820 (also referred to as a detection portion) that includes one or more detection surfaces or zones. In some embodiments, the detection surfaces can be chemically modified to contain hybridization probes (i.e., single stranded nucleic acid sequences that capture complementary strand of target nucleic acid.) to capture complementary strands of the amplified nucleic acid. For example, in some embodiments, the read lane can include a first detection surface that includes a hybridization probe specific to *Neisseria* gonorrhea (NG), a second detection surface that includes a hybridization probe specific to *Chlamydia trachomatis* (CT), and a third detection surface that includes a hybridization probe specific to *Trichomonas vaginalis* (TV).

In use, the post-amplification solution (from the outlet portion 7622 of the flow member 7610) is conveyed into the detection chamber 7812. After the sample is in the detection chamber 7812, DNA strands in the post-amplification solution can bind to certain detection surfaces within the read lane 7820 to facilitate production of the output signal. In some embodiments, to facilitate such binding, the detection module 7800 and/or the detection surfaces therein are heated to incubate the amplicon within the read lane (e.g., in the presence of a hybridizing probe). As described above, the detection module 7800 can be heated either by a separate heater or by the second heat sink 7692.

FIG. 26 is a flow chart of a method 10 of heating a sample (e.g., to amplify a nucleic acid therein) according to an embodiment. The method 10 can be performed using any suitable device, such as the amplification module 5600 or the amplification module 7600 described herein. The method includes conveying a sample into a diagnostic device, at 12. The diagnostic device includes a flow member coupled to a first heater assembly (e.g., the heater 1650) and a second heater assembly (e.g., the heater 1660). The flow member can be any suitable flow member (e.g., the flow member 1610) defining a flow path having a set of flow channels. In some embodiments, the first heater assembly includes a first heating element (e.g., the heating element 5661) and a second heating element (e.g., the heating element 5662). The second heater assembly includes a third heating element (e.g., the heating element 5664) and a fourth heating element (e.g., the heating element 5665).

The method 10 includes actuating the diagnostic device, at 13. Upon actuation, a current is supplied, at a first time, to the first heating element and the third heating element, at 13A. The current is supplied such that the first heating element maintains at least a first portion of a first channel from the set of channels at a first temperature, and the third heating element maintains at least a second portion of the first channel from the set of channels at a second temperature. In response to the actuation, a flow of sample within the flow path is produced at a second time, at 13B. The second time occurs after the first time. In this manner, the method 10 provides for the first heating element and the third heating element to be activated before the flow of sample is introduced. In response to the actuation, a current is supplied, at a third time, to the second heating element and the fourth heating element, at 13C. The current is supplied such that the second heating element maintains at least a first portion of a second channel from the set of channels at the first temperature, and the fourth heating element maintains at least a second portion of the second channel from the set of channels at the second temperature. The third time is different from the first time. In this manner, the second and fourth heating elements, which supply heat to subsequent flow channels (e.g., the last flow channel) are activated at a later time, thus conserving power and/or minimizing peak power usage.

FIG. 27 is a flow chart of a method 20 of heating a sample (e.g., to amplify a nucleic acid therein), according to an embodiment. The method 20 can be performed using any suitable device, such as the amplification module 5600 or the amplification module 7600 described herein. The method includes conveying a sample into a diagnostic device, at 22. The diagnostic device, which can be the device 7000, includes a flow member coupled to a heater assembly. The flow member can be any of the flow members described herein, and defines a flow path. The heater assembly (or printed circuit board assembly) includes a substrate, a first heating element, and a second heating element. The heater assembly is coupled to the flow member such that the first heating element is between a first portion of the substrate and a first portion of the flow path, and the second heating element is between a second portion of the substrate and a second portion of the flow path. A third portion of the substrate separates the first portion of the substrate and the second portion of the substrate. The third portion of the substrate is characterized by a thermal conductivity that is less than a thermal conductivity of the first portion of the substrate.

The method 20 includes actuating the diagnostic device, at 23. Upon actuation, a first current is supplied to the first heating element such that the first heating element maintains the first portion of the flow path at a first temperature, at 23A. A second current is supplied to the second heating element such that the second heating element maintains the second portion of the flow path at a second temperature, at 23B. The second temperature different from the first temperature. A flow of sample within the flow path is produced, at 23C.

Figure 28:
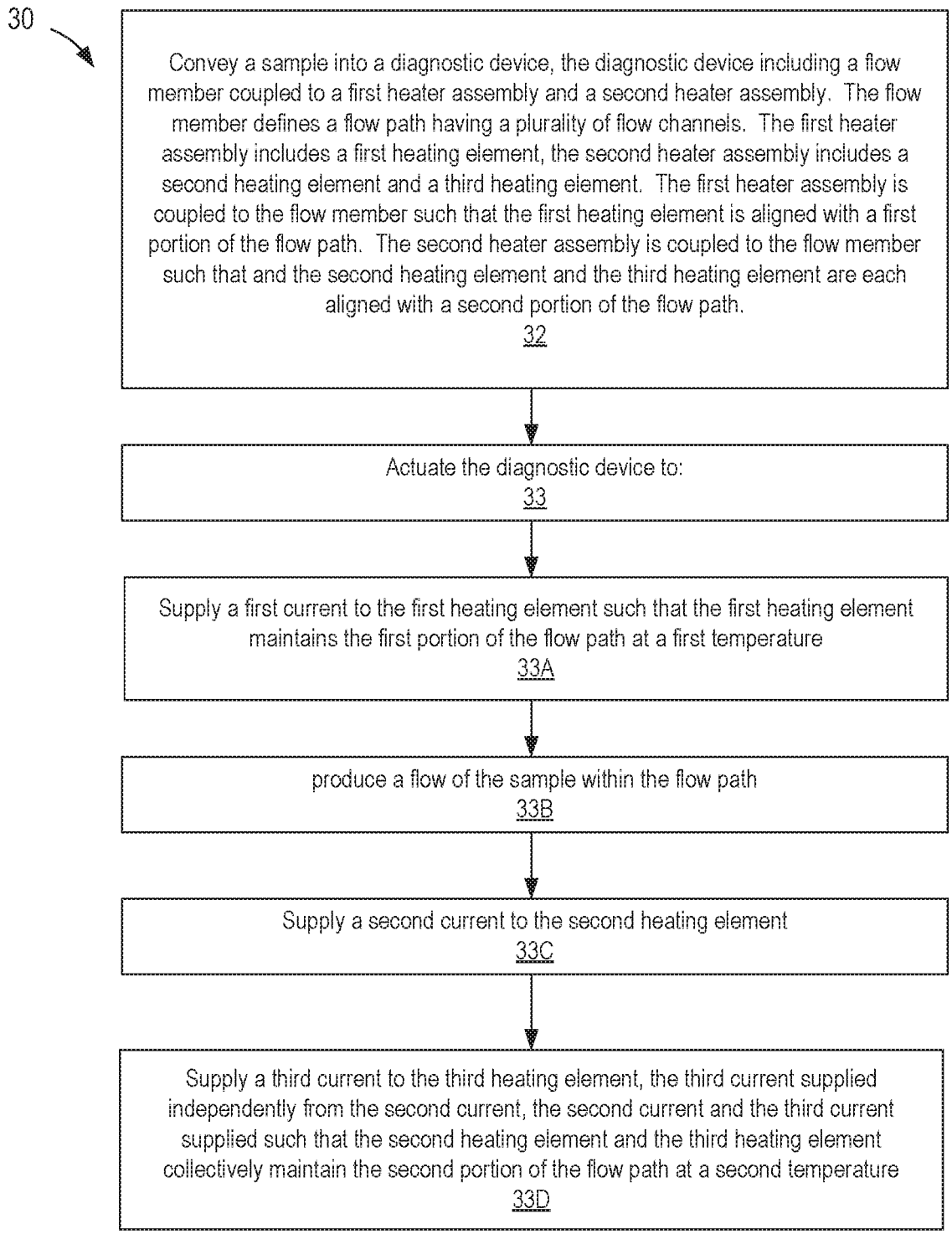
FIG. 28 shows a flow chart of a method of performing a thermal process on a sample, according to an embodiment.

FIG. 28 is a flow chart of a method 30 of heating a sample (e.g., to amplify a nucleic acid therein), according to an embodiment. The method 30 can be performed using any suitable device, such as the amplification module 5600 or the amplification module 7600 described herein. The method includes conveying a sample into a diagnostic device, at 32. The diagnostic device, which can be the device 7000, includes a flow member coupled to a first heater assembly and a second heater assembly. The flow member defines a flow path having a series of flow channels. The first heater assembly includes a first heating element. The second heater assembly includes a second heating element and a third heating element. The first heater assembly is coupled to the flow member such that the first heating element is aligned with a first portion of the flow path. The second heater assembly is coupled to the flow member such that and the second heating element and the third heating element are each aligned with a second portion of the flow path.

The method 30 includes actuating the diagnostic device, at 33. Upon actuation, a first current is supplied to the first heating element such that the first heating element maintains the first portion of the flow path at a first temperature, at 33A. A flow of sample within the flow path is produced, at 33B. A second current is supplied to the second heating element, at 33C. A third current is supplied to the third heating element, at 33D. The third current is supplied independently from the second current. The second current and the third current are supplied such that the second heating element and the third heating element collectively maintain the second portion of the flow path at a second temperature.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

For example, any of the amplification modules, heater assemblies, and detection modules shown and described herein can be used in any suitable diagnostic device. Such devices can include, for example, a single-use device that can be used in a point-of-care setting and/or in a user's home. Similarly stated, in some embodiments, the device (and any of the other devices shown and described herein) can be configured for use in a decentralized test facility. Further, in some embodiments, any of the amplification modules, heater assemblies, and detection modules shown and described herein can be included within a CLIA-waived device and/or can facilitate the operation of a device in accordance with methods that are CLIA waived. Similarly stated, in some embodiments, the amplification modules, heater assemblies, and detection modules shown and described herein can facilitate operation of a device in a sufficiently simple manner that can produce results with sufficient accuracy to pose a limited likelihood of misuse and/or to pose a limited risk of harm if used improperly. In some embodiments, the amplification modules, heater assemblies, and detection modules shown and described herein can be used in any of the diagnostic devices shown and described in International Patent Publication No. WO2016/109691, entitled "Devices and Methods for Molecular Diagnostic Testing," which is incorporated herein by reference in its entirety," which is incorporated herein by reference in its entirety.

The devices and methods described herein, however, are not limited to performing a molecular diagnostic test on human samples. In some embodiments, any of the devices and methods described herein can be used with veterinary samples, food samples, and/or environmental samples.

Although the substrates (e.g. the substrate 1640, 2640, 3640, 4640, 5640, and others) are shown and described herein as being rigid and having a glass transition temperature (Tg) of at least about 170 degrees Celsius, in other embodiments, an amplification module can include a substrate (e.g. the substrate 1640, 2640, 3640, 4640, 5640, and others) having an suitable glass transition temperature (Tg), such as a Tg of as low as 120 degrees Celsius or 100 degrees Celsius. In other embodiments, an amplification module can include a substrate (e.g. the substrate 1640, 2640, 3640, 4640, 5640, and others) having a flexible substrate. For example, in some embodiments, an amplification module can include a substrate constructed from any of Pyralux®, Nikaflex®, or Kapton®.

Although the first heater assembly 5650 is shown and described as including three independently controllable heating elements, in other embodiments, any of the heater assemblies shown and described herein can include any suitable number of independently controllable heating elements.

Although the heater assembly 5630 is shown and described as include a first connection lug (or portion) 5651 that is longitudinally offset from a second connection lug (or portion) 5652 by a distance equal to that of one or two flow channels, in other embodiments, a heater assembly can include a first connection lug that is longitudinally offset from a second connection lug by any suitable distance, such as for example, by a distance equal to about 4 flow channels, between 4 and 6 flow channels, between 6 and 8 flow channels, between 8 and 10 flow channels, and between 10 and 12 flow channels.

In some embodiments, any of the amplification modules described can be configured to conduct a "rapid" PCR (e.g., completing at least 30 cycles in less than about 10 minutes), and rapid production of an output signal (e.g., via a detection module). Similarly stated, the amplification modules described herein can be configured to process volumes, to have dimensional sizes and/or be constructed from materials that facilitates a rapid PCR or amplification in less than about 10 minutes, less than about 9 minutes, less than about 8 minutes, less than about 7 minutes, less than about 6 minutes, or any range therebetween, as described herein.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The processor 7950 (and any of the processors and/or controllers described herein) can be any processor configured to, for example, write data into and read data from the memory of the controller, and execute the instructions and/or methods stored within the memory. Furthermore, the processor can be configured to control operation of the other modules within the controller (e.g., the temperature feedback module and the flow module). Specifically, the processor can receive a signal including temperature data, current measurements or the like and determine an amount of power and/or current to be supplied to each heater assembly, the desired timing and sequence of the piston pulses and the like. For example, in some embodiments, the controller can be an 8-bit PIC microcontroller, which will control the power delivered to various heating assemblies and components within the amplification module 5600. This microcontroller can also contain code for and/or be configured to minimize the instantaneous power requirements on the power source. The highest power consumption can occur, for example, when amplification heaters (e.g. the first heating assembly 5650, the second heating assembly 5660, and the third heating assembly 5670) are being raised to temperature. By scheduling these warmup times during periods of low power consumption of other portions of the device within which the amplification module 5600 is employed, the power requirements on the power source can be reduced at the expense of increased energy consumption. When multiple loads require power simultaneously, the controller contains code for and/or is configured to ensure that each load receives the necessary average power while minimizing the time in which multiple loads are powered simultaneously. This is achieved by interleaving the PWM signals to each load such that the periods in which both signals are in an on state is kept to a minimum.

In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the controller (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the pressure feedback module and the position feedback module) can be implemented by the processor and/or stored within the memory.

Although various embodiments have been described as having particular features and/or combinations of components, other embodiments are possible having a combination of any features and/or components from any of embodiments as discussed above.

For example, although the substrate 4640 is not shown as defining an aperture, in other embodiments, the substrate 4640 (or any of the other substrates shown or described herein) can define an aperture similar to the aperture 1641 shown and described with reference to the amplification module 1600.

As another example, although the circuit board assembly 5630 is shown and described as including a series of apertures (e.g., apertures 5641, apertures 5642, and the like) that function as a thermal barrier between adjacent portion of the assembly 5630, in other embodiments, any of the circuit board assemblies described herein (including the assembly 5630 and the assembly 7630) can include any suitable mechanism for limiting the heat transfer between various portions of the device. For example, in some embodiments, the circuit board assembly 5630, the circuit board assembly 7630, or any other circuit board assembly herein can include regions that are constructed from (and/or include) a material having a thermal conductivity that is lower than that of the material(s) from which other portions of the circuit board assembly are constructed, similar to the heater assembly 2630 described above. For example, in some embodiments, the circuit board assembly 5630, the circuit board assembly 7630, or any other circuit board assembly herein can include portions that are constructed from a material having a thermal conductivity of about 0.1 W/m-K or less. In other embodiments, the circuit board assembly 5630, the circuit board assembly 7630, or any other circuit board assembly herein can include portions that are constructed from a material having a thermal conductivity of about 0.05 W/m-K or less. For example, in some embodiments, the circuit board assembly 5630, the circuit board assembly 7630, or any other circuit board assembly herein can include portions that are constructed from or include a rigid foam (e.g., polyurethane foam, a silicon foam, a neoprene foam, a vinyl foam, or the like).

Any of the devices and methods described herein can be utilized to detect the presence or absence of nucleic acids associated with one or more bacterial cells in a biological sample. In some embodiments, the one or more bacterial cells are pathogens. In some embodiments, the one or more bacterial cells are infectious. Non-limiting examples of bacterial pathogens that can be detected include Mycobacteria (e.g., *M. tuberculosis, M. bovis, M. avium, M. leprae,* and *M. africanum*), *rickettsia, mycoplasma, chlamydia,* and *legionella*. Some examples of bacterial infections include, but are not limited to, infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, and *Neisseria* species. Specific examples of infectious bacteria include, but are not limited to: *Helicobacter pyloris, Legionella pneumophilia, Mycobacterium tuberculosis, Mycobacterium avium, Mycobacterium intracellulare, Mycobacterium kansaii, Mycobacterium gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Erysipelothrix rhusiopathiae, Clostridium tetani, Enterobacter aerogenes, Klebsiella pneumoniae, Pasteurella multocida, Fusobacterium nucleatum, Streptobacillus moniliformis, Treponema pallidium, Treponema pertenue, Leptospira, Rickettsia,* and *Actinomyces israelii, Acinetobacter, Bacillus, Bordetella, Borrelia, Brucella, Campylobacter, Chlamydia, Chlamydophila, Clostridium, Corynebacterium, Enterococcus, Haemophilus, Helicobacter, Mycobacterium, Mycoplasma, Stenotrophomonas, Treponema, Vibrio, Yersinia, Acinetobacter baumanii, Bordetella pertussis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Corynebacterium diphtheriae, Enterobacter sazakii, Enterobacter agglomerans, Enterobacter cloacae, Enterococcus faecalis, Enterococcus faecium, Escherichia coli, Francisella tularensis, Helicobacter pylori, Legionella pneumophila, Leptospira interrogans, Mycobacterium leprae, Mycobacterium tuberculosis, Mycobacterium ulcerans, Mycoplasma pneumoniae, Pseudomonas aeruginosa, Rickettsia rickettsii, Salmonella typhi, Salmonella typhimurium, Salmonella enterica, Shigella sonnei, Staphylococcus epidermidis, Staphylococcus saprophyticus, Stenotrophomonas maltophilia, Vibrio cholerae, Yersinia pestis,* and the like. In some instances, the infectious bacteria is *Neisseria gonorrhoeae* or *Chlamydia trachomatis*.

Any of the devices and methods described herein can be utilized to detect the presence or absence of nucleic acids associated with one or more viruses in a biological sample. Non-limiting examples of viruses include the herpes virus (e.g., human cytomegalomous virus (HCMV), herpes simplex virus I (HSV-1), herpes simplex virus 2 (HSV-2), varicella zoster virus (VZV), Epstein-Barr virus), influenza A virus and Hepatitis C virus (HCV) or a picornavirus such as Coxsackievirus B3 (CVB3). Other viruses may include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B 19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In some embodiments, the virus is an enveloped virus. Examples of such enveloped viruses include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicellazoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoon pox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta torn virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses A1-22, 24 (CA1-22 and CA24, CA23 (echovirus 9)), human coxsackieviruses (B1-6 (CB1-6)), human echoviruses 1-7, 9, 11-27, 29-33, vilyuish virus, simian enteroviruses 1-18 (SEVI-18), porcine enteroviruses 1-11 (PEV1-11), bovine enteroviruses 1-2 (BEVI-2), hepatitis A virus, rhinoviruses, hepatoviruses, cardio viruses, aphthoviruses and echoviruses. The virus may be phage. Examples of phages include, but are not limited to T4, T5, λ, phage, T7 phage, G4, P1, φ6, Thermoproteus tenax virus 1, M13, MS2, Qβ, φ X174, Φ29, PZA, Φ15, BS32, B103, M2Y (M2), Nf, GA-I, FWLBc1, FWLBc2, FWLLm3, B4. The reference database may comprise sequences for phage that are pathogenic, protective, or both. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Arna virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana *myotis* leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O' nyong'nyong virus, and the chikungunya virus; a member of the Poxyridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or HINI swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picomaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types I and 2), and human T-lymphotropic virus Types I and II (HTLV-1 and HTLV-2, respectively).

Any of the devices and methods described herein can be utilized to detect the presence or absence of nucleic acids associated with one or more fungi in a biological sample. Examples of infectious fungal agents include, without limitation *Aspergillus, Blastomyces, Coccidioides, Cryptococcus, Histoplasma, Paracoccidioides, Sporothrix*, and at least three genera of *Zygomycetes*. The above fungi, as well as many other fungi, can cause disease in pets and companion animals. The present teaching is inclusive of substrates that contact animals directly or indirectly. Examples of organisms that cause disease in animals include *Malassezia furfur, Epidermophyton floccosur, Trichophyton mentagrophytes, Trichophyton rubrum, Trichophyton tonsurans, Trichophyton equinum, Dermatophilus congolensis, Microsporum canis, Microsporu audouinii, Microsporum gypseum, Malassezia ovale, Pseudallescheria, Scopulariopsis, Scedosporium*, and *Candida albicans*. Further examples of fungal infectious agent include, but are not limited to, *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*.

Any of the devices and methods described herein can be utilized to detect the presence or absence of nucleic acids associated with one or more parasites in a biological sample. Non-limiting examples of parasites include *Plasmodium, Leishmania, Babesia, Treponema, Borrelia, Trypanosoma, Toxoplasma gondii, Plasmodium falciparum, P. vivax, P. ovale, P. malariae, Trypanosoma* spp., or *Legionella* spp. In some cases, the parasite is *Trichomonas vaginalis*.

What is claimed is:

1. An apparatus, comprising:
 a flow member defining a plurality of flow channels through which a sample can flow from an inlet opening to an outlet opening, the flow member defining a flow axis;
 a substrate including a first portion, a second portion, and a third portion, the third portion between the first portion and the second portion;
 a first heating element coupled to the first portion of the substrate, the first heating element configured to produce a first thermal output;
 a second heating element coupled to the second portion of the substrate, the second heating element configured to produce a second thermal output, the second thermal output different from the first thermal output;
 a third heating element coupled to the third portion of the substrate, the third heating element configured to produce a third thermal output;
 the substrate defining a first plurality of apertures that separate the third portion of the substrate from the first portion of the substrate and a second plurality of apertures that separate the second portion of the substrate from the third portion of the substrate;
 the substrate including a first connection portion between a first aperture from the first plurality of apertures and an adjacent second aperture from the first plurality of apertures; and
 the substrate including a second connection portion between a first aperture from the second plurality of apertures and an adjacent second aperture from the second plurality of apertures, the first connection portion offset from the second connection portion along the flow axis, the flow member coupled to the substrate such that a temperature difference between a first flow channel from the plurality of flow channels and a second flow channel from the plurality of flow channels is minimized.

2. The apparatus of claim 1, wherein:
 the third portion of the substrate is constructed from a material that is different from a material from which at least one of the first portion of the substrate or the second portion of the substrate is constructed.

3. The apparatus of claim 1, wherein:
 the first heating element is coupled to an outer surface of the first portion of the substrate; and
 the second heating element is coupled to an outer surface of the second portion of the substrate, the outer surface of the first portion of the substrate being coplanar with the outer surface of the second portion of the substrate.

4. The apparatus of claim 1, wherein the first heating element and the second heating element are constructed from a first layer bonded to the substrate, the apparatus further comprising:
 a second layer bonded between the first layer and the substrate, the second layer including a thermally conductive portion disposed beneath the second heating element, the second layer including a thermally isolative portion disposed beneath the first heating element.

5. The apparatus of claim 1, wherein:
 the flow member defines a flow path, the flow member is coupled to the substrate such that the first heating element, the second heating element, and the third heating element are between the flow member and the substrate,
 the first heating element and the flow member collectively configured to maintain a temperature of a first portion of the flow path at a first temperature, the second heating element and the flow member collectively configured to maintain a temperature of a second portion of the flow path at a second temperature, and the third heating element and the flow member collectively configured to maintain a temperature of a third portion of the flow path.

6. The apparatus of claim 5, wherein the flow member is constructed from at least one of a cyclic olefin copolymer or a graphite-based material and has a thickness of less than about 0.5 mm.

7. An apparatus, comprising:
a flow member defining a plurality of flow channels through which a sample can flow from an inlet opening to an outlet opening, the flow member defining a flow axis;
a substrate defining a first plurality of apertures that separate a first portion of the substrate from a second portion of the substrate and a second plurality of apertures that separate a third portion of the substrate from the first portion of the substrate;
a first heater assembly coupled between the substrate and the flow member, the first heater assembly configured to maintain a first portion of the flow member at a first temperature, the first heater assembly including a first plurality of heating elements along the flow axis, each heating element from the first plurality of heating elements being electrically isolated from the other heating elements from the first plurality of heating elements; and
a second heater assembly coupled between the substrate and the flow member, the second heater assembly configured to maintain a second portion of the flow member at a second temperature, the second heater assembly including a second plurality of heating elements along the flow axis, each heating element from the second plurality of heating elements being electrically isolated from the other heating elements from the second plurality of heating elements,
the substrate including a first connection portion between a first aperture from the first plurality of apertures and an adjacent second aperture from the first plurality of apertures,
the substrate including a second connection portion between a first aperture from the first plurality of apertures and an adjacent second aperture from the second plurality of apertures,
the first connection portion aligned with a first flow channel from the plurality of flow channels and the second connection portion aligned with a second flow channel from the plurality of flow channels, the first flow channel being different than the second flow channel.

8. The apparatus of claim 7, wherein the flow member, the first heater assembly and the second heater assembly are collectively configured to amplify a nucleic acid within the sample when the sample flows through the plurality of flow channels.

9. The apparatus of claim 7, wherein the flow member, the first heater assembly and the second heater assembly are collectively configured to amplify a nucleic acid within the sample via a thermal cycling amplification or an isothermal amplification.

10. The apparatus of claim 7, wherein:
the plurality of flow channels form a serpentine flow path;
the flow member, the first heater assembly and the second heater assembly are collectively configured to thermally cycle the sample flowing through the serpentine flow path to amplify a nucleic acid within the sample;
a first heating element from the first plurality of heating elements and a first heating element from the second plurality of heating elements being aligned with at least an initial flow channel from the plurality of flow channels within the serpentine flow path; and
a second heating element from the first plurality of heating elements and a second heating element from the second plurality of heating elements being aligned with at least a last flow channel from the plurality of flow channels within the serpentine flow path.

11. The apparatus of claim 10, wherein at least one of the second heating element from the first plurality of heating elements or the second heating element from the second plurality of heating elements extends along the flow axis beyond the last flow channel.

12. The apparatus of claim 7, wherein the first heater assembly and the second heater assembly are constructed from a first layer bonded to the substrate, the apparatus further comprising:
a second layer bonded between the first layer and the substrate, the second layer including a thermally conductive portion disposed beneath the second heater assembly, the second layer including a thermally isolative portion disposed beneath the first heater assembly.

13. The apparatus of claim 7, wherein:
the first heater assembly is coupled to the first portion of the substrate; and
the second heater assembly is coupled to the second portion of the substrate.

14. The apparatus of claim 7, wherein the flow member is irreversibly coupled to the substrate via an adhesive bond.

15. The apparatus of claim 14, wherein the flow member is constructed from at least one of a cyclic olefin copolymer or a graphite-based material and has a thickness of less than about 0.5 mm.

16. The apparatus of claim 8, further comprising:
a controller configured to control independently a current to each of a first heating element from the first plurality of heating elements, a second heating element from the first plurality of heating elements, a first heating element from the second plurality of heating elements, and a second heating element from the second plurality of heating elements.

17. The apparatus of claim 16, wherein the controller is configured to control a flow rate of the sample through the plurality of flow channels.

18. The apparatus of claim 16, wherein the first heater assembly and the second heater assembly are constructed from a first layer bonded to the substrate, the apparatus further comprising:
a second layer bonded between the first layer and the substrate, the second layer including a thermally conductive portion configured to reduce electromagnetic interference conveyed to the controller.

19. The apparatus of claim 16, wherein the controller is implemented in at least one of a memory or a processor, the controller including a thermal control module configured to produce a thermal control signal to adjust the current to each of the first heating element from the first plurality of heating elements, the second heating element from the first plurality of heating elements, the first heating element from the second plurality of heating elements, and the second heating element from the second plurality of heating elements.

* * * * *